(12) United States Patent
Quek et al.

(10) Patent No.: US 12,370,492 B2
(45) Date of Patent: Jul. 29, 2025

(54) METHOD AND SYSTEM FOR DESIGNING AND ASSESSING THE PERFORMANCE OF A HOLLOW FIBRE MEMBRANE CONTACTOR (MBC) IN A NATURAL GAS SWEETENING PROCESS

(71) Applicant: PETROLIAM NASIONAL BERHAD (PETRONAS), Kuala Lumpur (MY)

(72) Inventors: Ven Chian Quek, Kuala Lumpur (MY); Benoit Chachuat, London (GB); Nilay Shah, London (GB); Siti Hajar Bt Khalit, Kuala Lumpur (MY); Syafiqa Bt M Saleh, Kuala Lumpur (MY); Zhe Phak Chan, Kuala Lumpur (MY)

(73) Assignee: PETROLIAM NASIONAL BERHAD (PETRONAS), Kuala Lumpur (MY)

( * ) Notice: Subject to any disclaimer, the term of this patent is extended or adjusted under 35 U.S.C. 154(b) by 528 days.

(21) Appl. No.: 17/915,321

(22) PCT Filed: Apr. 21, 2021

(86) PCT No.: PCT/MY2021/050030
§ 371 (c)(1),
(2) Date: Sep. 28, 2022

(87) PCT Pub. No.: WO2021/215907
PCT Pub. Date: Oct. 28, 2021

(65) Prior Publication Data
US 2023/0201760 A1      Jun. 29, 2023

(30) Foreign Application Priority Data
Apr. 24, 2020   (MY) ................... 2020002080

(51) Int. Cl.
*B01D 53/14*   (2006.01)
*B01D 53/18*   (2006.01)
(Continued)

(52) U.S. Cl.
CPC ........ *B01D 53/1475* (2013.01); *B01D 53/18* (2013.01); *B01D 53/22* (2013.01);
(Continued)

(58) Field of Classification Search
None
See application file for complete search history.

(56) References Cited

U.S. PATENT DOCUMENTS

| | | | |
|---|---|---|---|
| 3,960,707 A | 6/1976 | Gross et al. | |
| 5,774,381 A | 6/1998 | Meier | |

(Continued)

FOREIGN PATENT DOCUMENTS

| | | | |
|---|---|---|---|
| CN | 102438728 A | 5/2012 | |
| CN | 102890639 A | 1/2013 | |

(Continued)

OTHER PUBLICATIONS

Addington and Ness, "An Evaluation of General "Rules of Thumb" in Amine Sweetening Unit Design and Operation," GPA Annual Convention Proceedings 1:119-135 (2010).

(Continued)

*Primary Examiner* — Colin W. Slifka
(74) *Attorney, Agent, or Firm* — Troutman Pepper Locke LLP (Rochester)

(57) ABSTRACT

A computer-implemented method for designing and assessing the performance of a hollow fibre membrane contactor (MBC) in a natural gas sweetening process using a MBC model is described in an embodiment. The MBC model comprises model parameters, model equations and boundary conditions for calculating data associated with the natural gas sweetening process. The natural gas sweetening process comprises removal of acid gas from natural gas using a solvent comprising at least one component. The method comprises: (i) forming a regression model using empirical (Continued)

data; (ii) determining a Henry's constant of $CO_2$ in the solvent using the regression model; (iii) inputting the determined Henry's constant of $CO_2$ in the MBC model as one of the model parameters; and (iv) determining $CO_2$ absorption in the solvent using the MBC model for designing and assessing the performance of the MBC.

20 Claims, 26 Drawing Sheets

(51) Int. Cl.
    *B01D 53/22*     (2006.01)
    *B01D 63/02*     (2006.01)
    *B01D 63/04*     (2006.01)
    *C10L 3/10*     (2006.01)
    *G06F 30/20*     (2020.01)

(52) U.S. Cl.
    CPC ............. *B01D 63/02* (2013.01); *B01D 63/04* (2013.01); *C10L 3/104* (2013.01); *B01D 2053/224* (2013.01); *B01D 2256/24* (2013.01); *B01D 2257/504* (2013.01); *C10L 2290/548* (2013.01); *G06F 30/20* (2020.01)

(56) References Cited

U.S. PATENT DOCUMENTS

| | | | |
|---|---|---|---|
| 6,565,624 | B2 | 5/2003 | Kutt et al. |
| 7,272,544 | B2 | 9/2007 | Gopal et al. |
| 7,627,461 | B2 | 12/2009 | Guyaguler et al. |
| 2004/0123737 | A1 | 7/2004 | Filippi et al. |
| 2008/0011161 | A1 | 1/2008 | Finkenrath et al. |
| 2010/0332273 | A1 | 12/2010 | Balasubramanian et al. |
| 2011/0100794 | A1 | 5/2011 | Hanley |
| 2012/0055385 | A1 | 3/2012 | Lien et al. |
| 2016/0121258 | A1 | 5/2016 | First et al. |
| 2019/0193020 | A1* | 6/2019 | Bara ....................... B01D 53/22 |

FOREIGN PATENT DOCUMENTS

| | | |
|---|---|---|
| CN | 104657784 A | 5/2015 |
| CN | 106940738 A | 7/2017 |
| EP | 1760418 A1 | 3/2007 |
| KR | 20190067398 A | 6/2019 |
| WO | 2012047782 A1 | 4/2012 |
| WO | 2014/204291 A1 | 12/2014 |
| WO | 2015/003286 A1 | 1/2015 |
| WO | 2017/180167 A1 | 10/2017 |

OTHER PUBLICATIONS

Al-Baghli et al., "A rate-based model for the design of gas absorbers for the removal of CO2 and H2S using aqueous solutions of MEA and DEA," Fluid Phase Equilibria, 185(1-2):31-43 (2001).
Al-Marzouqi et al., "Modeling of chemical absorption of CO2 in membrane contactors," Separation and Purification Technology, 62(3):499-506 (2008).
Al-Marzouqi et al., "Modeling of CO2 absorption in membrane contactors', Separation and Purification Technology," 59(3):286-293 (2008).
Al-Marzouqi et al., "CO2 Removal from CO2—CH4 Gas Mixture Using Different Solvents and Hollow Fiber Membranes," 48:3600-3605 (2009).
Alie, C. F., CO2 Capture With MEA: Integrating the Absorption Process and Steam Cycle of an Existing Coal-Fired Power Plant, Master Thesis, University of Waterloo (2004).
Bailey and Feron, "Post-combustion decarbonisation processes," Oil and Gas Science and Technology, 60(3):461-474 (2005).
Bensetiti et al., "Solubility of Nitrous Oxide in Amine Aqueous Solutions," Ind. Eng.Chem. Res, 38:328-332 (1999).

Billet and Schultes, "Prediction of mass transfer columns with dumped and arranged packings," Trans IChemE, 77:498-504 (1999).
Boributh et al., "A modeling study on the effects of membrane characteristics and operating parameters on physical absorption of CO2 by hollow fiber membrane contactor," Journal of Membrane Science. Elsevier B.V., 380(1-2):21-33 (2011).
Boributh et al., "Mathematical modeling and cascade design of hollow fiber membrane contactor for CO2 absorption by monoethanolamine," Journal of Membrane Science. Elsevier B.V., 401-402:175-189 (2012).
Boucif et al., "To What Extent Does Temperature Affect Absorption in Gas-Liquid Hollow Fiber Membrane Contactors?," Separation Science and Technology, 50(9): 1331-1343 (2015).
Carroll et al., "The solubility of hydrocarbons in amine solutions," Laurance Reid Gas Conditioning Conference, (March), pp. 44-64 (1998).
Chabanon et al., "Modeling strategies of membrane contactors for post-combustion carbon capture: A critical comparative study," Chemical Engineering Science. Elsevier, 87:393-407 (2013).
Chemeo, Chemical Properties of Methyldiethanolamine (CAS 105-59-9) (2017).
Chemeo, Chemical Properties of Piperazine (CAS 110-85-0) (2017).
Constantinou, A., "CO2 Absorption in Microstructured Membrane Reactors,". PhD Thesis, University College London (2011).
Cormos and Daraban, "Dynamic modeling and validation of amine-based CO2 capture plant." Applied Thermal Engineering. Elsevier Ltd, 74:202-209 (2015).
Cui et al., "Modelling and Experimental Study of Membrane Wetting in Microporous Hollow Fiber Membrane Contactors," The Canadian Journal of Chemical Engineering, 93(7): 1254-1265 (2015).
Dave et al., "CO2 capture by aqueous amines and aqueous ammonia-A Comparison," Energy Procedia. Elsevier, 1(1):949-954 (2009).
Demontigny et al., "Using polypropylene and polytetrafluoroethylene membranes in a membrane contactor for CO2 absorption," Journal of Membrane Science, 277:99-107 (2006).
DeDeshmukh and Li, "Effect of ethanol composition in water coagulation bath on morphology of PVDF hollow fibre membranes," Journal of Membrane Science, 150(1):75-85 (1998).
Dindore, V. Y., "Gas Purification using Membrane Gas Absorption Processes," PhD Thesis, University of Twente, the Netherlands (2003).
Dindore and Versteeg, "Gas-liquid mass transfer in a cross-flow hollow fiber module: Analytical model and experimental validation," International Journal of Heat and Mass Transfer, 48(16):3352-3362 (2005).
Eslami et al., "Modeling and simulation of CO2 removal from power plant flue gas by PG solution in a hollow fiber membrane contactor," Advances in Engineering Software. Elsevier Ltd, 42(8):612-620 (2011).
Faiz and Al-Marzouqi, "CO2 removal from natural gas at high pressure using membrane contactors: Model validation and membrane parametric studies'," Journal of Membrane Science. Elsevier B.V., 365(1-2):232-241 (2010).
Faiz et al., :"Significance of gas velocity change during the transport of CO2 through hollow fiber membrane contactors," Chemical Engineering Journal. Elsevier B.V., 168(2):593-603 (2011).
Falk-Pedersen and Dannstrom, "Separation of carbon dioxide from offshore gas turbine exhaust," Energy Conversion and Management, 38:S81-S86 (1997).
Favre, E., "Membrane processes and postcombustion carbon dioxide capture: Challenges and prospects," Chemical Engineering Journal. Elsevier B.V., 171(3):782-793 (2011).
Gaspar et al., "Rate-based Modelling and Validation of a Pilot Absorber Using MDEA Enhanced with Carbonic Anhydrase (CA)," Energy Procedia. The Author(s), 114(Nov. 2016):707-718 (2017).
Ghasem et al., Modeling of CO2 absorption in a membrane contactor considering solvent evaporation,: Separation and Purification Technology, Elsevier B.V., 110:1-10 (2013).
Goyal et al., "Mathematical modeling of CO2 separation from gaseous-mixture using a Hollow-Fiber Membrane Module: Physical mechanism and influence of partial-wetting," Journal of Membrane Science. Elsevier, 474:64-82 (2015).

(56) References Cited

OTHER PUBLICATIONS

Hatcher et al., "Solubility of hydrocarbons and light ends in amines," Optimized Gas Treating, Inc. (2013).
He and Hägg, "Membranes for environmentally friendly energy processes," Membranes, 2(4):706-726 (2012).
Hoff et al., "Modeling and Experimental Study of Carbon Dioxide Absorption in Aqueous Alkanolamine Solutions using a Membrane Contactor," Industrial & Engineering Chemistry Research, 43:4908-4921 (2004).
Hoff, K. A., Modeling and Experimental Study of Carbon Dioxide Absorption in a Membrane Contactor, Science and Technology. PhD Thesis, Norwegian University of Science and Technology (2003).
Hoff and Svendsen, "CO2 absorption with membrane contactors vs. packed absorbers—Challenges and opportunities in post combustion capture and natural gas sweetening," Energy Procedia. Elsevier B.V., 37(1876):952-960 (2013).
Hoff and Svendsen, "Membrane contactors for CO2 absorption—Application, modeling and mass transfer effects," Chemical Engineering Science. Elsevier, 116:331-341 (2014).
Iea Energy Technology Analysis: Prospects for CO2 Capture and Storage, pp. 1-249 (2004) doi: 10.1016/B978-1-85617-710-8.00010-8.
Iversen et al., "Characterization of microporous membranes for use in membrane contactors," Elsevier, Membrane Science, 130:205-217 (1997).
Kabadi, V. N., "Heat of Dissolution Measurements for CO2 in Mixed Alkanolamine Solvents," Final Report DE-FG26-03NT41912. North Carolina A&T State University, Greensbor (2007).
Kamo et al., "Solvent-induced morphological change of microporous hollow fiber membranes," Journal of Membrane Science 70(2-3):217-224 (1992).
Kang et al., "Removal of high concentration CO2 from natural gas using high pressure membrane contactors," International Journal of Greenhouse Gas Control. Elsevier Ltd, 60:1-9 (2017).
Keshavarz et al., "Analysis of CO2 separation and simulation of a partially wetted hollow fiber membrane contactor," Journal of Hazardous Materials, 152(3):1237-1247 (2008).
Khaisri et al., "Comparing membrane resistance and absorption performance of three different membranes in a gas absorption membrane contactor," Separation and Purification Technology, 65:290-297 (2009).
Khaisri et al., "A mathematical model for gas absorption membrane contactors that studies the effect of partially wetted membranes," Journal of Membrane Science, 347(1-2):228-239 (2010).
Kidnay and Parrish, "Fundamentals of Natural Gas Processing," Mechanical Engineering, CRC Press, Columbus Division, Battelle Memorial Institute and Department of Mechanical Engineering The Ohio State University Columbus, Ohio. doi: 10.1201/b14397 (2006).
Ko and Li, "Kinetics of absorption of carbon dioxide into solutions of N-methyldiethanolamine # water," Chemical Engineering Science, 55:4139-4147 (2000).
Koonaphapdeelert et al., "Carbon dioxide stripping in ceramic hollow fibre membrane contactors," Chemical Engineering Science, 64:1-8 (2009).
Kreulen et al., "Microporous hollow fibre membrane modules as gas-liquid contractors. Part 2. Mass transfer with chemical reaction," Journal of Membrane Science, 78(3):217-238 (1993).
International Search Report and Written Opinion for corresponding Application No. PCT/MY2021/050030 (mailed Aug. 24, 2021).
Office Action for Malaysia Application No. PI2020002080, mailed Jul. 28, 2023.
Honeywell UOP "Regeneration Section for PETRONAS CO2 Pilot Plant," Operating Manual, Amine Guard FS Unit (2014).
Rongwong et al., "Rate based modeling for CO2 absorption using Monoethanolamine solution in a hollow fiber membrane contactor," Journal of Membrane Science, 429:396-408 (2012).

Gas Processors Suppliers Association (2004) GPSA Engineering Data Book, FPS Version, vols. I & II, Sections 1-26 Hydrocarbon Treating (2004).
Shaw and Hughes, "Optimize CO2 removal," Hydrocarbon Processing, May, pp. 53-58 (May 2001).
Wang et al., "Solubility of N2O in alkanolamines and in mixed solvents," The Chem. Eng. Journal, 48:31-40 (1992).
Billet and Schultes, "(1999) Prediction of mass transfer columns with dumped and arranged packings," Trans IChemE, 77:498-504 (1999).
Hydrogen Analysis Resource Center, "Lower and Higher Heating Values of Hydrogen and Other Fuels," (2019).
Lv et al., "Wetting of polypropylene hollow fiber membrane contactors," Journal of Membrane Science. Elsevier B.V., 362(1-2):444-452 (2010).
Li et al., "Scale-up of PEEK hollow fiber membrane contactor for post-combustion CO2 capture," Journal of Membrane Science, 527:92-101 (2017).
Liebenthal et al., "Overall process analysis and optimisation for CO2 Capture from coal fired power plants based on phase change solvents forming two liquid phases," Energy Procedia. Elsevier B.V., 37:1844-1854 (2013).
Liu et al., "Mass transfer enhancement in coiled hollow fiber membrane modules," Journal of Membrane Science, 264:113-121 (2005).
Hartono et al., Solubility of N2O in aqueous solution of Diethylenetriamine, J. Chem. Eng. Data, 53:2696-2700 (2008).
Krishna and Wesselingh, The Maxwell-Stefan approach to mass transfer, Science, 52(6):861-911 (1997).
Kvamsdal and Rochelle, "Effects of the temperature bulge in CO2 absorption from flue gas by aqueous monoethanolamine," Industrial and Engineering Chemistry Research, 47(3):867-875 (2008).
Li et al., "Review of CO2 absorption using chemical solvents in hollow fiber membrane contactors," Separation and Purification Technology, 41(2):109-122 (2005).
Li, K., "Membrane Science and Membrane Separation Processes," ChE 413 Lecture notes. Department of Chemical Engineering & Chemical Technology, Imperial College London (2015).
Lu et al., "Wetting mechanism in mass transfer process of hydrophobic membrane gas absorption,", Journal of Membrane Science, 308(1-2): 180-190 (2008).
Lu et al., "Absorption of CO2 into aqueous solutions of methyldiethanolamine and activated methyldiethanolamine from a gas mixture in a hollow fiber contactor," Industrial and Engineering Chemistry Research, 44:9230-9238 (2005).
MacDowell et al., "An overview of CO2 capture technologies," Energy & Environmental Science, 3(11):1645-1669 (2010).
Malek and Teo, "Modeling of Microporous Hollow Fiber Membrane Modules operated under Partially Wetted Conditions," Industrial & Engineering Chemistry Research, 36:784-793 (1997).
Mandal et al., "Density and viscosity of aqueous solutions of (N-methyldiethanolamine + monoethanolamine), (N-methyldiethanolamine + diethanolamine), (2-amino-2-methyl-1-propanol + monoethanolamine), and (2-amino-2-methyl-1-propanol + diethanolamine)," Journal of Chemical and Engineering Data, 48(3):703-707 (2003).
Mansourizadeh and Ismail, "Hollow fiber gas-liquid membrane contactors for acid gas capture: A review," Journal of Hazardous Materials, 171:38-53 (2009).
Mavroudi et al., "A study of mass transfer resistance in membrane gas-liquid contacting processes," Journal of Membrane Science, 272(1-2): 103-115 (2006).
Moulin et al., "Mass transfer improvement by secondary flows: Dean vortices in coiled tubular membranes," Journal of Membrane Science, 114(2):235-244 (1996).
Nishikawa et al., "(1995) CO2 Removal by Hollow Fiber Gas Liquid Contactor," Energy Conversion and Management, 36(6):415-418 (1995).
Narku-Tetteh et al., "Evaluation of the Roles of Absorber and Desorber Catalysts in the Heat Duty and Heat of CO2 Desorption from Butylethanolamine-2-Amino-2-methyl-1-propanol and Monoethanolamine-Methyldiethanoamine Solvent Blends in a Bench-

(56) References Cited

OTHER PUBLICATIONS

Scale CO2 Capture Pilot Plant," Energy and Fuels. American Chemical Society, 32(9):9711-9726 (2018).
Pakšiová et al., "Modeling of carbon dioxide removal using membrane contactors," Proceedings of the 28th International Conference, 2016 Cybernetics & Informatics (K&I), Feb. 2-5, 2016, Levoca, Slovakia, pp. 1-6 (2016) doi: 10.1109/CYBERI.2016. 7438596.
Park and Sandall, "Solubility of carbon dioxide and nitrous oxide in 50 mass % methyldiethanolamine," Journal of Chemical and Engineering Data, 46(1):166-168 (2001).
Park et al., "Absorption characteristic of continuous CO2 absorption process," ACS Division of Fuel Chemistry, Preprints, 49(1):249-250 (2004).
Paul et al., "Removal of CO2 by Single and Blended Aqueous Alkanolamine Solvents in Hollow-Fiber Membrane Contactor: Modeling and Simulation," Industrial and Engineering Chemistry Research, (46):2576-2588 (2007).
Qi and Cussler, "Microporous hollow fibers for gas absorption I. Mass transfer in the liquid," Journal of Membrane Science, 23(3):321-332 (1985).
Qi and Cussler, "Microporous hollow fibers for gas absorption. II. Mass transfer across the membrane," Journal of Membrane Science, 23(3):333-345 (1985).
Rezazakazemi et al., "CFD simulation of natural gas sweetening in a gas-liquid hollow-fiber membrane contactor," Chemical Engineering Journal. Elsevier B.V., 168(3):1217-1226 (2011).
Rezazadeh et al., "Performance evaluation and optimisation of post combustion CO2 capture processes for natural gas applications at pilot scale via a verified rate-based model," International Journal of Greenhouse Gas Control. Elsevier Ltd, 53:243-253 (2016).
Sánchez et al., "Solubility of hydrocarbon in alkanolamine aqueous solution," EQUIFASE Conference, (Jan. 2009).
Dashti et al., "Sensitivity analysis for selection of an optimum amine gas sweetening process with minimum cost requirement," Asia-Pacific Journal of Chemical Engineering, 10(5):709-715 (2015).
Sohrabi et al., "Mathematical modeling and numerical simulation of CO2 transport through hollow-fiber membranes," Applied Mathematical Modelling. Elsevier Inc., 35(1):174-188 (2011).
Souza, L., "Modelling ethane absorption in MEA solution," Petrolium Technology Quarterly, Gas (2018).
Teletzke and Madhyani, "Minimise amine losses in gas and liquid treating," (2018) Available at: https://www.digitalrefining.com/article/1001504,Minimise_amine_losses_in_gas_and_liquid_treating. html#.XKMHpJgzZPY (Accessed: Jan. 3, 2019).
TransCanada (2016) "Gas Quality Specifications-TransCanada and other pipelines," Available at: http://www.tccustomerexpress.com/docs/Gas_Quality_Specifications_Fact_Sheet.pdf (Accessed: Jan. 1, 2016).
Van Swaaij and Versteeg, "(1992) Mass transfer accompanied with complex reversible chemical reactions in gas—liquid systems: an overview," Chemical Engineering Science, 47(13-14):3181-3195 (1992).
Versteeg and Van Swaaij, "Solubility and diffusivity of acid gases (CO2 and N2O) in aqueous alkanilamine solutions," J. Chem. Eng. Data, 33:29-34 (1988).
Wang et al., "Porous PVDF asymmetric hollow fiber membranes prepared with the use of small molecular additives," Journal of Membrane Science, 178(1-2):13-23 (2000).

Wank and Cussler, "Baffled membrane modules made with hollow fiber fabric," Journal of Membrane Science, 85(3):265-278 (1993).
Wang et al., "Post-combustion CO2 capture with chemical absorption: A state-of-the-art review," Chemical Engineering Research and Design. Institution of Chemical Engineers, 89(9):1609-1624 (2011).
Wang et al., "Impact of DEA solutions with and without CO2 loading on porous polypropylene membranes intended for use as contactors," Journal of Membrane Science, 229(1-2):147-157 (2004).
Wang et al., "Influence of membrane wetting on CO2 capture in microporous hollow fiber membrane contactors," Separation and Purification Technology, 46(1-2):33-40 (2005).
Wang et al., "Optimization of blended amines for CO2 absorption in a hollow-fiber membrane contactor," Industrial and Engineering Chemistry Research, 52(34):12170-12182 (2013).
Wang et al., "Experimental and Modeling Study of Trace CO2 Removal in a Hollow-Fiber Membrane Contactor, Using CO2-Loaded Monoethanolamine," Industrial & Engineering Chemistry Research, 52:18059-18070 (2013).
Weiland et al., "Heat Capacity of Aqueous Monoethanolamine , Diethanolamine , N-Methyldiethanolamine , and N-Methyldiethanolamine-Based Blends with Carbon Dioxide," Journal of Chemical & Engineering Data, 42(5):1004-1006 (1997).
Wickramasinghe et al., "Mass transfer in various hollow fiber geometries," Journal of Membrane Science, 69(3):235-250 (1992).
Xu et al., "(2016) Experimental Study of Regeneration Performance of Aqueous N,N-Diethylethanolamine Solution in a Column Packed with Dixon Ring Random Packing," Ind. Eng. Chem. Res.55:8519-8526 (2016).
Yeow et al., Morphological study of poly(vinylidene fluoride) asymmetric membranes: Effects of the solvent, additive, and dope temperature, Journal of Applied Polymer Science, 92(3):1782-1789 (2004).
Zhang and Wang, "Gas-liquid membrane contactors for acid gas removal: Recent advances and future challenges," Current Opinion in Chemical Engineering. Elsevier Ltd, 2(2):255-262 (2003).
Zhang et al., "Theoretical and experimental studies of membrane wetting in the membrane gas-liquid contacting process for CO2 absorption," Journal of Membrane Science, 308(1-2):162-170 (2008).
Zydney et al., Use of the log-normal probability density function to analyze membrane pore size distributions: Functional forms and discrepancies, Journal of Membrane Science, 91(3):293-298 (1994).
Quek et al., Modeling for Design and Operation of high-pressure membrane contactors in natural gas sweetening—Chemical Engineering Research and Design 132:1005-1019 (2018).
Eia, "International Energy Outlook 2016," (May 2016).
Engineering ToolBox, "Fuels—Higher and Lower Calorific Values," (2003).
Engineering ToolBox, "Water—Heat of Vaporization," (2010).
Boucif et al., "Carbon Dioxide Absorption by Monoethanolamine in Hollow Fiber Membrane Contactors: A Parametric Investigation," AIChE Journal, 58(9):2843-2855 (2012).
Drioli et al., "Membrane Contactors: Fundamentals, Applications and Potentialities☐; Chapter 2 . Membrane materials," Elsevier Science, pp. 40-104 (2005).
First Office Action and Search Report in corresponding China Application No. 202180030534.7, mailed May 29, 2025 (with English Translation).
First Office Action and Search Report in corresponding Korea Application No. 202180030534.7, mailed May 29, 2025 (with English Translation).

* cited by examiner

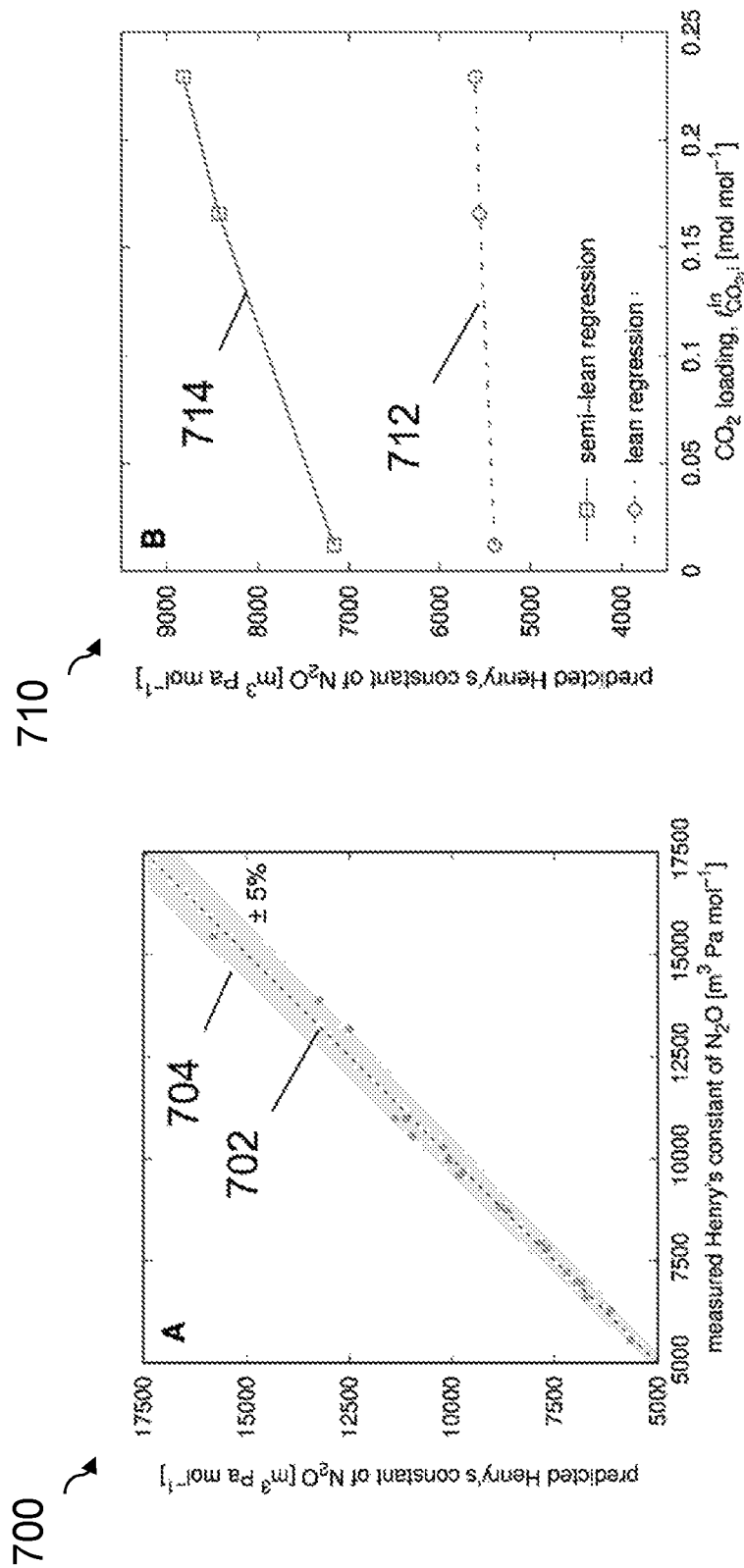

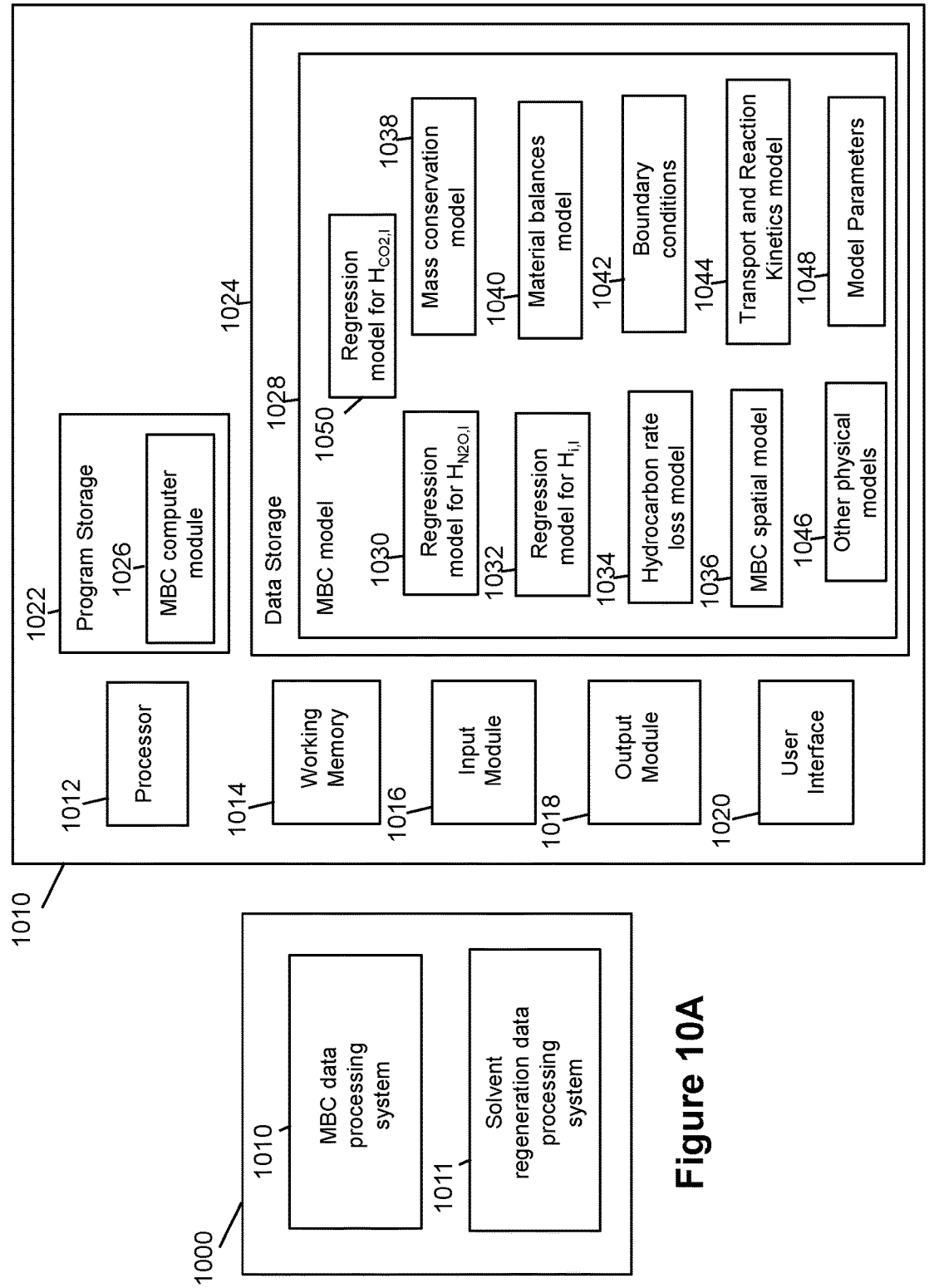

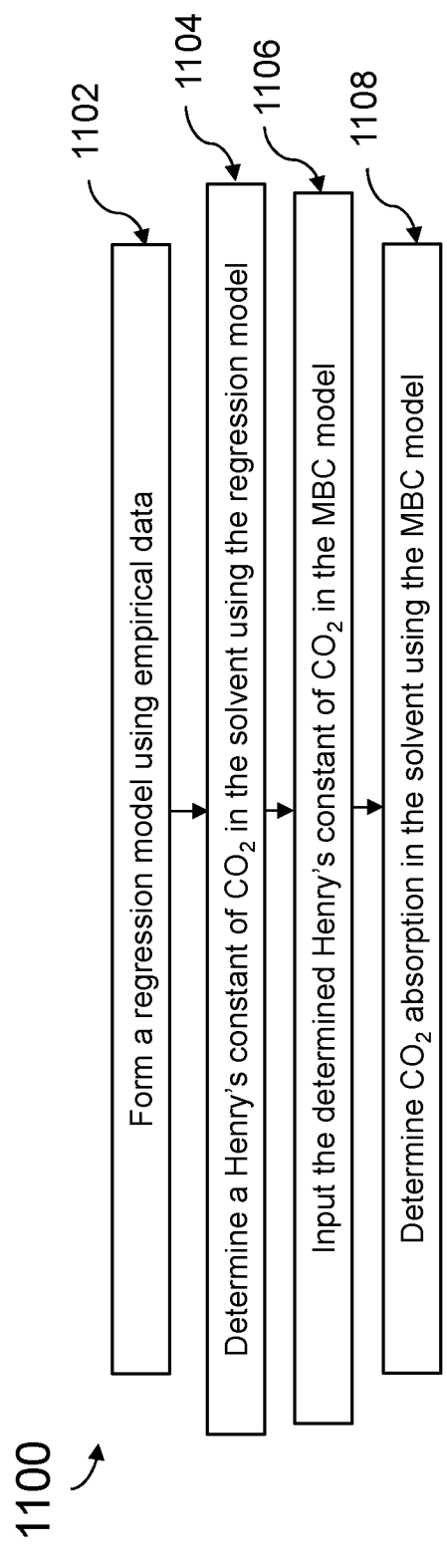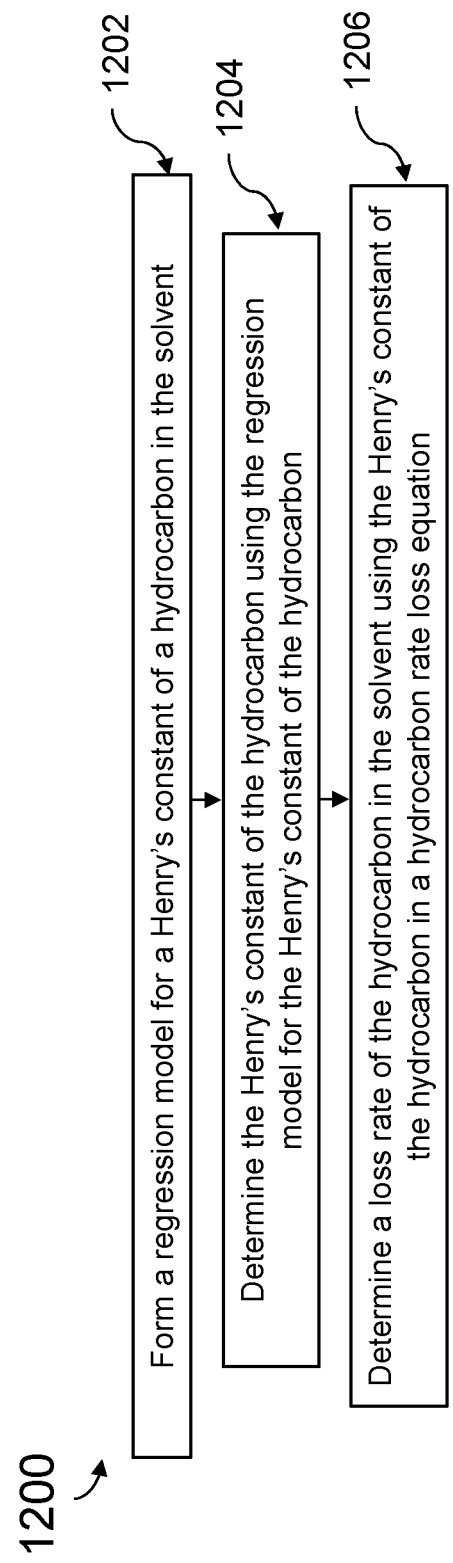
Figure 11
Figure 12

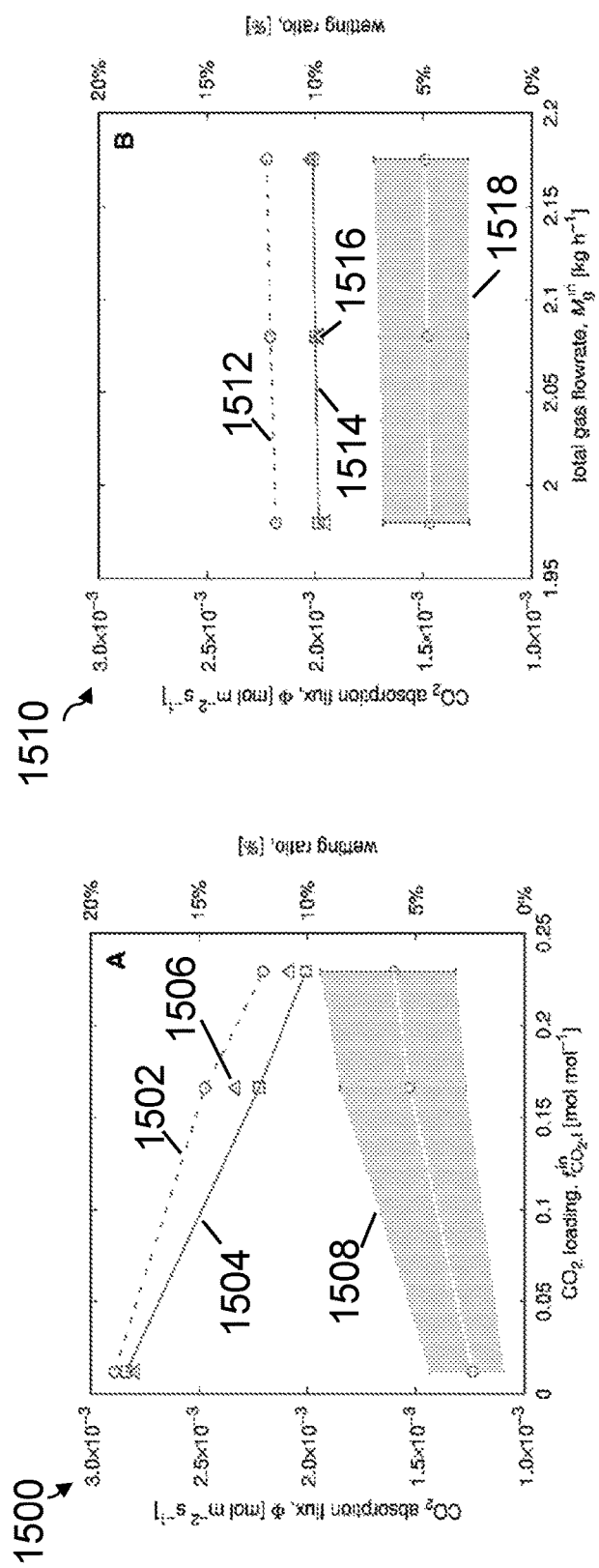
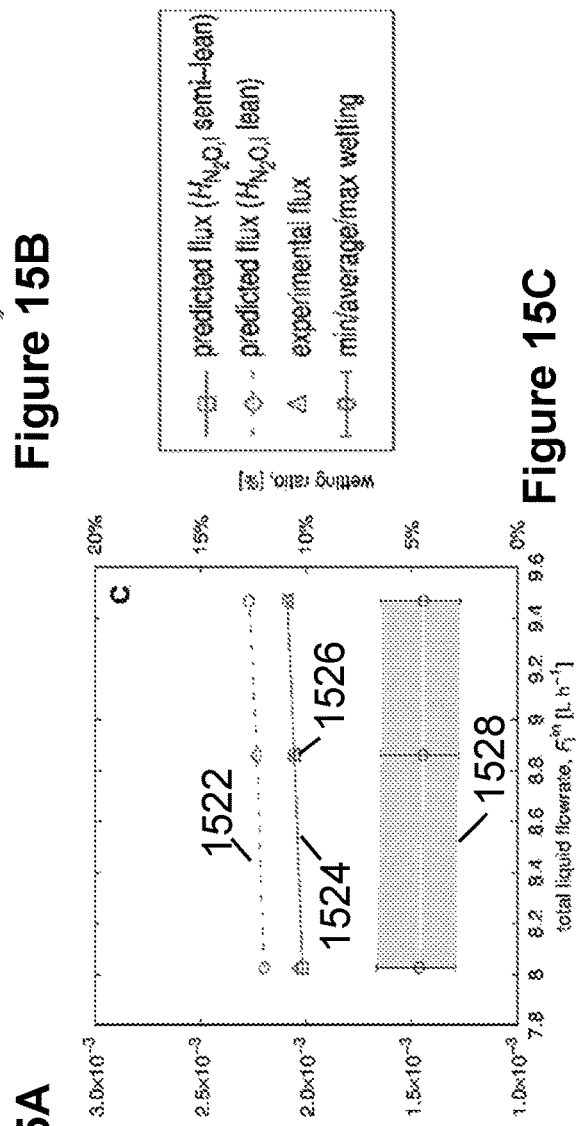
Figure 15A
Figure 15B
Figure 15C

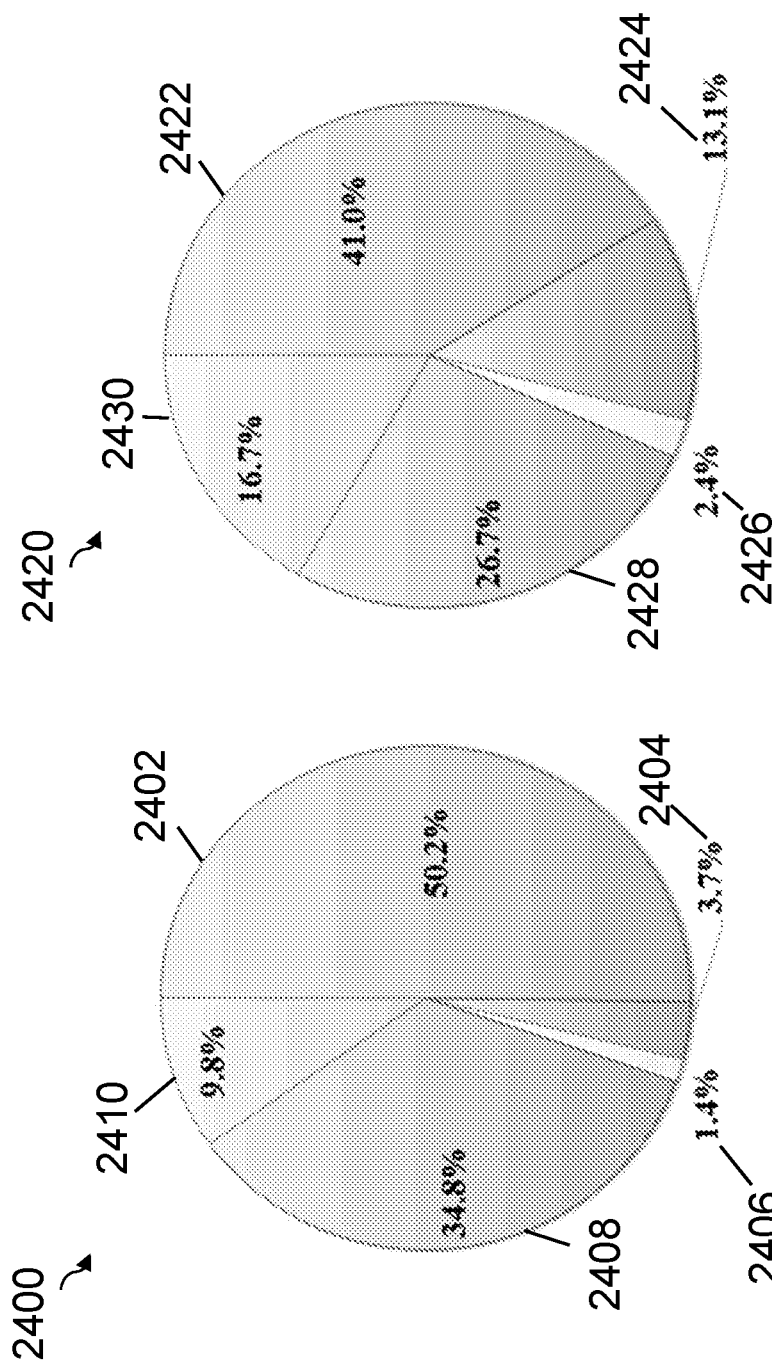

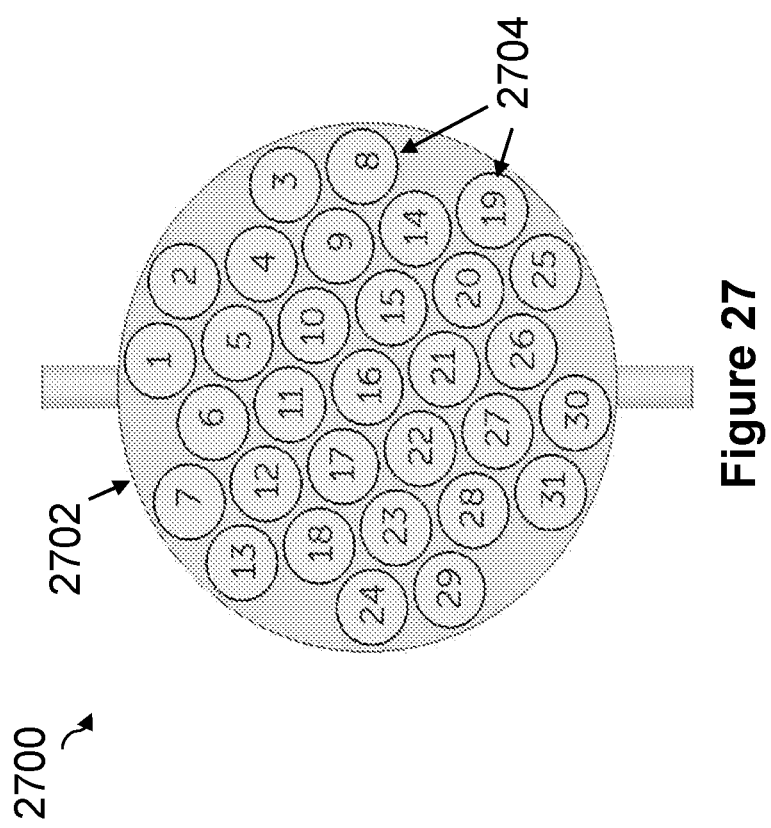

METHOD AND SYSTEM FOR DESIGNING AND ASSESSING THE PERFORMANCE OF A HOLLOW FIBRE MEMBRANE CONTACTOR (MBC) IN A NATURAL GAS SWEETENING PROCESS

This application is a national stage application under 35 U.S.C. 371 of PCT/MY2021/050030, filed Apr. 21, 2021, which claims the priority benefit of Malaysia Patent Application No. PI 2020002080, filed Apr. 24, 2020, each of which is incorporated herein by reference in its entirety.

TECHNICAL FIELD

The present disclosure relates to method and system for designing and assessing the performance of a hollow fibre membrane contactor (MBC) in a natural gas sweetening process, in particular, by using a MBC model.

BACKGROUND

Natural gas (NG) is presently the third most-utilised form of fossil fuel energy and is widely used for both electricity production and transportation. NG comprises a mixture of combustible hydrocarbon gases (typically methane ($CH_4$), ethane ($C_2H_6$), propane ($C_3H_8$), butane ($C_4H_{10}$) and pentane ($C_5H_{12}$)) and impurities (for example, carbon dioxide ($CO_2$)). Removal of $CO_2$ from NG is important for various reasons—(i) to meet a sales gas specification for NG which typically imposes a $CO_2$ content lower than 2-3%, (ii) to avoid freezing in low-temperature chillers, (iii) to avoid catalyst poisoning in ammonia plants, (iv) to reduce the risk of corrosion in process equipment and pipeline, (v) to reduce the heating value of NG, and (vi) to meet the specification of <50 ppmv in liquefied natural gas plants for avoiding freezing in low-temperature chillers.

Over the past decade, membrane contactors (MBC) for $CO_2$ absorption have been widely recognised for their large intensification potential compared to conventional absorption towers. MBC technology uses microporous hollow-fibre membranes (HFM) to enable effective gas and liquid mass transfer without the two phases dispersing into each other. Their packaging into HFM modules offers a higher mass transfer area compared with conventional packed columns which in turn gives MBC a high intensification potential. This modularity also empowers a more flexible design and scale-up.

Mathematical models provide an effective tool to help understand the $CO_2$ removal mechanisms in MBC, and thus enable a better assessment and optimisation of their performance. However, most models to date are deficient and have not considered various factors or effects which may affect among other things an accuracy of a simulated output (such as $CO_2$ absorption rate) of the MBC. Further, most of the commercial process simulators do not include models or tools which are associated with the use of HFM in the MBC technology. The lack of HFM mathematical tools has posed problems for the end user to design and optimise the HFM system, in particular, for use in a natural gas sweetening process.

It is therefore desirable to provide method and system for assessing a performance of a hollow fibre membrane contactor (MBC) in a natural gas sweetening process using a MBC model which take into account various factors and effects in the MBC so as to address the aforementioned problems and/or provides the public with a useful alternative.

Furthermore, other desirable features and characteristics will become apparent from the subsequent detailed description and the appended claims, taken in conjunction with the accompanying drawings and this background of the disclosure.

SUMMARY

Aspects of the present application relate to method and system for designing and assessing the performance of hollow fibre membrane contactor (MBC) in a natural gas sweetening process using a MBC model.

In accordance with a first aspect, there is provided a computer-implemented method for designing and assessing the performance of a hollow fibre membrane contactor (MBC) in a natural gas sweetening process using a MBC model. The MBC model comprises model parameters, model equations and boundary conditions for calculating data associated with the natural gas sweetening process, and the natural gas sweetening process comprises removal of acid gas from natural gas using a solvent comprising at least one component. The method comprising: (i) forming a regression model using empirical data; (ii) determining a Henry's constant of $CO_2$ in the solvent using the regression model; (iii) inputting the determined Henry's constant of $CO_2$ in the MBC model as one of the model parameters; and (iv) determining $CO_2$ absorption in the solvent using the MBC model for designing and assessing the performance of the MBC.

By forming a regression model using empirical data, a Henry's constant of $CO_2$ in the solvent can be determined which advantageously accounts for $CO_2$ loading in the solvent. This is important as $CO_2$ loading in the solvent affects the absorption rate of $CO_2$ in the solvent which in turn affects a performance of the MBC. Moreover, the regression model is formed using empirical data, thereby improving an accuracy of the model predictions, for example, as compared to using only analytical equations. Further, by not using a multitude of analytical equations which would otherwise be required to simulate the Henry's constant of $CO_2$, the aforementioned method shortens the simulation time required for determining $CO_2$ absorption in the solvent using the MBC model for designing and assessing the performance of the MBC. The regression model may be formed for a Henry's constant of $CO_2$ using empirical data associated with $CO_2$ solubility in the solvent. In an embodiment, the regression model may be formed for a Henry's constant of nitrous oxide as described below.

The method may comprise: forming a regression model for a Henry's constant of nitrous oxide ($N_2O$) using empirical data of $N_2O$ solubility in the solvent; determining the Henry's constant of $N_2O$ using the regression model for the Henry's constant of $N_2O$; and determining the Henry's constant of $CO_2$ in the solvent using the Henry's constant of $N_2O$ to account for $CO_2$ loading in the solvent. $N_2O$ is chosen because $N_2O$ has similar properties to $CO_2$ and is not reactive to the solvent. Experiments conducted to obtain $N_2O$ solubility in solvents are therefore simple and their data reliable.

The method may comprise: forming a regression model for a Henry's constant of a hydrocarbon in the solvent using empirical data of the hydrocarbon solubility in the solvent to account for hydrocarbon loss from the natural gas to the solvent; and determining the Henry's constant of the hydrocarbon in the solvent using the regression model for the Henry's constant of the hydrocarbon.

Similar to the above, since the regression model for a Henry's constant of a hydrocarbon is formed using empirical data, an accuracy of the model predictions is thereby improved. Further, by not using a multitude of analytical equations which would otherwise be required to simulate the Henry's constant of a hydrocarbon, the aforementioned method improves the simulation time required for determining the Henry's constant of a hydrocarbon which is in turn used in determining a loss rate of the hydrocarbon as described below.

The method may comprise determining a loss rate of the hydrocarbon in the solvent using the Henry's constant of the hydrocarbon in a hydrocarbon rate loss equation, wherein the loss rate of the hydrocarbon is a function of a concentration of the hydrocarbon, and wherein the concentration of the hydrocarbon is inversely proportional to the Henry's constant of the hydrocarbon in the solvent. By considering a loss rate of the hydrocarbon in the solvent, the aforementioned method advantageously takes into account a problem of the physical absorption of the hydrocarbons from NG into the solvent (e.g. an amine solvent), which is significant (increase by 10-30 folds when compared to near atmospheric pressure) when the pressure increases to 60 bar. Further, any hydrocarbon (HC) absorbed by the solvent that is not recovered will end up in the waste acid gas stream and therefore represents product loss, and the presence of hydrocarbons in the acid gas stream also cause problems downstream of the MBC process, such as catalyst fouling in Clause reactors. By having an effective method to simulate the loss rate of the hydrocarbons, various parameters of the natural gas sweetening process can be adjusted to minimise product loss and to mitigate problems such as catalyst fouling as mentioned above.

The method may comprise including the hydrocarbon rate loss equation as one of the model equations of the MBC model.

The method may comprise: determining a molar fraction of the at least one component of the solvent in the gas outlet using Raoult's Law; and determining a solvent loss rate using the molar fraction in a solvent rate loss equation, wherein the solvent loss rate is proportional to the determined molar fraction. By determining a molar fraction of the at least one component of the solvent in the gas outlet, a solvent loss rate can be determined. This advantageously accounts for an effect of solvent evaporation on the MBC process performance. In practice, the gradual loss of solvent to the treated gas in the MBC can change the $CO_2$ absorption rate. Moreover, the amount of water evaporated from the solvent leads to a temperature drop of the solvent. Such a drop in the solvent temperature might affect the mass transfer performance in the MBC. For example, important factors like the $CO_2$ capture capacity and the corrosion rate directly depend on the temperature of the MBC column.

The method may comprise including the solvent rate loss equation as one of the model equations of the MBC model.

The method may comprise determining an energy consumed for solvent evaporation and a liquid temperature of the solvent at a liquid inlet of the MBC using the solvent loss rate.

The method may comprise determining a change in the liquid temperature by balancing the energy consumed for solvent evaporation with an exothermic $CO_2$ absorption reaction under adiabatic conditions along the length of the MBC. As discussed above, by determining a change in the liquid temperature, a mass transfer performance in the MBC may be assessed. Other important factors which determine a performance of the MBC, such as $CO_2$ capture capacity, may also be dependent on the temperature of the MBC column.

In accordance with a second aspect, a computer-implemented method for assessing a performance of the natural gas sweetening process is described. The natural gas sweetening process comprises absorption operations and desorption operations, wherein the absorption operations are associated with acid gas absorption using the hollow fibre membrane contactor (MBC) and the desorption operations are associated with solvent regeneration using a solvent regenerator, and wherein the absorption operations are modelled based on the MBC model using the aforementioned computer-implemented methods.

The method for assessing a performance of the natural gas sweetening process may comprise: calculating an optimised flowrate associated with each of a lean operation and a semi-lean operation for achieving a predetermined $CO_2$ purity in the natural gas, the lean operation being an operation associated with using a lean solvent having less than 0.02 mol mol$^{-1}$ of $CO_2$ loading and the semi-lean operation being an operation associated with using a semi-lean solvent having more than 0.2 mol mol$^{-1}$ of $CO_2$ loading; and determining a total process duty for the natural gas sweetening process associated with the absorption operations and the desorption operations under the lean operation and semi-lean operation.

The method for assessing a performance of the natural gas sweetening process may comprise: calculating a pressure for operating a rich solution flash drum associated with each of the lean operation and the semi-lean operation for achieving a predetermined lower heating value of a fuel gas, the fuel gas being a gas recovered from hydrocarbons loss in the solvent during the natural gas sweetening process.

In accordance with a third aspect, there is provided a computer-implemented method for designing and assessing a performance of a hollow fibre membrane contactor (MBC) in a natural gas sweetening process using a MBC model, wherein the MBC model comprises model parameters, model equations and boundary conditions for calculating data associated with the natural gas sweetening process and the natural gas sweetening process comprises removal of acid gas from natural gas using a solvent comprising at least one component, the method comprising: (i) forming a regression model for a Henry's constant of hydrocarbon in the solvent using empirical data of the hydrocarbon solubility in the solvent to account for hydrocarbon loss from the natural gas to the solvent, wherein the regression model is a function of a temperature of the solvent, a pressure of the solvent and a mass fraction of the at least one component in the solvent; (ii) determining the Henry's constant of the hydrocarbon in the solvent; (iii) determining a loss rate of the hydrocarbon in the solvent using the Henry's constant of the hydrocarbon in a hydrocarbon rate loss equation to account for hydrocarbon loss from the natural gas to the solvent, wherein the loss rate of the hydrocarbon is a function of the concentration of the hydrocarbon, and wherein the concentration of the hydrocarbon is inversely proportional to the Henry's constant of the hydrocarbon; and (iv) determining $CO_2$ absorption in the solvent using the MBC model for designing and assessing the performance of the hollow fibre membrane contactor, wherein the hydrocarbon rate loss equation is included as one of the model equations of the MBC model.

In accordance with a fourth aspect, there is provided a computer readable medium storing processor executable instructions which when executed on a processor cause the processor to carry out a method as described above.

In accordance with a fifth aspect, there is provided a hollow fibre membrane contactor (MBC) data processing system for designing and assessing a performance of a hollow fibre membrane contactor (MBC) in a natural gas sweetening process using a MBC model. The MBC model comprises model parameters, model equations and boundary conditions for calculating data associated with the natural gas sweetening process and the natural gas sweetening process comprises removal of acid gas from natural gas using a solvent comprising at least one component. The MBC data processing system comprising a processor and a data storage device storing computer program instructions operable to cause the processor to: form a regression model using empirical data; determine a Henry's constant of $CO_2$ in the solvent using the regression model; input the determined Henry's constant of $CO_2$ in the MBC model as one of the model parameters; and determine $CO_2$ absorption in the solvent using the MBC model for designing and assessing the performance of the MBC.

The data storage device of the MBC data processing system may store computer program instructions operable to cause the processor to: form a regression model for a Henry's constant of nitrous oxide ($N_2O$) using empirical data of $N_2O$ solubility in the solvent; determine the Henry's constant of $N_2O$ using the regression model for the Henry's constant of $N_2O$; and determine the Henry's constant of $CO_2$ in the solvent using the Henry's constant of $N_2O$ to account for $CO_2$ loading in the solvent.

The regression model for the Henry's constant of nitrous oxide ($N_2O$) may be a function of $CO_2$ loading and the liquid temperature of the solvent.

The data storage device of the MBC data processing system may store computer program instructions operable to cause the processor to: form a regression model for a Henry's constant of hydrocarbon in the solvent using empirical data of the hydrocarbon solubility in the solvent to account for hydrocarbon loss from the natural gas to the solvent; and determine the Henry's constant of the hydrocarbon in the solvent using the regression model for the Henry's constant of the hydrocarbon.

The regression model for the Henry's constant of hydrocarbon may be a function of the liquid temperature of the solvent, a liquid pressure of the solvent and a mass fraction of at least one component in the solvent.

The data storage device of the MBC data processing system may store computer program instructions operable to cause the processor to: determine a loss rate of the hydrocarbon in the solvent using the Henry's constant of the hydrocarbon in a hydrocarbon rate loss equation, wherein the loss rate of the hydrocarbon is a function of the concentration of the hydrocarbon, and wherein the concentration of the hydrocarbon is inversely proportional to the Henry's constant of the hydrocarbon.

The data storage device of the MBC data processing system may store computer program instructions operable to cause the processor to include the hydrocarbon rate loss equation as one of the model equations of the MBC model.

The solvent may be taken to be saturated with hydrocarbons at a liquid outlet of the MBC.

The data storage device of the MBC data processing system may store computer program instructions operable to cause the processor to: determine a molar fraction of the at least one component of the solvent in the gas outlet using Raoult's Law; and determine a solvent loss rate using the molar fraction in a solvent rate loss equation, wherein the solvent loss rate is proportional to the determined molar fraction.

Treated gas at a gas outlet of the MBC may be taken to be saturated with the solvent, and the natural gas and the solvent may be taken to be at equilibrium at the gas outlet.

The data storage device of the MBC data processing system may store computer program instructions operable to cause the processor to include the solvent rate loss equation as one of the model equations of the MBC model.

The data storage device of the MBC data processing system may store computer program instructions operable to cause the processor to determine an energy consumed for solvent evaporation and the liquid temperature of the solvent at a liquid inlet of the MBC using the solvent loss rate.

Solvent evaporation may be taken to occur at the liquid inlet before the solvent reacts with the $CO_2$ in the natural gas along a length of the MBC.

The data storage device of the MBC data processing system may store computer program instructions operable to cause the processor to: determine a change in the liquid temperature by balancing the energy consumed for solvent evaporation with an exothermic $CO_2$ absorption reaction under adiabatic conditions along the length of the MBC.

Thermal diffusion along a radial axis may be neglected and the liquid temperature may be taken to be homogenous in the radial direction.

Where the solvent comprises 50% methyldiethanolamine (MDEA) by weight, the regression model for the Henry's constant of nitrous oxide ($N_2O$) may be modelled as $$H_{N_2O,l} = -3.30 \times 10^4 - 3.79 \times 10^4 f_{CO_2,l}{}^{in} + 1.70 \times 10^2 T_l - 4.37 \times 10^3 (f_{CO_2,l}{}^{in})^2 - 1.34 \times 10^{-1} T_l^2 + 1.45 \times 10^2 f_{CO_2,l}{}^{in} T_l$$

where $f_{CO_2,l}{}^{in}$ is associated with an inlet $CO_2$ loading in the solvent and $T_l$ is the liquid temperature of the solvent.

The regression model for the Henry's constant of hydrocarbon may be modelled as $$H_{i,l} = \alpha_0 + \alpha_1 C + \alpha_2 T_l + \alpha_3 P_l + \alpha_4 C T_l + \alpha_5 C P_l + \alpha_6 T_l P_l$$

where $T_l$ is the liquid temperature of the solvent, $P_l$ is the liquid pressure of the solvent, C is the mass fraction of the at least one component in the solvent, and the coefficients $\alpha_1$ to $\alpha_6$ are parameters of the regression model for the Henry's constant of hydrocarbon.

According to a sixth aspect, a natural gas sweetening process operating system is described. The natural gas sweetening process operating system comprises the aforementioned MBC data processing system and a solvent regeneration data processing system, the MBC data processing system is associated with absorption operations for acid gas absorption using the hollow fibre membrane contactor (MBC) and the solvent regeneration data processing system is associated with desorption operations for solvent regeneration using a solvent regenerator.

The natural gas sweetening process operating system may comprise a processor and a data storage device storing computer program instructions operable to cause the processor to: calculate an optimised flowrate associated with each of a lean operation and a semi-lean operation for achieving a predetermined $CO_2$ purity in the natural gas, the lean operation being an operation associated with using a lean solvent having less than 0.02 mol mol$^{-1}$ of $CO_2$ loading and the semi-lean operation being an operation associated with using a semi-lean solvent having more than 0.2 mol mol$^{-1}$ of $CO_2$ loading; and determine a total process duty for the natural gas sweetening process associated with the absorption operations and the desorption operations under the lean operation and semi-lean operation.

The data storage device of the natural gas sweetening process operating system may store computer program instructions operable to cause the processor to: calculate a pressure for operating a rich solution flash drum associated with each of the lean operation and the semi-lean operation for achieving a predetermined lower heating value of a fuel gas, the fuel gas being gas recovered from hydrocarbons loss in the solvent during the natural gas sweetening process.

It should be appreciated that features relating to one aspect may be applicable to the other aspects. Embodiments therefore provide method and system for designing and assessing a performance of a hollow fibre membrane contactor (MBC) in a natural gas sweetening process using a MBC model. By forming a regression model using empirical data, a Henry's constant of $CO_2$ can be determined which advantageously accounts for $CO_2$ loading in the solvent. The regression model is formed based on empirical data, thereby improving an accuracy of the model predictions. Further, by not using a multitude of analytical equations which would otherwise be required to simulate the Henry's constant of $CO_2$, the aforementioned method improves the simulation time required for determining $CO_2$ absorption in the solvent using the MBC model for assessing the performance of the MBC. Embodiments may further provide a regression model for a Henry's constant of a hydrocarbon formed using empirical data, this improves an accuracy of the model predictions. Further, by not using a multitude of analytical equations which would otherwise be required to simulate the Henry's constant of a hydrocarbon, embodiments also improve the simulation time required for determining a loss rate of the hydrocarbon as described. In turn, by considering a loss rate of the hydrocarbon in the solvent, the embodiments advantageously take into account a problem of the physical absorption of the hydrocarbons from NG into the amine solvent, which is significant when the pressure in the MBC increases to, for example, 60 bar.

BRIEF DESCRIPTION OF THE DRAWINGS

Embodiments will now be described, by way of example only, with reference to the following drawings, in which:

FIG. 1A shows a schematic demonstrating cylindrical approximation around each fibre of the MBC and FIG. 1B shows a schematic of a single piece of hollow fibre of the MBC demonstrating the counter-current flow of gas and solvent in the MBC, in accordance with an embodiment;

FIG. 5A shows a graph of the required outer radius of the steel tube insert and predicted total number of fibres in the MBC module for different membrane areas in order to maintain a packing density of 0.55, and FIG. 5B shows a graph of predicted $CO_2$ absorption flux and $CO_2$ outlet gas purity for different membrane areas;

FIG. 6A shows a graph of predicted and measured Henry's constant for methane ($CH_4$), FIG. 6B shows a graph of predicted and measured Henry's constant for ethane ($C_2H_6$) and FIG. 6C shows a graph of predicted and measured Henry's constant for propane ($C_3H_8$);

FIGS. 7A and 7B show graphs of predicted Henry's constant of nitrous oxide ($N_2O$) in accordance with an embodiment, where FIG. 7A shows a graph comparing experimental data of the Henry's constant of $N_2O$ with predicted Henry's constant of $N_2O$, and FIG. 7B shows a graph of predicted Henry's constant of $N_2O$ at various $CO_2$ loading for lean amine and semi-lean amine operation;

FIGS. 10A, 10B and 10C shows block diagrams of a natural gas sweetening process operating system, a hollow fibre membrane contactor (MBC) data processing system, and a solvent regeneration data processing system respectively, in accordance with an embodiment;

FIG. 11 is a flowchart showing a method for designing and assessing a performance of a hollow fibre membrane contactor (MBC) in a natural gas sweetening process using a MBC model comprised in the system of FIG. 10B in accordance with an embodiment;

FIG. 12 is a flowchart showing steps of a method for determining a loss rate of hydrocarbons in a solvent of the MBC in accordance with an embodiment;

FIGS. 15A, 15B, 15C, 15D and 15E show graphs of predicted $CO_2$ absorption fluxes against experimental data for a lab-scale MBC set-up (FIGS. 15A-15C) and for a pilot NG plant set-up (FIGS. 15D and 15E) in accordance with an embodiment, where FIG. 15A shows a graph of $CO_2$ absorption fluxes and predicted wetting ratio for different $CO_2$ loading for the lab-scale MBC set-up, FIG. 15B shows a graph of $CO_2$ absorption fluxes and predicted wetting ratio for different total gas flowrate for the lab-scale MBC set-up, FIG. 15C shows a graph of $CO_2$ absorption fluxes and predicted wetting ratio for different total liquid flowrate for the lab-scale MBC set-up, FIG. 15D shows a graph of $CO_2$ absorption fluxes and predicted wetting ratio for different $CO_2$ loading for the pilot NG plant set-up and FIG. 15E shows a graph of $CO_2$ absorption fluxes and predicted wetting ratio for different $CO_2$ inlet concentration in natural gas mixture for the pilot NG plant set-up;

FIG. 21A shows a graph of predicted and experimental $CO_2$ purity and $CO_2$ removal efficiency for different $CO_2$ loadings in the amine solvent and FIG. 21B shows a graph of predicted and experimental total process duty for different $CO_2$ loadings in the amine solvent;

FIG. 22A shows a graph of predicted and experimental $CO_2$ absorption fluxes for different solvent regeneration temperatures and FIG. 22B shows a graph of predicted and experimental $CO_2$ loadings for different solvent regeneration temperatures;

FIGS. 24A and 24B show pie charts of a breakdown of the equipment process duty in accordance with an embodiment, where FIG. 24A shows a pie chart of a breakdown of the equipment process duty for lean amine operation and FIG. 24B shows a pie chart of a breakdown of the equipment process duty for semi-lean amine operation;

FIG. 25A shows a graph of predicted hydrocarbon recovery and LHV of the natural gas against rich-solution drum pressure under lean amine operation and FIG. 25B shows a graph of predicted hydrocarbon recovery and LHV of the natural gas against rich-solution drum pressure under semi-lean amine operation;

FIG. 26A shows a graph of evaporative loss of water, MDEA and PZ at different solvent temperatures and FIG. 26B shows a graph of the ratio of evaporative loss in acid gas to loss in treated gas for water and MDEA+PZ at different solvent temperatures; and FIG. 27 shows a schematic of a cross-section of a commercial MBC module in accordance with an embodiment.

DETAILED DESCRIPTION

The present disclosure relates to the use of method and system for designing and assessing a performance of a hollow fibre membrane contactor (MBC) in a natural gas sweetening process using a MBC model. The MBC model comprises model parameters, model equations and boundary conditions for calculating data associated with the natural gas sweetening process, and the natural gas sweetening process comprises removal of acid gas from natural gas using a solvent comprising at least one component. The solvent may comprise water, methylethanolamine (MEA), diethanolamine (DEA), methyldiethanolamine (MDEA), and/or piperazine (PZ). The solvent can also be termed an amine solvent, which will be used interchangeably in the description below.

In developing a NG plant-wide model for an MBC-based process for NG sweetening, solvent evaporation rate, mass and energy balance, hydrocarbon solubility in amine solvent and $CO_2$ loading in the amine solvent has to be accounted for. The MBC model of the present disclosure for high-pressure MBC is formulated and verified experimentally as described below in relation to FIGS. 1 to 18, and is shown to be integrated into a complete process model describing both $CO_2$ absorption and desorption operations in a full-scale MBC process for NG sweetening in relation to FIGS. 19 to 27. Although the MBC model has been applied for high pressure conditions (e.g. more than 5 bar), it may also be applicable in low pressure conditions. For example, the MBC model can be used for carbon capture from flue gas at atmospheric pressure (e.g. 1 bar).

Figures 1A, 1B:
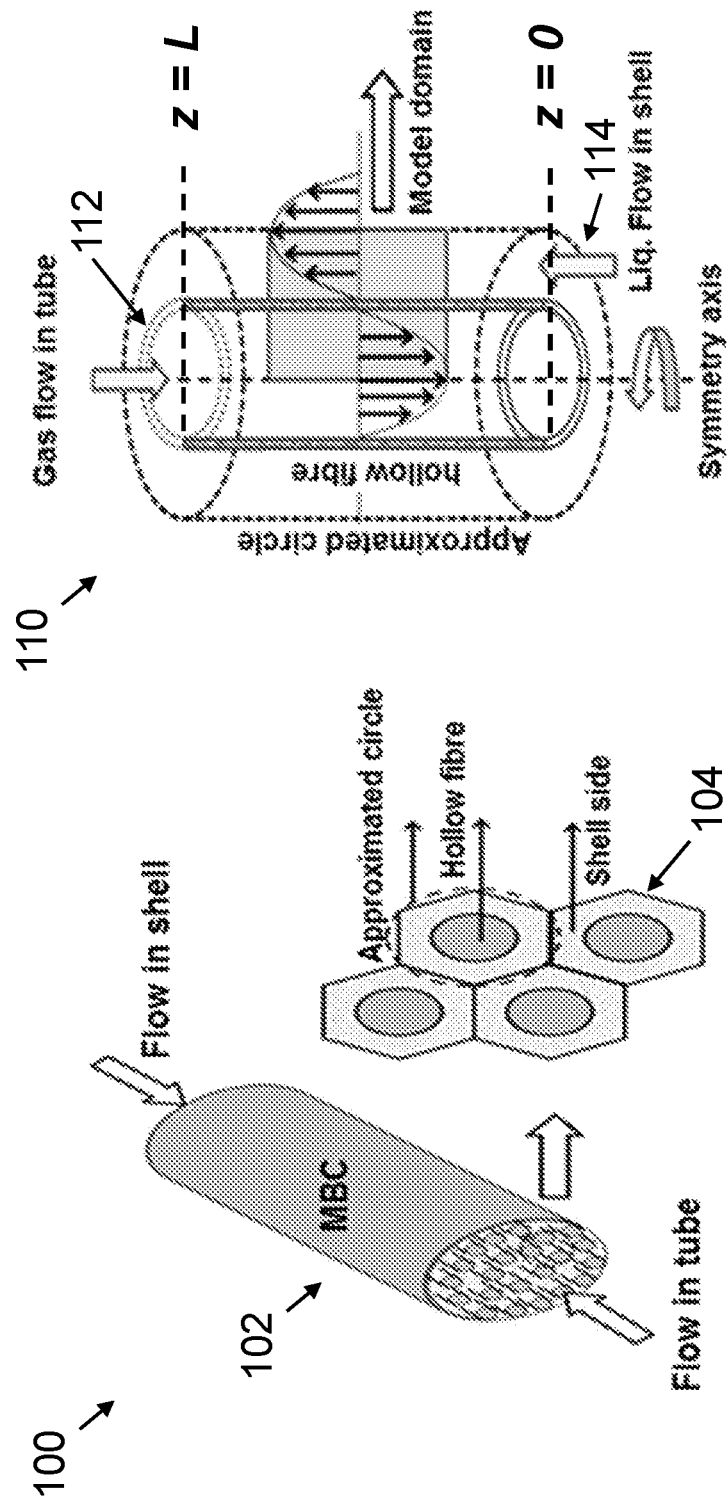
FIGS. 1A and 1B show schematics of a modelling framework for a counter-current, hollow fibre MBC module, where

FIGS. 1A and 1B show schematics 100, 110 of a modelling framework for a counter-current, hollow fibre MBC module in accordance with an embodiment, where FIG. 1A shows a schematic 100 demonstrating cylindrical approximation around each fibre of the MBC and FIG. 1B shows a schematic 110 of a single piece of hollow fibre of the MBC demonstrating the counter-current flow of gas and solvent in the MBC.

As shown in FIG. 1A, the hollow-fibre MBC module 102 comprises a number of hollow fibres 104. The hollow fibres 104 are packed in close proximity and each of their outer shell is approximated using a circle as shown. As shown in FIG. 1B, the NG gas mixture containing $CO_2$ flows in a tube through the hollow fibre 104 via a gas inlet 112 at $z=L$, while the solvent flows inside the shell of the hollow fibre 104 via a liquid/solvent inlet 114 at $z=0$, in a counter-current configuration. The gas mixture diffuses from the tube side through the walls of the hollow fibre 104 into the shell, where $CO_2$ is chemically absorbed by the solvent to enhance the removal rate.

Figure 2:
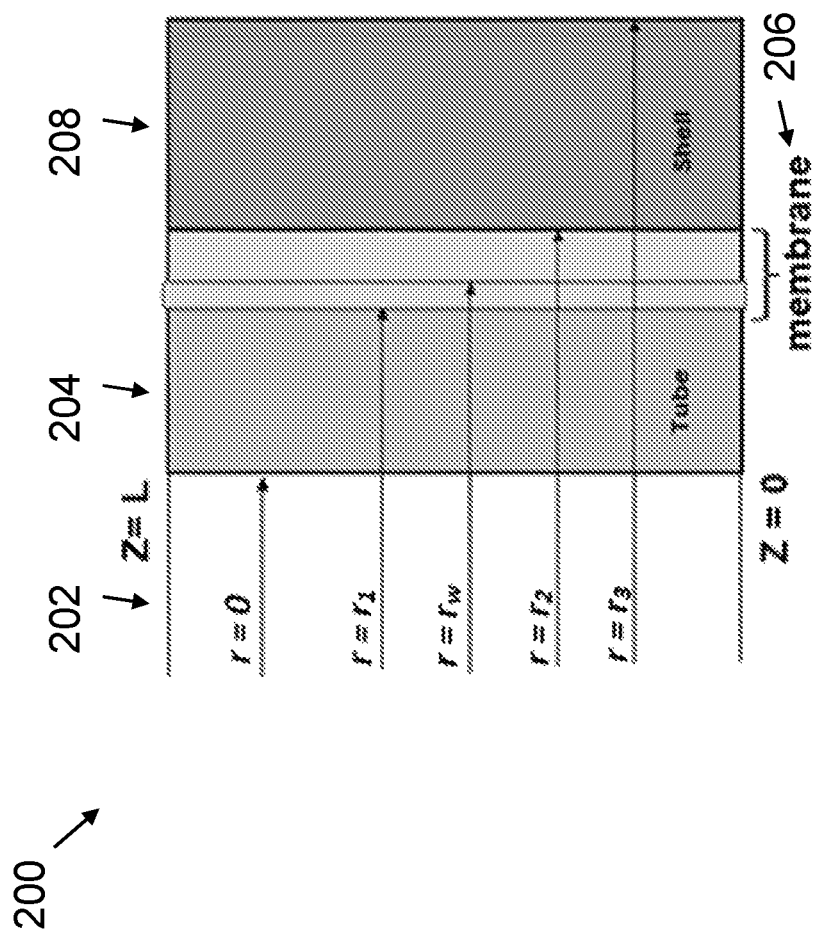
FIG. 2 shows a schematic of spatial domains used in modelling the MBC in accordance with an embodiment.

FIG. 2 shows a schematic 200 of spatial domains used in modelling the MBC in accordance with an embodiment. The schematic 200 shows a half cross-section of the hollow fibre membrane (HFM) comprising the hollow 202 through which natural gas mixtures flow through, a tube 204 of the HFM, a membrane 206 of the HFM and a shell 208 of the HFM through which the solvent flows in a counter-current arrangement to the natural gas mixture. Exchanges of hydrocarbons and $CO_2$ occur across the membrane 206 of the HFM.

A full description of the modelling of membrane wetting and the underlying assumption was given in a previous work "*Modeling for design and operation of high-pressure membrane contactors in natural gas sweetening*" in *Chemical Engineering Research and Design* 132, 1005-1019 (2018) and the entirety of it is included herein by reference. A conceptual variable called wetted radius ($r_w[m]$) is introduced to represent the average fraction of membrane pores filled with liquid, in order to describe the degree of membrane wetting. The non-wetted and fully-wetted modes of operation correspond to $r_w=r_2$ and $r_w=r_1$, respectively, with $r_1$ and $r_2$ being the inner and outer radius of the fibre as shown in FIG. 2. On exploiting symmetry, the spatial domain to model a piece of hollow fibre can be taken as $(r,z)\in[0,r_3]\times[0,L]$, which is further partitioned into four subdomains as shown in FIG. 2: (i) tube 204, $0\le r\le r_1$; (ii) membrane-dry, $r_1\le r\le r_w(z)$; (iii) membrane-wet, $r_w(z)\le r\le r_2$; and (iv) shell 208, $r_2\le r\le r_3$. The geometry of the wetted and non-wetted membrane subdomains is complicated by the dependence of the wetted radius on the axial position, z. Many factors are known to affect a degree of wetting, including the membrane-solvent combination, membrane properties such as contact angle and various operating parameters. In principle, membrane wetting could be prevented by keeping transmembrane pressure below a critical breakthrough pressure.

Mass conservation equations in the tube 204, the membrane 206 and the shell 208 sections of the HFM, together with the associated boundary conditions and underlying assumptions are shown in Table 1 below as reference. These equations consider steady-state and isothermal operation in all phases and were previously described in the previous work "*Modeling for design and operation of high-pressure membrane contactors in natural gas sweetening*" in Chemical Engineering Research and Design 132, 1005-1019 (2018)".

TABLE 1

Summary of mass conservation equations and boundary conditions.

| Section | Material Balances |
|---|---|
| Gas Phase<br>$(r, z) \in [0, r_1] \times [0, L]$: | $\dfrac{d\overline{C_{CO_2}}(z)}{\partial z} = -\dfrac{2 D_{CO_2,md}}{\overline{v_g}(z) r_1}\left[1 - \dfrac{ZRT_g^{in}\overline{C_{CO_2}}(z)}{P_g^{in}}\right]\dfrac{\partial C_{CO_2}(r, z)}{\partial r}\bigg|_{r=r_1^+}$ <br><br> $\dfrac{d\overline{v_g}(z)}{\partial z} = -\dfrac{2 D_{CO_2,md}}{r_1}\dfrac{ZRT_g^{in}}{P_g^{in}}\dfrac{\partial C_{CO_2}(r, z)}{\partial r}\bigg|_{r=r_1^+}$ |
| Membrane-Dry Phase<br>$(r, z) \in [r_1, r_w(z)] \times [0, L]$: | $D_{CO_2,md}\left[\dfrac{\partial^2 C_{CO_2}(r, z)}{\partial r^2} + \dfrac{1}{r}\dfrac{\partial C_{CO_2}(r, z)}{\partial r}\right] = 0$ |
| Membrane-Wet Phase<br>$(r, z) \in [r_w(z), r_2] \times [0, L]$: | $D_{i,mw}\left[\dfrac{\partial^2 C_i(r, z)}{\partial r^2} + \dfrac{1}{r}\dfrac{\partial C_i(r, z)}{\partial r}\right] + R_i(C_i(r, z)) = 0, i \in \{CO_2, sol\}$ |
| Liquid Phase<br>$(r, z) \in [r_2, r_3] \times [0, L]$: | $v_1(r)\dfrac{\partial C_i(r, z)}{\partial z} = D_{i,1}\left[\dfrac{\partial^2 C_i(r, z)}{\partial r^2} + \dfrac{1}{r}\dfrac{\partial C_i(r, z)}{\partial r} + \dfrac{\partial^2 C_i(r, z)}{\partial z^2}\right] + R_i(C_i(r, z)),$ <br> $i \in \{CO_2, sol\}$ <br><br> $v_1(r) = 2\overline{v_1}(r_3^2 - r_2^2)\dfrac{r^2 - r_2^2 + 2r_3^2\ln\left(\dfrac{r_2}{r}\right)}{4r_2^2 r_3^2 - r_2^4 - 3r_3^4 - 4r_3^4\ln\left(\dfrac{r_2}{r_3}\right)},$ <br><br> $\overline{v_1} = \dfrac{F_1^{in}}{\pi R_m^2 (1 - \phi)}$ |

| Boundary Conditions |
|---|

| Gas inlet, z = L: | $\overline{v_g}(L) = \dfrac{M_g^{in}}{N\pi r_1^2 \rho_g}, \overline{C_{CO_2}}(L) = \dfrac{y_{CO_2,g}^{in} P_g^{in}}{ZRT_g}$ |
|---|---|
| Liquid inlet,<br>r = 0, r ∈ [r_2, r_3]:<br>Liquid outlet. | $C_{CO_2}(r, 0) = f_{CO_2,1}{}^{in}C_{sol}{}^{in}, C_{sol}(r, 0) = C_{sol}{}^{in}$ |
| r = L, r ∈ [r_2, r_3]: | $\dfrac{\partial C_i(r, z)}{\partial z}\bigg|_{z=L} = 0 \; i \in \{CO_2, sol\}$ |
| Gas-membrane Interface<br>r = r_1, z ∈ [0, L]: | $C_{CO_2}(r_1^+, z) = \overline{C_{CO_2}}(z)$ |
| Gas-liquid Interface<br>r = r_w(z), z ∈ [0, L]: | $C_{CO_2}(r_w^-(z), z) = \dfrac{H_{CO_2,1}}{ZRT_g}C_{CO_2}(r_w^+(z), z),$ <br><br> $\dfrac{\partial C_{sol}(r, z)}{\partial r}\bigg|_{r=r_w^+(z)} = 0$ <br><br> $D_{CO_2,md}\dfrac{\partial C_{CO_2}(r, z)}{\partial r}\bigg|_{r=r_w^-(z)} = D_{CO_2,mw}\dfrac{\partial C_{CO_2}(r, z)}{\partial r}\bigg|_{r=r_w^+(z)}$ |
| Liquid-membrane Interface<br>r = r_2, z ∈ [0, L]: | $C_i(r_2^+, z) = C_i(r_2^-, z), i \in \{CO_2, sol\}$ <br><br> $D_{i,1}\dfrac{\partial C_i(r, z)}{\partial r}\bigg|_{r=r_2^+} = D_{i,mw}\dfrac{\partial C_i(r, z)}{\partial r}\bigg|_{r=r_2^-}, i \in \{CO_2, sol\}$ |
| Liquid Boundary<br>r = r_3, z ∈ [0, L]: | $\dfrac{\partial C_i(r, z)}{\partial r}\bigg|_{r=r_3} i \in \{CO_2, sol\}$ |

The following sections detail the modelling of hydrocarbon absorption in solvent and solvent evaporative losses, and the energy balance to describe temperature variation inside the MBC in accordance with an embodiment.

Modelling of Hydrocarbon Losses

As a first approximation, the solvent is assumed to be saturated with hydrocarbons (HC) at the MBC liquid outlet (z=L) and Henry's Law is used to estimate their concentrations using the Equation 1 below:

$$C_{i,l}^{out} = \frac{y_{i,g}^{in} P_g}{H_{i,l}}, i \in \{CH_4, C_2H_6, C_3H_8\} \quad (1)$$

where $P_g$ [Pa] is the gas pressure, $y_{CO_2,g}^{in}$ [−] is the inlet molar fraction of the hydrocarbons, and $H_{i,l}$ [m³ Pa mol⁻¹] is the Henry's constant of the hydrocarbons which corresponds to an outlet solvent temperature, pressure and composition. Since the solvent inlet stream to the MBC does not contain any hydrocarbon, the loss rate in hydrocarbons to the solvent is considered at the overall mass balance level (lumped). By this, it means that the loss rate in hydrocarbons to the solvent is not calculated along the length of the MBC but only at the outlet of the MBC. This reduces computational time required for the loss rate calculation. The loss rate in hydrocarbons to the solvent is obtained using the Equation 2 below:

$$N_{i,l}^{out} = C_{i,l}^{out} F_l, i \in \{CH_4, C_2H_6, C_3H_8\}, \quad (2)$$

where $F_l$ is a liquid flowrate of the solvent. The loss rate as shown above in Equation 2 provides a worst-case scenario in estimating the amount of HC that is potentially lost if they are not recovered in the downstream flash drum. It is useful for benchmarking the HC losses compared to other conventional $CO_2$ removal technologies. The prediction of the $H_{i,l}$ is detailed later in relation to Equation 13 below.

Modelling of Solvent Evaporation in Treated Gas

Like with hydrocarbon losses before, it is assumed herein that the treated gas at the MBC outlet (z=0) is saturated with solvent and the solvent evaporation rate is considered at the overall mass balance level (lumped). This assumption may over-predict the solvent evaporation rate due to the gas residence time being shorter than necessary to reach its equilibrium. Nevertheless, it is interesting to model the worst-case solvent evaporation rate to investigate the solvent loss in treated gas with respect to solvent circulation rate and to benchmark the solvent rate loses in a MBC system with a conventional packed column system (see in relation to FIGS. 26A and 26B as described below).

For the vapour-liquid equilibrium at z=0, Raoult's Law can be used to approximate the molar fraction of solvent in the gas outlet, $y_{i,g}^{out}$ [−], using Equation 3 below as $$y_{i,g}^{out} = \frac{x_{i,l}^{in} P_i^{vap,in}}{P_g^{out}}, i \in \{H_2O, MDEA, PZ\} \quad (3)$$

where the terms $x_{i,l}^{in}$[−], $P_i^{vap,in}$ [kPa], and $P_g^{out}$ [kPa] are the molar fraction, the vapour pressures of species i∈{$H_2O$, MDEA, PZ} at a liquid inlet, and the gas outlet pressure, respectively.

Since the gas inlet in a counter-current flow MBC is solvent free, the solvent loss rate, $N_{i,g}^{out}$ [mol s⁻¹] is calculated using Equation 4 below as $$N_{i,g}^{out} = N\pi r_1^2 \overline{v_g}(0) \frac{y_{i,g}^{out} P_g}{ZRT_g}, i \in \{H_2O, MDEA, PZ\} \quad (4)$$

where N is the number of fibres in the MBC module, $r_1$ [m] is the inner radius of the fibres, $\overline{v_g}$ [m s⁻¹] is the average velocity of the gas phase, Z [−] is the compressibility factor, and R=8.3145 J mol⁻¹K⁻¹ is the ideal gas constant.

Modelling of Solvent Temperature

Instead of using a simple temperature correction based on a lumped energy balance, a spatial distributed modelling of the solvent temperature is performed in accordance with an embodiment. This modelling accounts for heat losses due to solvent evaporation as aforementioned discussed, and the exothermic reaction between $CO_2$ and the amines under adiabatic condition. For simplicity, the assumption is made that the solvent evaporation occurs at the liquid inlet (z=0) before the solvent reacts with the $CO_2$ along the fibre length. It is noted that while solvent evaporation decreases the solvent temperature, $CO_2$ absorption increases the solvent temperature. Therefore, modeling of the solvent temperature will provide insight on the relative contribution of each effect on the solvent temperature. An experimental verification will confirm the validity of the modeling assumptions later.

Based on the solvent evaporation rate determined in the Equation 4 above, the energy consumed for solvent evaporation, $Q_{vap}$ [J s⁻¹] and the solvent temperature at shell inlet, $T_l(0)$ can be determined as show in Equation 5.

$$Q_{vap} = F_l^{in} \rho_l C_p (T_l^{in} - T_l(0)) = \overline{v_g}(0) N\pi r_1^2 \sum \frac{x_{i,l}^{in} P_i^{vap,in}}{ZRT_g} \Delta H_i^{vap}(T_l^{in}) \quad (5)$$

where $F_l^{in}$ [m³ s⁻¹], $\rho_l$ [kg m⁻³], $C_p$ [J kg⁻¹ K⁻¹], $T_l^{in}$ [K], $P_i^{vap,in}$ and $\Delta H_i^{vap}$ [J mol⁻¹], are solvent inlet volumetric flowrate, density, specific heat capacity, inlet temperature, inlet vapour pressure and the latent heat of vaporization of species i∈{$H_2O$, MDEA, PZ}, respectively. The specific heat capacity of the amine solvent and the latent heat of vaporization are set to $C_p$=3600 J kg⁻¹ K⁻¹ and $\Delta H_{H_2O}^{vap}$=12688, $\Delta H_{MDEA}^{vap}$=62120, and $\Delta H_{PZ}^{vap}$=38750 J mol⁻¹, respectively.

Diffusive heat transfer in the shell is fast enough and so thermal diffusion along the axis may be neglected. Furthermore, the solvent temperature is assumed to be homogeneous in the radial direction. This leads to the following energy balance, as shown in Equation 6, for quantifying the solvent temperature rise, $T_l(z)$ along the fibre length by accounting for the exothermic $CO_2$ absorption reaction under adiabatic conditions:

$$F_l^{in} \rho_l C_p \frac{dT_l(z)}{dz} = -\pi r_1^2 N \frac{d(\overline{v_g}(z)\overline{C_{CO_2}}(z))}{dz} \Delta H_r \quad (6)$$

where $\overline{C_{CO_2}}(z)$ is the average concentration of $CO_2$ along the fibre length, and the enthalpy of reaction is set to $\Delta H_r$=−60000 J mol⁻¹.

Notice that the Equation 6 above is now refined to be in spatial distributed modelling in accordance with an embodiment and therefore advantageously introduce a spatial dimension for the change in the solvent temperature along the fibre length of the MBC. The predicted value of $T_l(0)$ in Equation 5 provides the boundary condition at z=0 for Equation 6.

Membrane Characteristics

The high-pressure MBC modules were packed with hydrophobic, Polytetrafluoroethylene (PTFE) hollow fibres. Table 2 below shows the main characteristics and geometrical properties of the MBC used for lab- and pilot-scale testing. The lab-scale setup and the pilot-scale NG plant are described below in relation to FIG. 8 and FIG. 9 respectively. The data can be obtained from the manufacturer (e.g. PRSB, 2016—'Module D—Hollow Fiber Membrane (HFM) Quality Check and Characterization', PETRONAS Research Sdn Bhd.) or calculated from analytical equation based on the obtained data.

TABLE 2

Specifications of the lab- and pilot-scale membranes.

Figures 5A, 5B:
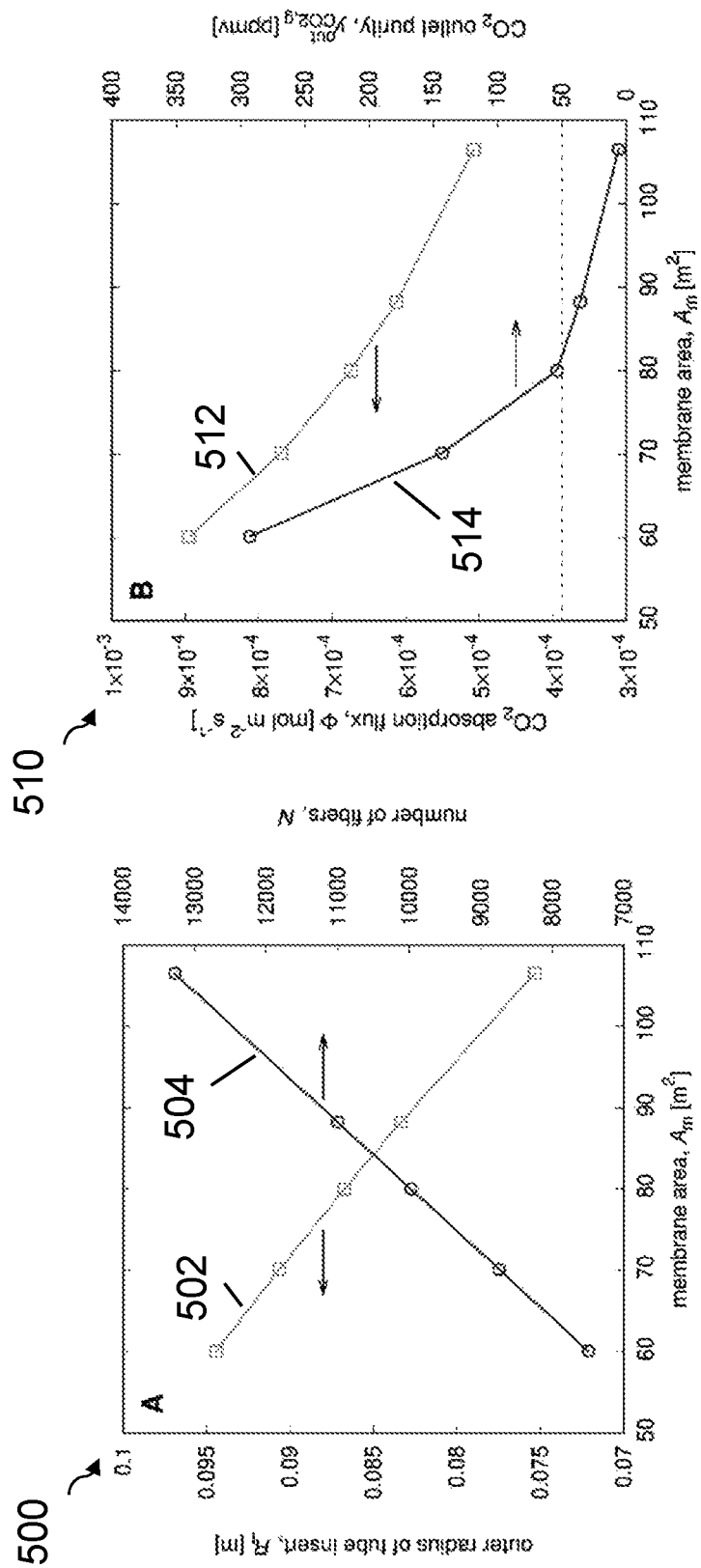
FIGS. 5A and 5B show graphs associated with different membrane areas of the hollow fibre MBC in accordance with an embodiment, where

| Parameters | Lab module | Pilot module | Source |
|---|---|---|---|
| Fibre length, L [m] | 2.3 | 2.3 | (PRSB, 2016) |
| Fibre inner radius, $r_1$ [μm] | 225 | 225 | (PRSB, 2016) |
| Fibre outer radius, $r_2$ [μm] | 550 | 550 | (PRSB, 2016) |
| Membrane porosity, ε [—] | 0.41 | 0.41 | (PRSB, 2016) |
| Membrane tortuosity, τ [—] | 6.1 | 6.1 | Equation 7 |
| Max. pore radius, $\delta_{max}$ [μm] | 0.18 | 0.18 | (PRSB, 2016) |
| Mean pore radius, $\bar{\delta}$ [μm] | 0.06 | 0.06 | Equation 8 |
| Pore standard deviation, σ [—] | 0.24 | 0.24 | Equation 8 |
| Contact angle, θ [°] | 92.4 | 92.4 | (PRSB, 2016) |
| Packing density, ∅ [—] | 0.40 | 0.38 | in relation to FIGS. 5A, 5B |
| Module inner radius, $R_m$ [m] | 0.0125 | 0.115 | (PRSB, 2016) |
| Membrane area, $A_m$ [m²] | 1.67 | 68 | in relation to FIGS. 5A, 5B |
| No of fibres, N | 209 | 8400 | (PRSB, 2016) |
| Specific surface area [m⁻¹] | 1700 | 1600 | (PRSB, 2016) |
| Outer radius of tube insert, $R_t$ [m] | N/A | 0.08 | in relation to FIGS. 5A, 5B |

A first approximation of the membrane tortuosity can be obtained using the Equation 7 below:

$$\tau = \frac{(2-\varepsilon)^2}{\varepsilon}. \tag{7}$$

The pore-size distribution (PSD) data from the manufacturer (PRSB, 2016) were used to fit the following log-normal distribution in Equation 8 below, $$f(\delta) = \frac{1}{\sqrt{2\pi \ln(1+\sigma^2)}\,\bar{\delta}} \exp\left(-\frac{(\ln^{\delta}/\bar{\delta})^2(1+\sigma^2)}{2\ln(1+\sigma^2)}\right), \tag{8}$$

where $\bar{\delta}$ and σ stand for the mean pore radius and relative pore standard deviation, respectively.

Figures 3, 4:
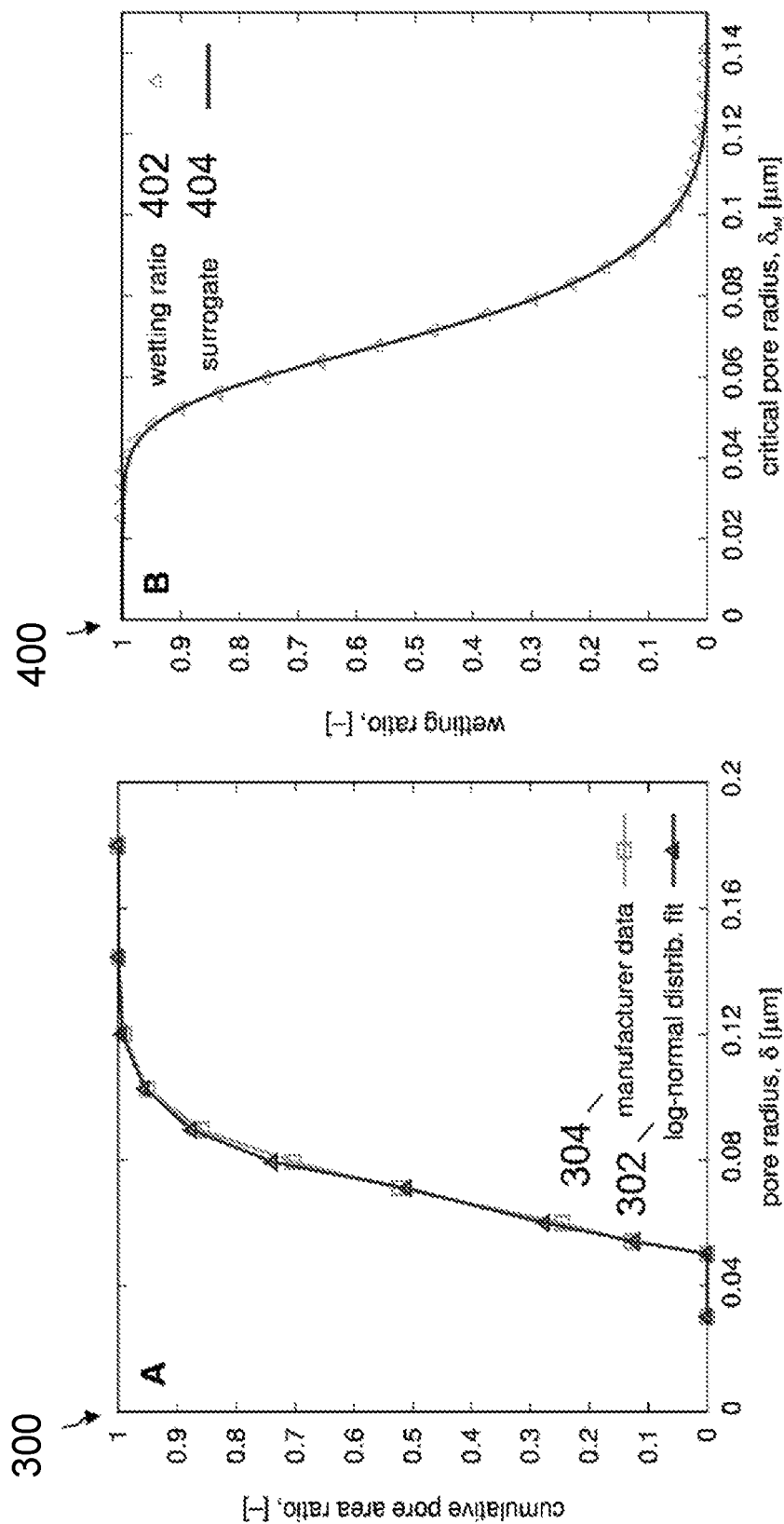
FIG. 3 shows a graph comparing cumulative pore area ratio distribution based on simulated log-normal pore size distribution with the manufacturer data in accordance with an embodiment.
FIG. 4 shows a graph comparing an analytic wetting ratio expression with a fitted surrogate expression in terms of critical pore radius in accordance with an embodiment.

FIG. 3 shows a graph 300 of cumulative pore area ratio distribution based on simulated log-normal pore size distribution 302 and the manufacturer data 304 in accordance with an embodiment. FIG. 4 shows a graph 400 comparing an analytic wetting ratio expression 402 with a fitted surrogate expression 404 in terms of a critical pore radius. The graphs of FIGS. 3 and 4 are fitted using the Equation 8 above.

The resulting least-squares fit in FIG. 3 shows an excellent agreement with the data, and the corresponding estimate for $\bar{\delta}$ and σ can be found in the Table 2 above. In turn, a surrogate relationship for the wetting ratio $\mathfrak{z}$ as a function of the critical pore radius $\delta_w$ in the range [0, $\delta_{max}$] could be obtained in the form $$\mathfrak{z}(\delta_w) = \frac{1 + \tanh\left(a_0 + a_1 \delta_w/\bar{\delta} + a_2(\delta_w/\bar{\delta})^2 + a_3(\delta_w/\bar{\delta})^3\right)}{2}, \tag{9}$$

with $a_0=9.029$, $a_1=-17.209$, $a_2=11.222$, and $a_3=-2.938$. Under the assumption that the wetted pores are completely filled with liquid, the wetting ratio may be computed using Equation 10 as:

$$\mathfrak{z}(z) = \frac{\int_{\delta_w(z)}^{\delta_{max}} \delta^2 f(\delta)\,d\delta}{\int_0^{\delta_{max}} \delta^2 f(\delta)\,d\delta}, \tag{10}$$

for a given pore size distribution (PSD) function $f$, and a maximal pore radius, $\delta_{max}$ [m]. A comparison between the actual wetting ratios 402 calculated using Equation 10 above and the fitted surrogate 404 using Equation 9 above is shown in FIG. 4.

Pilot-Scale Module Design

The characteristics of the HFM as well as the braiding are expected to provide a large pilot-scale gas treating capacity due to a relatively large specific surface area of ca. 2300 m⁻¹ for a packing density of ø=0.55. However, the pilot plant cannot operate at a gas flowrate higher than 75 kg hr⁻¹ due to limitations in other parts of the plant. As a result, operating the pilot plant at design capacity with the new membrane in a horizontal operation would result in $CO_2$ removal efficiency close to 100% in most experiments. Therefore, a new pilot module that would achieve a $CO_2$ purity of 50 ppmv at the full capacity is required. In order to maintain packing density in the new module close to 0.55, the module cross-sectional area was scaled down by inserting a steel tube (e.g. a tube insert) at the center of the module. The packing density, ø and membrane area, $A_m$ are given by $$\phi = \frac{r_2^2 N}{R_m^2 - R_t^2}, \tag{11}$$

$$A_m = 2\pi r_2 L N, \tag{12}$$

where N is the number of fibres in the MBC module, $R_m$ [m] and $R_t$ [m] are the inner radius of the module and the outer radius of the steel tube insert respectively, and L is the fibre length.

FIGS. 5A and 5B show graphs 500, 510 associated with different membrane areas of the hollow fibre MBC in accordance with an embodiment, where FIG. 5A shows a graph 500 of the required outer radius 502 of the steel tube insert and predicted total number of fibres 504 in the MBC module for different membrane areas in order to maintain a packing density of 0.55, and FIG. 5B shows a graph 510 of predicted $CO_2$ absorption flux 512, Φ [mol m⁻² s⁻¹] and $CO_2$ outlet gas purity 514, $y_{CO_2,g}^{out}$ [ppmv] for different membrane areas at the maximum pilot capacity (i.e. $M_g^{in}$=75 kg $h^{-1}$, $F_l^{in}$=275 L $h^{-1}$, $y_{CO_2,g}^{in}$=5 mol %). These predictions are computed using the membrane properties as shown in Table 2.

As shown in FIG. 5B, the model predicts a $CO_2$ outlet gas purity 514 lower than 50 ppmv in cases of total membrane area above 80 $m^2$, with negligible wetting for all the cases due to horizontal operation of the MBC. It is also observed from FIG. 5B that the $CO_2$ absorption flux 512 decreases with larger membrane area, given that the membrane area is already large enough for the $CO_2$ outlet purity to be at the ppm level.

However, due to the rigid steel tube and braided structure of the HFM, only 8400 fibres could be successfully installed in practice with a tube insert of radius, $R_t$=0.08 m compared to the required ca. 11,000 fibres. This configuration yields a packing density of only 0.38 and a reduced surface area of 68 $m^2$, as reported in Table 2 above. Nonetheless, this module configuration was used to perform all the pilot-scale tests as described below.

Prediction of Hydrocarbon Solubility in Amine Solvent

The solubility of methane, ethane and propane in water and in aqueous amine solutions of 50 wt % MDEA were gathered from solubility charts reported in previous works. These charts were derived from a combination of thermodynamic modeling (i.e. Peng-Robinson Equation of State and Henry's Law) and experimental data.

The following polynomial regression model for Henry's constant for hydrocarbon in amine solvent, $H_{i,l}$ $i \in \{CH_4, C_2H_6, C_3H_8\}$ was fitted to this data set for a temperature range of 300-345 K and a pressure range of 48-72 bar. The regression model is developed using Design-Expert version 11 and is shown in Equation 13 below:

$$H_{i,l} = \alpha_0 + \alpha_1 C + \alpha_2 T_l + \alpha_3 P_l + \alpha_4 C T_l + \alpha_5 C P_l + \alpha_6 T_l P_l \quad (13)$$

where $T_l$ [K], $P_l$ [Pa], and C [-] are the liquid temperature, liquid pressure, and the mass fraction of MDEA in aqueous amine solvent, respectively. It should be appreciated that although the regression model was developed using Design-Expert version 11, other suitable software for forming the regression model may be used.

The coefficients $\alpha_1$ to $\alpha_6$ of each Henry's constants and absolute average deviations are given in Table 3 below.

Figure 6A:
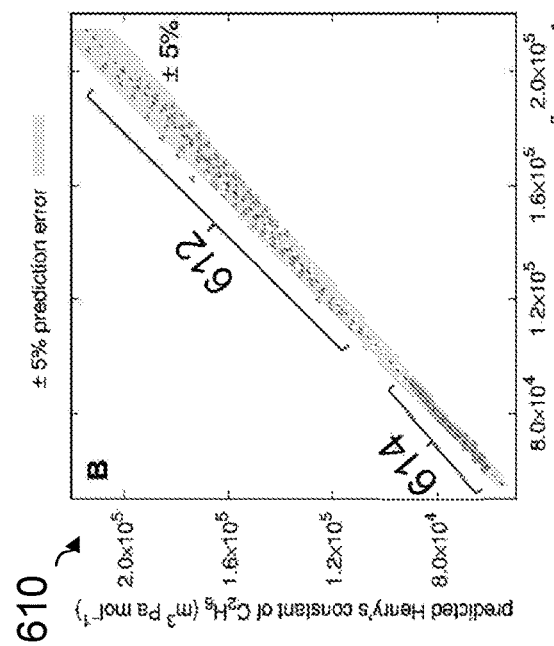
FIGS. 6A, 6B and 6C show graphs of predicted and measured Henry's constant of different hydrocarbons in water and 50 wt % aqueous MDEA in accordance with an embodiment, where
Figure 6B:
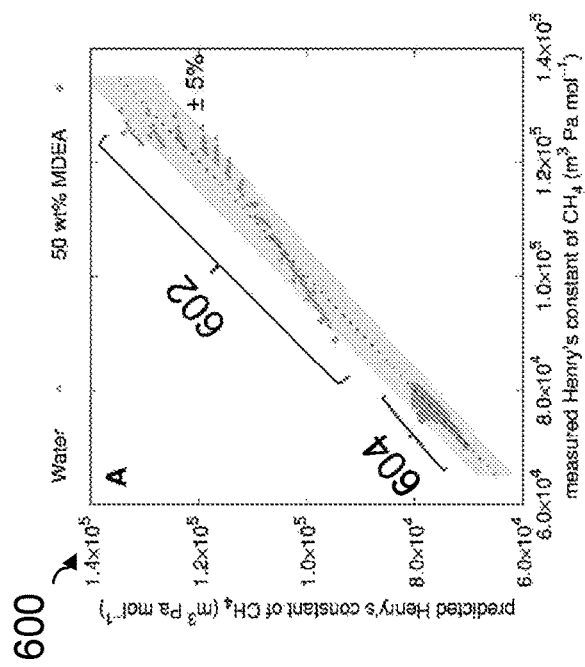
Figure 6C:
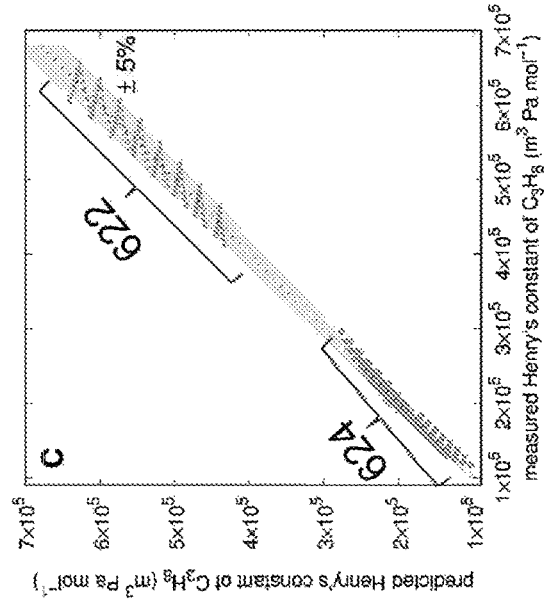

FIGS. 6A, 6B and 6C show graphs 600, 610, 620 of predicted and measured Henry's constant of different hydrocarbons in water and in 50 wt % aqueous MDEA in accordance with an embodiment, where FIG. 6A shows a graph 600 of predicted and measured Henry's constant for methane ($CH_4$), FIG. 6B shows a graph of predicted and measured Henry's constant for ethane ($C_2H_6$) and FIG. 6C shows a graph of predicted and measured Henry's constant for propane ($C_3H_8$). Data points 602, 612 and 622 of FIG. 6A, FIG. 6B and FIG. 6C respectively are associated with the experimental data of the Henry's constant of different hydrocarbons in water, while data points 604, 614 and 624 of FIG. 6A, FIG. 6B and FIG. 6C respectively are associated with the experimental data of the Henry's constant of different hydrocarbons in 50 wt % aqueous MDEA.

A comparison between the experimental and predicted Henry's constants as presented in FIGS. 6A, 6B and 6C show excellent agreement, with a deviation of most predictions being between ±5%. The resulting Henry's constants surrogates Equation 13 will be used to predict the hydrocarbon worst-case losses.

TABLE 3

Coefficients for $H_{i,l}$ and absolute average deviations

| $H_{i,l}$ | $H_{CH_4,l}$ [$m^3$ Pa $mol^{-1}$] | $H_{C_2H_6,l}$ [$m^3$ Pa $mol^{-1}$] | $H_{C_3H_8,l}$ [$m^3$ Pa $mol^{-1}$] |
|---|---|---|---|
| $\alpha_0$ | $-2.90 \times 10^5$ | $-5.97 \times 10^5$ | $-1.67 \times 10^5$ |
| $\alpha_1$ | $3.56 \times 10^5$ | $8.12 \times 10^5$ | $9.50 \times 10^5$ |
| $\alpha_2$ | $1.26 \times 10^3$ | $2.01 \times 10^3$ | $7.34 \times 10^2$ |
| $\alpha_3$ | $2.40 \times 10^{-2}$ | $5.63 \times 10^{-2}$ | $1.40 \times 10^{-1}$ |
| $\alpha_4$ | $-1.42 \times 10^3$ | $-2.72 \times 10^3$ | $-3.44 \times 10^3$ |
| $\alpha_5$ | $4.41 \times 10^{-3}$ | $-1.95 \times 10^{-2}$ | $-8.89 \times 10^{-2}$ |
| $\alpha_6$ | $-7.43 \times 10^{-5}$ | $-1.16 \times 10^{-4}$ | $-1.96 \times 10^{-4}$ |
| AAD (%) | 1.8 | 1.5 | 3.0 |

Prediction of Henry's Constant in Semi-Lean Amine Solvent

To determine the Henry's constant of $CO_2$ in order to account for the effect of $CO_2$ loading in a solvent (e.g. an amine solution), a regression model is developed using empirical data. In an embodiment, the regression model may be formed for a Henry's constant of $CO_2$ using empirical data associated with $CO_2$ solubility in the solvent. It may not be easy to obtain direct empirical data associated with $CO_2$ solubility in the solvent. In the present embodiment as described below, the Henry's constant of $CO_2$ is determined using a regression model formed for a Henry's constant of nitrous oxide ($N_2O$). $N_2O$ is chosen because $N_2O$ has similar properties to $CO_2$ and is not reactive to the solvent. Experiments conducted to obtain $N_2O$ solubility in solvents are therefore simple and their data reliable. In the present embodiment, the regression model is developed based on empirical data of $N_2O$ solubility in aqueous solution 50 wt % of MDEA for $CO_2$ loading and temperature in the range of 0-0.5 mol $mol^{-1}$ and 295-353 K, respectively. It should be appreciated that although the regression model is developed using data of aqueous solution 50 wt % of MDEA, data from other suitable solvent could be used. Here, the effect of pressure on Henry's constant is neglected, and assume that PZ behaves like MDEA. The regressed Henry's constant for $N_2O$ is given in Equation 14 below as:

$$H_{N_2O,l} = -3.30 \times 10^4 - 3.79 \times 10^4 f_{CO_2,l}^{in} + 1.70 \times 10^2 T_l - 4.37 \times 10^3 (f_{CO_2,l}^{in})^2 - 1.34 \times 10^{-1} T_l^2 + 1.45 \times 10^2 f_{CO_2,l}^{in} T_l \quad (14)$$

where $f_{CO_2,l}^{in}$ and $T_l$ are inlet $CO_2$ loading in amine and liquid temperature, respectively.

FIGS. 7A and 7B show graphs 700, 710 of predicted and measured Henry's constant of nitrous oxide ($N_2O$). FIG. 7A shows a graph 700 comparing experimental data of the Henry's constant of $N_2O$ with predicted Henry's constant of $N_2O$. The dotted line 702 as shown in FIG. 7A represents the regression model of Equation 14 above with a 5% spread. FIG. 7B shows a graph 710 of predicted Henry's constant of $N_2O$ at various $CO_2$ loading for lean amine and semi-lean amine operation. The dotted line 712 shows the graph of the predicted Henry's constant of $N_2O$ for lean amine operation while the line 714 shows the graph of the predicted Henry's constant of $N_2O$ for semi-lean amine operation.

The comparison in FIG. 7A between the experimental and the predicted $H_{N_2O,l}$ based on the surrogate in the Equation 14 shows good agreement. It can be seen in FIG. 7B that the regression model developed for the lean-amine solvent predicts lower $H_{N_2O,l}$ when compared with the Equation 14 above for all $CO_2$ loadings. The regression model for the lean-amine solvent used is shown in Equations 15 and 16 below for completeness:

$$\ln H_{N_2O,l} = \Phi_{MDEA}\ln H_{N_2O,MDEA} + \Phi_{PZ}\ln H_{N_2O,PZ} +$$
$$\Phi_{H_2O}\ln H_{N_2O,H_2O} + \Phi_{MDEA}\Phi_{H_2O}\left[-2.899 + \frac{1405.43}{T_l^{in}}\right] \quad (15)$$

with $\phi_i$ the volume fraction of species i; and the solubility of $N_2O$ in pure amine solvent i∈{MDEA,PZ} taken as:

$$H_{N_2O,MDEA} = H_{N_2O,PZ} = 1.52 \times 10^5 \exp\left(-\frac{1312.7}{T_l^{in}}\right). \quad (16)$$

Using the Henry's constant determined above for $N_2O$, Henry's constant for $CO_2$ can be estimated at various temperatures based on $N_2O$ analogy using Equations 17 to 19 below.

$$H_{CO_2,l} = H_{N_2O,l}\frac{H_{CO_2,H_2O}}{H_{N_2O,H_2O}} \quad (17)$$

Henry's constants for $N_2O$ and $CO_2$ in water, respectively $H_{CO_2,H_2O}$ and $H_{N_2O,H_2O}$ are taken as:

$$H_{CO_2,H_2O} = 2.82 \times 10^6 \exp\left(-\frac{2044}{T_l^{in}}\right), \quad (18)$$

$$H_{N_2O,H_2O} = 8.55 \times 10^6 \exp\left(-\frac{2284}{T_l^{in}}\right), \quad (19)$$

A higher value of $H_{N_2O,l}$ results in a higher $H_{CO_2,l}$ which in turn denotes a lower $CO_2$ solubility in the solvent. In addition, the gradient increase of $H_{N_2O,l}$ using the Equation 15 above is higher compared to the Equation 14 which confirms the adverse effect of a higher $CO_2$ loading on the $CO_2$ absorption flux.

For completeness, the equations, the models and the boundary conditions used in the MBC model are summarized in Table 4 below. As compared to Table 3, Table 4 has been updated with considerations of the models and equations as discussed above.

TABLE 4

Summary of model equations and boundary conditions used in the MBC model

| Section | Material Balances |
|---|---|
| Gas Phase<br>(r, z) ∈ [0, $r_1$] × [0, L]: | $\frac{d\overline{C_{CO_2}}(z)}{\partial z} = -\frac{2D_{CO_2,md}}{\overline{v_g}(z)r_1}\left[1 - \frac{ZRT_g^{in}\overline{C_{CO_2}}(z)}{P_g^{in}}\right]\frac{\partial C_{CO_2}(r,z)}{\partial r}\bigg\|_{r=r_1^+}$<br>$\frac{d\overline{v_g}(z)}{\partial z} = -\frac{2D_{CO_2,md}}{r_1}\frac{ZRT_g^{in}}{P_g^{in}}\frac{\partial C_{CO_2}(r,z)}{\partial r}\bigg\|_{r=r_1^+}$,<br>$N_{i,g}^{out} = N_{i,g}^{in} - N_{i,1}^{out}$, i ∈ {$CH_4$, $C_2H_6$, $C_3H_8$},<br>$y_{i,g}^{out} = \frac{x_{i,1}^{in}P_i^{vap,in}}{P_g^{out}}$, i ∈ {$H_2O$, MDEA, PZ},<br>$N_{i,g}^{out} = N\pi r_1^2 \overline{v_g}(0)\frac{y_{i,g}^{out}P_g}{ZRT_g}$, {$H_2O$, MDEA, PZ}, |
| Membrane-Dry Phase<br>(r, z) ∈ [$r_1$, $r_w(z)$] × [0, L]: | $\frac{r_{w\_ref} - r_1}{r_w(z) - r_1}D_{CO_2,md}\left[\frac{\partial^2 C_{CO_2}(r,z)}{\partial r^2} + \frac{1}{r}\frac{\partial C_{CO_2}(r,z)}{\partial r}\right] = 0$ |
| Membrane-Wet Phase<br>(r, z) ∈ [$r_w(z)$, $r_2$] × [0, L]: | $\frac{r_2 - r_{w\_ref}}{r_2 - r_w(z)}D_{i,mw}\left[\frac{\partial^2 C_i(r,z)}{\partial r^2} + \frac{1}{r}\frac{\partial C_i(r,z)}{\partial r}\right] + R_i(C_i(r,z)) = 0$, i ∈ {$CO_2$, sol} |
| Liquid Phase<br>(r, z) ∈ [$r_2$, $r_3$] × [0, L]: | $v_1(r)\frac{\partial C_i(r,z)}{\partial r} = D_{i,1}\left[\frac{\partial^2 C_i(r,z)}{\partial r^2} + \frac{1}{r}\frac{\partial C_i(r,z)}{\partial r} + \frac{\partial^2 C_i(r,z)}{\partial z^2}\right] + R_i(C_i(r,z))$,<br>i ∈ {$CO_2$, sol}<br>$v_1(r) = 2\overline{v_1}(r_3^2 - r_2^2)\frac{r^2 - r_2^2 + 2r_3^2\ln\left(\frac{r_2}{r}\right)}{4r_2^2r_3^2 - r_2^4 - 3r_3^4 - 4r_3^4\ln\left(\frac{r_2}{r_3}\right)}$,<br>$\overline{v_1} = \frac{F_1^{in}}{\pi R_m^2(1 - \phi)}$,<br>$C_{i,1}^{out} = \frac{y_{i,g}^{in}P_g}{H_{i,1}}$, i ∈ {$CH_4$, $C_2H_6$, $C_3H_8$},<br>$N_{i,1}^{out} = C_{i,1}^{out}F_1$, i ∈ {$CH_4$, $C_2H_6$, $C_3H_8$}, |
| Boundary Conditions | |
| Gas inlet, z = L: | $N_{i,1}^{out} = N_{i,1}^{in} - N_{i,g}^{out}$, {$H_2O$, MDEA, PZ},<br>$F_1^{in}\rho_1 C_p \frac{dT_1(z)}{dz} = -\pi r_1^2 N \frac{d(\overline{v_g}(z)\overline{C_{CO_2}}(z))}{dz}\Delta H_r$ |

TABLE 4-continued

Summary of model equations and boundary conditions used in the MBC model

Liquid inlet,
$r = 0, r \in [r_2, r_3]$:

$$\overline{v_g}(L) = \frac{M_g^{in}}{N\pi r_1^2 \rho_g}, \overline{C_{CO_2}}(L) = \frac{y_{CO_2,g}^{in} P_g^{in}}{ZRT_g}$$

Liquid outlet
$r = L, r \in [r_2, r_3]$:

$$C_{CO_2}(r, 0) = f_{CO_2,l}^{in} C_{sol}^{in}, C_{sol}(r, 0) = C_{sol}^{in},$$

$$Q_{vap} = F_1^{in} \rho_l C_p (T_1^{in} - T_1(0))$$

$$= \overline{v_g}(0) N\pi r_1^2 \sum \frac{x_{i,1}^{in} P_i^{vap,in}}{ZRT_g} \Delta H_i^{vap}(T_1^{in})$$

Gas-membrane Interface
$r = r_1, z \in [0, L]$:

$$\frac{\partial C_i(r, z)}{\partial z} \bigg|_{z=L} = 0 \; i \in \{CO_2, sol\}$$

Gas-liquid Interface
$r = r_w(z), z \in [0, L]$:

$$C_{CO_2}(r_w^-(z), z) = \frac{H_{CO_2,l}}{ZRT_g} C_{CO_2}(r_w^+(z), z),$$

$$\frac{r_2 - r_{w\_ref}}{r_2 - r_w(z)} \frac{\partial C_{sol}(r, z)}{\partial r} \bigg|_{r=r_w^+(z)} = 0,$$

$$\frac{r_{w\_ref} - r_1}{r_w(z) - r_1} D_{CO_2,md} \frac{\partial C_{CO_2}(r, z)}{\partial r} \bigg|_{r=r_w^-(z)} =$$

$$\frac{r_2 - r_{w\_ref}}{r_2 - r_w(z)} D_{CO_2,mw} \frac{\partial C_{CO_2}(r, z)}{\partial r} \bigg|_{r=r_w^+(z)},$$

$$r_w(z) = r_2 - [r_2 - r_1] \zeta(z),$$

$$\zeta(z) = \frac{\int_{-2\gamma \cos\theta / \Delta P_{TMPD}(z)}^{\delta_{max}} \delta^2 f(\delta) d\delta}{\int_0^{\delta_{max}} \delta^2 f(\delta) d\delta},$$

$$P_{TMPD}(z) = P_1^{out} + 8\mu_l \overline{v_l} \frac{r_3^2 - r_2^2}{4r_2^2 r_3^2 - r_2^4 - 3r_3^4 - 4r_3^4 \ln\left(\frac{r_2}{r_3}\right)} (L - z) - P_g^{in}$$

Liquid-membrane Interface
$r = r_2, z \in [0, L]$:

$$C_i(r_2^+, z) = C_i(r_2^-, z), i \in \{CO_2, sol\}$$

$$D_{i,l} \frac{\partial C_i(r, z)}{\partial r} \bigg|_{r=r_2^+} = \frac{r_2 - r_{w\_ref}}{r_2 - r_w(z)} D_{i,mw} \frac{\partial C_i(r, z)}{\partial r} \bigg|_{r=r_2^-}, i \in \{CO_2, sol\}$$

Liquid Boundary
$r = r_3, z \in [0, L]$:

$$\frac{\partial C_i(r, z)}{\partial r} \bigg|_{r=r_3}, i \in \{CO_2, sol\}$$

TABLE 5

Model parameters used in the lab and pilot plant MBC simulations.

| Parameters | $N_2/CO_2$ (Lab) | NG (Pilot) |
|---|---|---|
| Diffusivity of $CO_2$ in gas, $D_{CO_2, g}$ [m² s⁻¹] | $3.01 \times 10^{-7}$ | $3.10 \times 10^{-7}$ |
| Diffusivity of $CO_2$ in liquid, $D_{CO_2, l}$ [m² s⁻¹] | $1.50 \times 10^{-9}$ | $1.47 \times 10^{-9}$ |
| Diffusivity of MDEA in liquid, $D_{MDEA, l}$ [m² s⁻¹] | $2.85 \times 10^{-10}$ | $2.39 \times 10^{-10}$ |
| Diffusivity of PZ in liquid, $D_{PZ, l}$ [m² s⁻¹] | $6.34 \times 10^{-10}$ | $5.37 \times 10^{-10}$ |
| Reaction rate constant of MDEA, $k_{MDEA}$ [m³mol⁻¹ s⁻¹] | $1.13 \times 10^{-2}$ | $9.83 \times 10^{-3}$ |
| Reaction rate constant of PZ, $k_{PZ}$ [m³mol⁻¹ s⁻¹] | 46.4 | 39.9 |
| Henry's constant, Hco, [m³ Pa mol⁻¹] | 5825 | 4759 |
| Density of gas, $\rho_g$ [kg m⁻³] | 73.4 | 48.9 |
| Density of liquid, $\rho_l$ [kg m⁻³] | 971.3 | 987 |
| Dynamic viscosity of liquid, $\mu_l$ [kg m⁻¹ s⁻¹] | $1.39 \times 10^{-3}$ | $1.71 \times 10^{-3}$ |
| Surface tension of amine solvent, $\gamma$ [N m⁻¹] | 0.040 | 0.046 |

Experimental Setups

Figure 8:
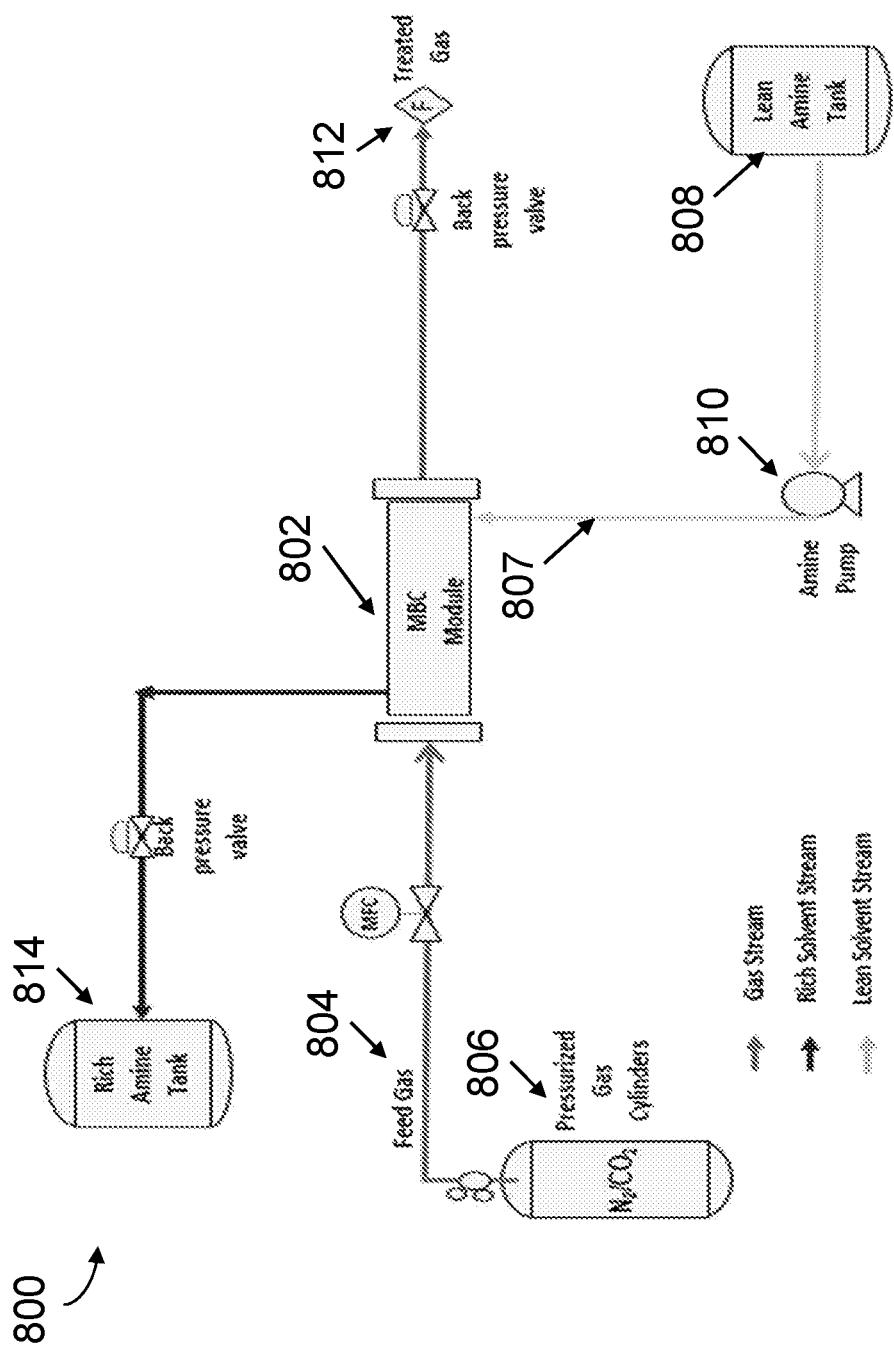
FIG. 8 shows a schematic of a lab-scale set-up for carbon dioxide ($CO_2$) removal in a natural gas sweetening process using a horizontal MBC in accordance with an embodiment.

FIG. 8 shows a schematic 800 of a lab-scale set-up for carbon dioxide ($CO_2$) removal in a natural gas sweetening process using a horizontal MBC module 802 in accordance with an embodiment.

A feed gas 804 comprising mixtures of $CH_4/CO_2$ or $N_2/CO_2$ is provided by pressurized gas cylinders 806 to a tube side of the lab-scale MBC module 802, while a lean solvent 807 (typically lean amine solvent) was pumped through the shell side of the MBC module 802 from a lean amine tank 808 via an amine pump 810, in a counter-current configuration to the feed gas 804. The feed gas flow rate and solvent flow rates were controlled using a mass flow controller (MFC) and pump stroke (not shown), respectively. Treated gas 812 from the MBC module 802 was analyzed. The compositions of the feed gas 804 and treated gas 812 were analyzed and recorded using gas chromatography (e.g. GC7900, Shanghai Tech-comp Instruments Co., Ltd), after the set-up had reached steady state as indicated by a constant $CO_2$ composition in the outlet gas stream of the module 802. The treated gas 812 from the MBC module 802 was then depressurized and vented to a safe location. A transmembrane pressure of $\Delta P_{TMPD}=30$ kPa was maintained at any point along the fibres of the MBC module 802 in order to prevent gas bubbling. The amine solvent which has been used for $CO_2$ absorption in the MBC module 802 is called rich solvent and is collected using a rich amine tank 814.

Figure 9:
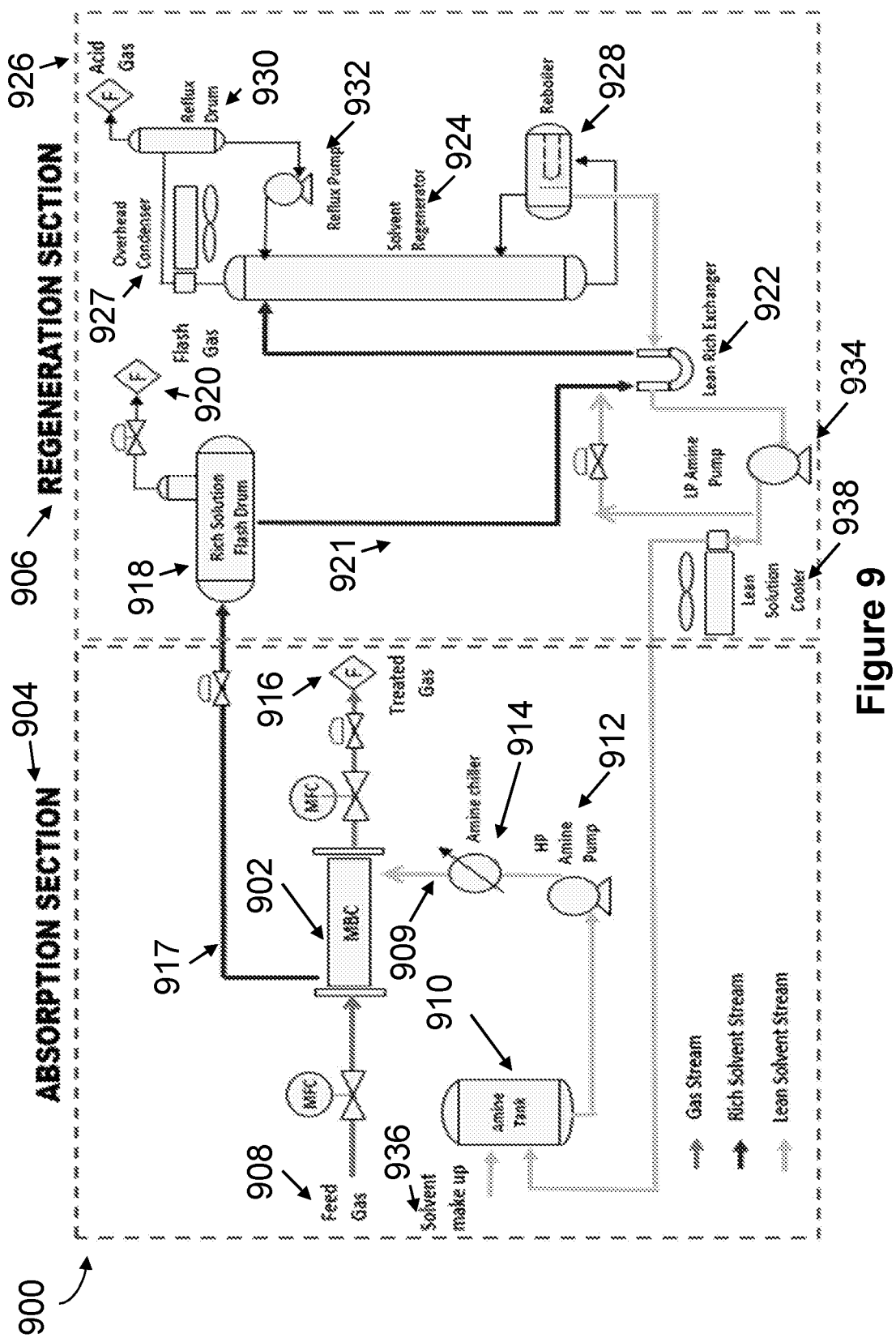
FIG. 9 is a schematic of a pilot natural gas (NG) plant set-up for carbon dioxide ($CO_2$) removal in a natural gas sweetening process using a hollow fibre membrane contactor (MBC) in accordance with an embodiment.

Separately, an experimental setup for pilot-scale testing was also arranged as shown in FIG. 9. FIG. 9 is a schematic 900 of a pilot natural gas (NG) plant set-up for carbon dioxide ($CO_2$) removal in a natural gas sweetening process using a horizontal hollow fibre membrane contactor (MBC) module 902 in accordance with an embodiment.

The NG plant set-up comprises an absorption section 904 and a regeneration section 906. At the absorption section 904, a feed gas 908 comprising $CO_2$-rich natural gas is fed to a tube side of the MBC 902, while the lean amine 909 was pressurized to ca. 54 bar in the amine tank 910 and fed to a shell side of the MBC module 902 using an amine pump 912 via an amine chiller 914, in a counter-current configuration to the feed gas 908. The feed gas flow rates and liquid flow rates were controlled using a mass flow controller and a pump stroke (not shown), respectively. The flowrate of the treated gas 916 at an MBC outlet was measured with a mass flowmeter before sending it to the flare header (not shown). The rich amine solvent 917 collected from the MBC shell outlet was directed to a flash drum 918 for degassing of any volatile and dissolved hydrocarbons. The gas compositions in the MBC feed and outlet as well as the flash outlet were analyzed and recorded using gas chromatography (e.g. PGC1000 Gas Chromatograph, ABB) after the set-up had reached steady state. A flash gas 920 is subsequently discharged from the flash drum 918 while a flash liquid outlet stream 921 outputted is heated by cross exchange with a hot lean solvent in a lean rich exchanger 922, and then fed to the solvent regenerator 924 where it was stripped of acid gas 926 by rising stream vapors generated by a reboiler 928. On the other hand, an overhead condenser 927 provides a reflux liquid stream to the column to ensure that the top-product stream (also known as acid gas stream) is as pure as possible. The top-product stream leaving the top of the regenerator was cooled and sent to a reflux drum 930 to separate the condensed water from the acid gas 926. The condensed water was then returned to the top of the solvent regenerator 924 via a reflux pump 932, while the acid gas 926 was sent to the flare header. Finally, solvent make-up 936 is fed from the reboiler 928 into the amine tank 910 using a low-pressure amine pump 934, via a lean solution cooler 938, to replenish the solvent evaporated in the MBC module 902, the flash drum 918, and the solvent regenerator 924. The solvent regeneration process is operated at low pressure to recover the HC and to lower the solvent boiling point in order to reduce energy consumption. A lower boiling point is also advantageous to keep the solvent below its degradation temperature.

In the present embodiment, the lab-scale set-up experiments were conducted with a binary feed gas mixture of $N_2/CO_2$ at 54 bar. The pilot-scale set-up was operated under industrially relevant operating conditions, also at 54 bar in a natural gas processing plant in Malaysia. In both cases, aqueous mixtures of methyldiethanolamine (MDEA) and piperazine (PZ) were used as the chemical solvent. The corresponding operating and design conditions in the lab and the pilot plant are summarized in Table 6.

TABLE 6

Operating and design conditions in the lab and pilot plant

| Parameters | $N_2/CO_2$ (Lab) | NG (Pilot) |
|---|---|---|
| $CO_2$ inlet, $y_{CO_2, g}^{in}$ [mol %] | 20-24 | 5-18 |
| MDEA/PZ inlet, [wt %] | 37/6 | 39/5 |
| Inlet gas pressure, $P_g^{in}$ [kPa] | 5400 | 5400 |
| Outlet liquid pressure, $P_l^{out}$ [kPa] | 5430 | 5430 |
| Gas mass flowrate, $M_g^{in}$ [kg h$^{-1}$] | 2-3 | 50-75 |
| Liquid volumetric flowrate, $F_l^{in}$ [L h$^{-1}$] | 8-10 | 175-275 |
| Gas temperature, $T_g^{in}$ [K] | 293 | 298 |
| Liquid temperature, $T_l^{in}$ [K] | 310-313 | 303-308 |
| $CO_2$ loading in solvent, $f_{CO_2, l}^{in}$ [mol mol$^{-1}$] | 0.01-0.23 | 0.01-0.23 |

The $CO_2$ loading was increased gradually during the experiments, starting with lean operation (where the $CO_2$ loading in the solvent at the MBC inlet, $f_{CO_2, l}^{in}=0.01$). This was achieved by reducing the heat input into the electrical reboiler 928 to obtain a higher $CO_2$ loading in the solvent in the present embodiment. Once the plant had reached a steady state at a particular reboiler energy duty, the lean amine was sampled and analyzed for its $CO_2$ content and loading before reducing the reboiler energy duty further. During the experiments, parameters such as $CO_2$ inlet, feed gas and amine flowrates were kept constant and the gas compositions in the MBC feed, outlet and the flash gas were analyzed and recorded using gas chromatography (e.g. PGC1000 Gas Chromatograph, ABB) every 6 minutes, after the set-up had reached steady state. In addition, pure $CO_2$ from a pack of cylinders was blended into the feed gas line to enable high $CO_2$ loading experiments (up to 18%). The fluid flowrates and gas compositions values were averaged hourly and compared with model predictions.

Figure 10C:
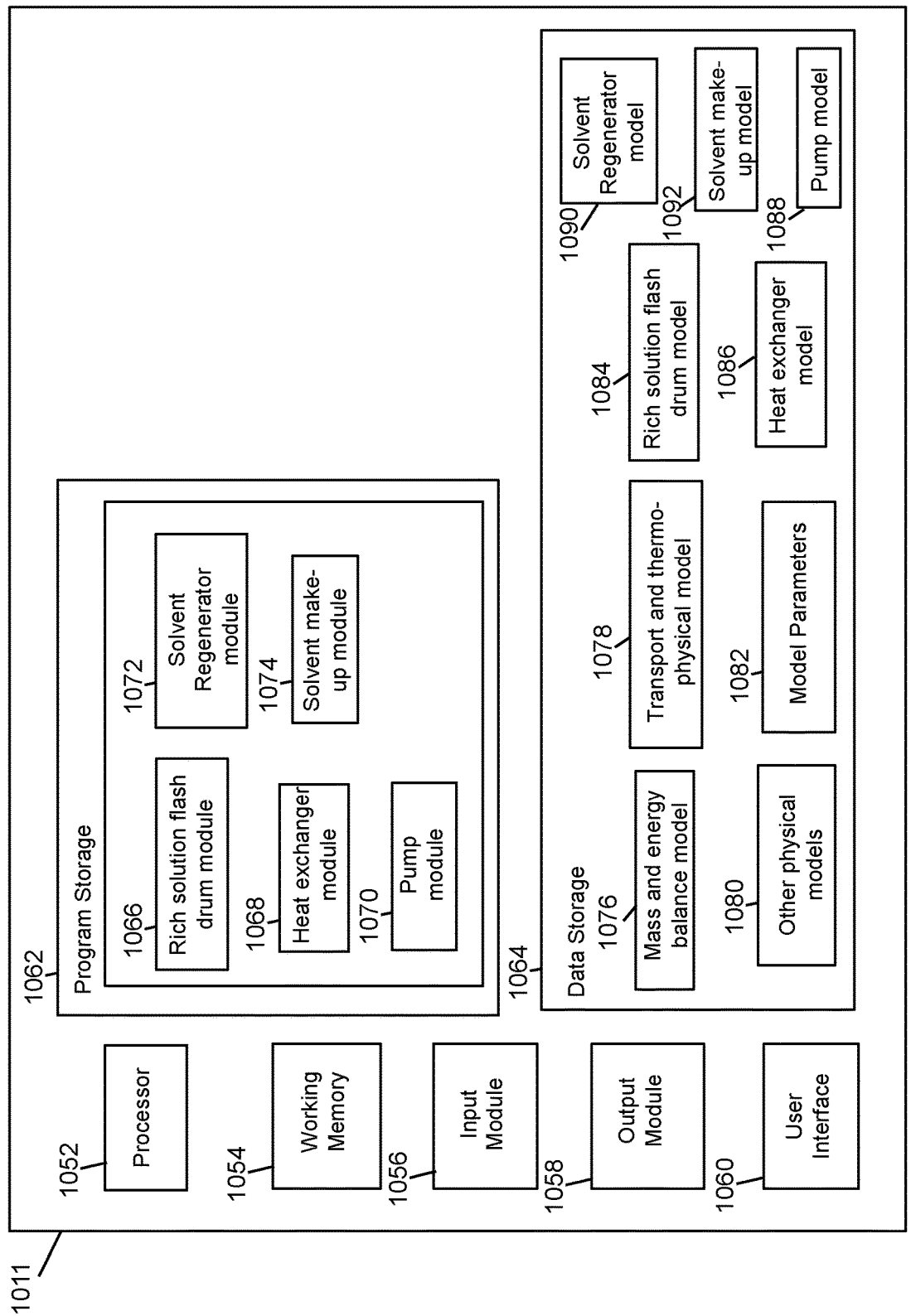

FIGS. 10A, 10B and 10C shows block diagrams of a natural gas sweetening process operating system 1000, a hollow fibre membrane contactor (MBC) data processing system 1010, and a solvent regenerate data processing system 1011 in accordance with an embodiment.

As shown in FIG. 10A, the natural gas sweetening processing operating system 1000 comprises the MBC data processing system 1010 and the solvent regeneration data processing system 1011, where the MBC data processing system 1010 is associated with absorption operations for acid gas absorption using e.g. the hollow fibre membrane contactor (MBC) 902 and the solvent regeneration data processing system 1011 is associated with desorption operations for solvent regeneration using e.g. the solvent regenerator 924. As will be understood by a skilled person, the natural gas sweetening processing operating system 1000 may comprise additional components such as a process, storage, input/output interfaces so that an operator can assess data from the natural gas sweetening processing operating system 1000 and/or control various components of the natural gas sweetening processing operating system 1000. These components are not shown for clarity and succinctness.

FIG. 10B is a block diagram showing the MBC data processing system 1010 in accordance with an embodiment. The MBC data processing system 1010 is a computer system with memory that stores computer program modules which implement computer-implemented method for assessing a MBC performance for a natural gas sweetening process in accordance with embodiments as described in relation to FIGS. 1-9 above. The MBC data processing system 1010 comprises a processor 1012, a working memory 1014, an input module 1016, an output module 1018, a user interface 1020, program storage 1022 and data storage 1024. The processor 1012 may be implemented as one or more central processing unit (CPU) chips. The program storage 1022 is a non-volatile storage device such as a hard disk drive which stores computer program modules such as a MBC computer module 1026. The computer program modules are loaded into the working memory 1014 for execution by the processor 1012. The input module 1016 is an interface which allows data, for example liquid flowrate of the solvent, gas flowrate of the natural gas etc. to be received by the MBC data processing system 1010. The output module 1018 is an output device which allows data and results of analysis of calculated model parameters by the MBC data processing system 1010 to be output, for example to the natural gas sweetening process operating system 1000. The output module 1018 may be coupled to a display device or a printer. The user interface 1020 allows a user of the MBC data processing system 1010 to input selections and commands and may be implemented as a graphical user interface.

The program storage 1022 stores the MBC computer module 1026. The MBC computer program module 1026 causes the processor 1012 to execute various MBC data processing which is described in more detail below. The program storage 1022 may be referred to in some contexts as computer readable storage media and/or non-transitory computer readable media. As depicted in FIG. 10B, the MBC computer module 1026 is a distinct module which perform respective functions implemented by the MBC data processing system 1010. It will be appreciated that the MBC computer module 1026 may be decomposed into sub-modules to be executed as multiple computer processes, and, optionally, on multiple computers. Moreover, alternative embodiments may combine multiple instances of a particular module or sub-module. It will also be appreciated that, while a software implementation of the computer program modules is described herein, these may alternatively be implemented as one or more hardware modules (such as field-programmable gate array(s) or application-specific integrated circuit(s)) comprising circuitry which implements equivalent functionality to that implemented in software.

The data storage 1024 stores various models, model data, and calculated and empirical model parameters. As shown in FIG. 10B, the data storage 1024 has storage for a MBC model 1028. In the present embodiment, the MBC model 1028 comprises a regression model for the Henry's constant of $N_2O$ ($H_{N2O,l}$) 1030 (discussed above in relation to FIGS. 7A and 7B), a regression model for the Henry's constant of hydrocarbons ($H_{i,l}$) 1032 (discussed above in relation to FIGS. 6A, 6B and 6C), a hydrocarbon loss rate model 1034 (discussed above in relation to the Equations 1 and 2), a MBC spatial model 1036 (discussed above in relation to FIGS. 1A, 1B and 2), a mass conservation model 1038 (e.g. as shown in Table 4 above), a material balances model 1040 (e.g. as shown in Table 4 above), boundary conditions 1042 (e.g. as shown in Table 4 above), transport and reaction kinetics model 1044 (as exemplified in the previous work "*Modeling for design and operation of high-pressure membrane contactors in natural gas sweetening*" in *Chemical Engineering Research and Design* 132, 1005-1019 (2018)), other physical models 1046 and model parameters 1048 (e.g. as shown in Table 5). In an embodiment, the MBC model 1028 may comprise a regression model for the Henry's constant of $CO_2$ ($H_{CO2,l}$) 1050. In this case, the Henry's constant of $CO_2$ can be determined directly from the regression model 1050 to account for $CO_2$ absorption in the solvent. This is described in relation to FIG. 11 below.

FIG. 10C is a block diagram showing the solvent regeneration data processing system 1011 in accordance with an embodiment. The solvent regeneration data processing system 1011 is associated with other modules involved in a plant-wide natural gas sweetening process which will be discussed in more detail below. Similar to the MBC data processing system 1010 as aforementioned described, the solvent regeneration data processing system 1011 is a computer system with memory that stores computer program modules. The solvent regeneration data processing system 1011 comprises a processor 1052, a working memory 1054, an input module 1056, an output module 1058, a user interface 1060, program storage 1062 and data storage 1064. The processor 1052 may be implemented as one or more central processing unit (CPU) chips. The program storage 1062 is a non-volatile storage device such as a hard disk drive which stores computer program modules. The computer program modules are loaded into the working memory 1054 for execution by the processor 1052. The input module 1056 is an interface which allows data, for example a pressure in a flash drum etc. to be received by the solvent regeneration data processing system 1011. The output module 1058 is an output device which allows data and results of analysis of calculated model parameters by the solvent regeneration data processing system 1011 to be output, for example to the natural gas sweetening process operating system 1000. The output module 1058 may be coupled to display device or a printer. The user interface 1060 allows a user of the solvent regeneration data processing system 1011 to input selections and commands and may be implemented as a graphical user interface.

The program storage 1062 stores a rich solution flash drum module 1066, a heat exchanger module 1068, a pump module 1070, a solvent regenerator module 1072, and a solvent make-up module 1074. These computer program modules cause the processor 1052 to execute various solvent regeneration data processing which is described in more detail below. The program storage 1062 may be referred to in some contexts as computer readable storage media and/or non-transitory computer readable media. As depicted in FIG. 10C, the computer program modules are distinct modules which perform respective functions implemented by the solvent regeneration data processing system 1011. It will be appreciated that the boundaries between these modules are exemplary only, and that alternative embodiments may merge modules or impose an alternative decomposition of functionality of modules. For example, the modules discussed herein may be decomposed into sub-modules to be executed as multiple computer processes, and, optionally, on multiple computers. Moreover, alternative embodiments may combine multiple instances of a particular module or sub-module. It will also be appreciated that, while a software implementation of the computer program modules is described herein, these may alternatively be implemented as one or more hardware modules (such as field-programmable gate array(s) or application-specific integrated circuit(s)) comprising circuitry which implements equivalent functionality to that implemented in software.

The data storage 1064 stores various model data and model parameters. As shown in FIG. 10C, the data storage 1064 has storage for a mass and energy balance model 1076, a transport and thermos-physical model 1078, other physical models 1080 and model parameters 1082 (e.g. as shown later in Tables 8 and 9). In an embodiment, the mass and energy balance model 1076, the transport and thermos-physical model 1078, other physical models 1080 and the model parameters 1082 can be obtained by interfacing with property packages, such as Advanced Peng Robinson, UNIQUAC-RK and RSKA for the gas and liquid phases in the absorption and regeneration unit from Multiflash v6.1 respectively. The data storage 1064 comprises a rich solution flash drum model 1084, a heat exchanger model 1086, a pump model 1088, a solvent regenerator model 1090, and a solvent make-up model 1092 for use with their corresponding modules. These models are described below in relation to FIG. 23.

Figure 13:
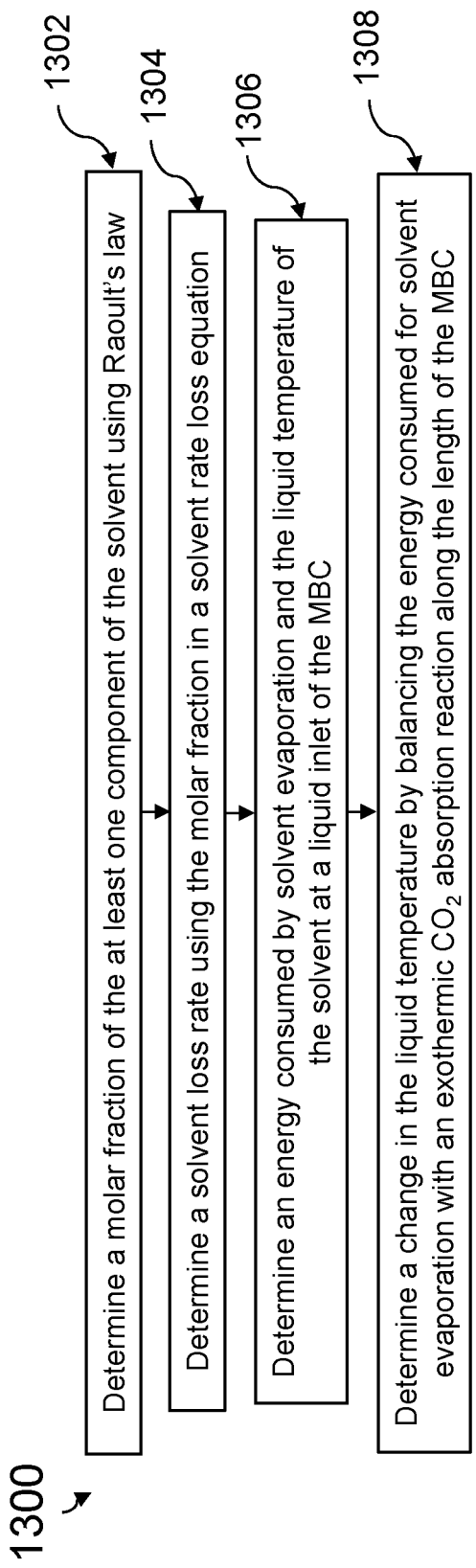
FIG. 13 is a flowchart showing a method for determining a solvent loss rate and a change in a liquid temperature of the solvent of the MBC in accordance with an embodiment.
Figure 14:
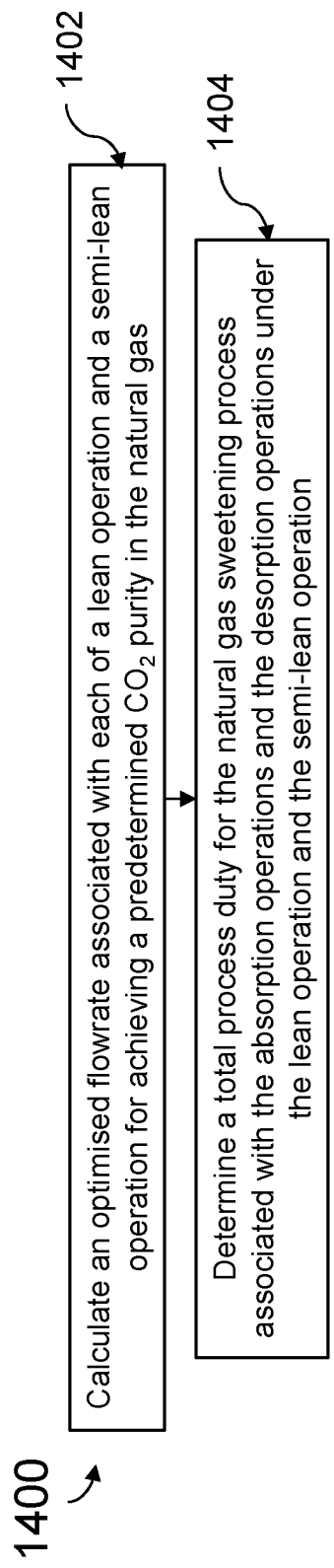
FIG. 14 is a flowchart showing steps of a method for determining a total process duty for the natural gas sweetening process under a lean operation and a semi-lean operation in accordance with an embodiment.

FIGS. 11 to 13 are flowcharts showing methods 1100, 1200 and 1300 which may be performed by the MBC data processing system 1010 in accordance with an embodiment, while FIG. 14 is a flowchart showing a method 1400 which may be performed by the natural gas sweetening process operating system 1000 in accordance with an embodiment.

Referring to the method 1100, in a step 1102, a regression model is formed using empirical data. The regression model for a Henry's constant of $CO_2$ may be formed using empirical data associated with $CO_2$ solubility in the solvent. In the present embodiment, the regression model for a Henry's constant of nitrous oxide ($N_2O$) is formed using empirical data of $N_2O$ solubility in the solvent. In this case, the regression model is a function of carbon dioxide ($CO_2$) loading and liquid temperature of the solvent. This is described above in relation to Equation 14. The solvent may comprise $H_2O$, MEDA and/or PZ in various percentages. An embodiment of the solvent comprises 50% aqueous MEDA.

In a step 1104, the Henry's constant of $CO_2$ is determined using the regression model. Where the regression model is formed using empirical data associated with $CO_2$ solubility in the solvent in accordance with an embodiment, the Henry's constant of $CO_2$ can be determined directly from the regression model. In the present embodiment where the regression model for the Henry's constant of $N_2O$ is formed, the Henry's constant of $CO_2$ is determined using the Henry's constant of $N_2O$. In this case, the Henry's constant of $N_2O$ is first determined using the regression model. The Henry's constant of $CO_2$ in the solvent is then calculated using the Henry's constant of $N_2O$ to account for $CO_2$ loading in the solvent. The Henry's constant of $CO_2$ may be determined using $N_2O$ analogy as illustrated by Equations 17 to 19 as described above.

In a step 1106, the determined Henry's constant of $CO_2$ is input in the MBC model 1028 as one of the model parameters 1048. The MBC model 1028 may comprise other models, for example, as shown in FIG. 10B.

In a step 1108, $CO_2$ absorption in the solvent is determined using the MBC model 1028 for designing and assessing the performance of the MBC.

FIG. 12 is a flowchart showing steps of a method 1200 for determining a loss rate of hydrocarbons in a solvent of the MBC in accordance with an embodiment.

In a step 1202, a regression model for a Henry's constant of a hydrocarbon in the solvent is formed using empirical data of the hydrocarbon solubility in the solvent to account for hydrocarbon loss from the natural gas to the solvent. This is described above in relation to Equation 13, Table 3 and FIGS. 6A, 6B and 6C above. As described in Equation 13, the regression model is a function of the liquid temperature, a liquid pressure of the solvent and a mass fraction of the at least one component in the solvent.

In a step 1204, the Henry's constant of the hydrocarbon in the solvent is determined using the regression model for the Henry's constant of the hydrocarbon.

In a step 1206, a loss rate of the hydrocarbon in the solvent is determined using the Henry's constant of the hydrocarbon in a hydrocarbon rate loss equation. The hydrocarbon rate loss equation is described above in relation to Equation 2. The loss rate of the hydrocarbon is a function of the concentration of the hydrocarbon as shown in Equation 2. The concentration of the hydrocarbon is in turn inversely proportional to the Henry's constant of the hydrocarbon in the solvent as shown and described in relation to Equation 1 above.

FIG. 13 is a flowchart showing a method 1300 for a solvent loss rate and a change in a liquid temperature of the solvent of the MBC in accordance with an embodiment.

In a step 1302, a molar fraction of the at least one component of the solvent in the gas outlet is determined using Raoult's Law. This is described in relation to Equation 3 above.

In a step 1304, a solvent loss rate is determined using the molar fraction in a solvent rate loss equation. This is described in relation to Equation 4 above. The solvent loss rate is proportional to the determined molar fraction as shown in Equation 4.

In a step 1306, an energy consumed for solvent evaporation and the liquid temperature of the solvent at a liquid inlet of the MBC are determined using the solvent loss rate determined in the step 1304. The energy consumed and the liquid/solvent temperature can be determined for example using Equations 5 and 6 as described above.

In a step 1308, a change in the liquid temperature is determined by balancing the energy consumed for solvent evaporation with an exothermic $CO_2$ absorption reaction under adiabatic conditions along the length of the MBC. This is described in relation to Equation 6 above. The Equation 6 above is now refined to be in a spatial distributed model and therefore advantageously introduces a spatial dimension for the change in the solvent temperature along the fibre length of the MBC.

FIG. 14 is a flowchart showing steps of a method 1400 for determining a total process duty for the natural gas sweetening process under a lean operation and a semi-lean operation in accordance with an embodiment. The method 1400 may be performed by the natural gas sweetening process operating system 1000 as described above and which modelling will be described in more detail below.

In a step 1402, an optimised flowrate associated with each of a lean operation and a semi-lean operation for achieving a predetermined $CO_2$ purity in the natural gas is calculated, the lean operation being an operation associated with using a lean solvent having less than 0.02 mol mol$^{-1}$ of $CO_2$ loading and the semi-lean operation being an operation associated with using a semi-lean solvent having more than 0.2 mol mol$^{-1}$ of $CO_2$ loading. This is described in relation to Table 11 below.

In a step 1404, a total process duty for the natural gas sweetening process associated with the absorption operations and the desorption operations under each of the lean operation and semi-lean operation is determined. This is described in relation to FIGS. 24A and 24B below.

Figures 15D, 15E:
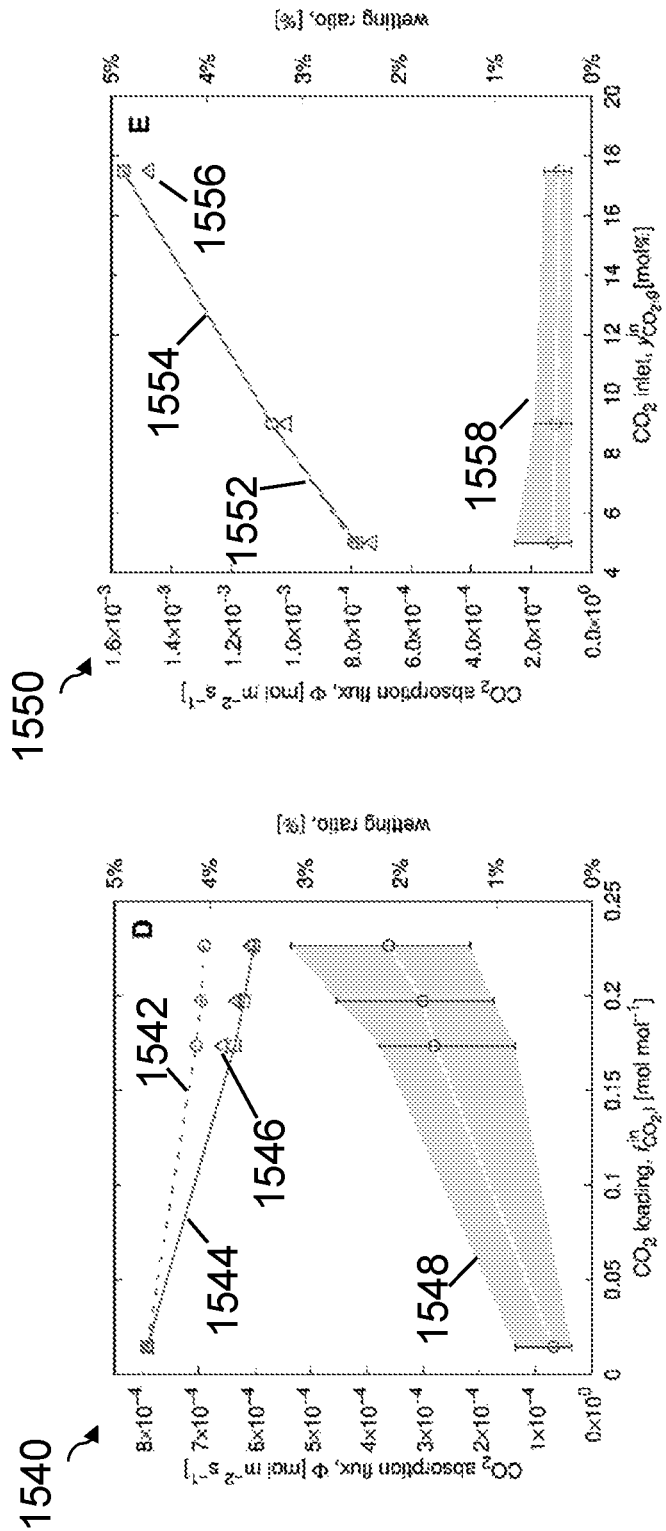

FIGS. 15A, 15B, 15C, 15D and 15E show graphs 1500, 1510, 1520, 1540, 1550 of predicted $CO_2$ absorption fluxes against experimental data for the lab-scale MBC set-up (FIGS. 15A-15C) and for the pilot NG plant set-up (FIGS. 15D and 15E) in accordance with an embodiment. FIG. 15A shows a graph 1500 of $CO_2$ absorption fluxes 1502, 1504, 1506 and predicted wetting ratio 1508 for different $CO_2$ loading for the lab-scale MBC set-up, FIG. 15B shows a graph 1510 of $CO_2$ absorption fluxes 1512, 1514, 1516 and predicted wetting ratio 1518 for different total gas flowrate for the lab-scale MBC set-up, FIG. 15C shows a graph 1520 of $CO_2$ absorption fluxes 1522, 1524, 1526 and predicted wetting ratio 1528 for different total liquid flowrate for the lab-scale MBC set-up, FIG. 15D shows a graph 1540 of $CO_2$ absorption fluxes 1542, 1544, 1546 and predicted wetting ratio 1548 for different $CO_2$ loading for the pilot NG plant set-up and FIG. 15E shows a graph 1550 of $CO_2$ absorption fluxes 1552, 1554, 1556 and predicted wetting ratio 1558 for different $CO_2$ inlet concentration in natural gas mixture for the pilot NG plant set-up. In particular, the $CO_2$ absorption fluxes 1502, 1512, 1522, 1542, 1552 are associated with predicted fluxes simulated under a lean solvent condition, the $CO_2$ absorption fluxes 1504, 1514, 1524, 1544, 1554 are associated with predicted fluxes simulate under a semi-lean solvent condition and the $CO_2$ absorption fluxes 1506, 1516, 1526, 1546, 1556 are associated with fluxes obtained from experimental data.

FIGS. 15A, 15B and 15C are described below in relation to the "Lab-scale MBC set-up" as discussed in relation to FIG. 8 and FIGS. 15D and 15D are described below in relation to the "Pilot-scale MBC set-up" section as discussed in relation to FIG. 9.

In particular, FIG. 15A shows an effect of $f_{CO_2,l}^{in}$ for fixed $M_g^{in}$=3 kg h$^{-1}$, $F_l^{in}$=10 L h$^{-1}$ and $y_{CO_2,g}^{in}$=20 mol %. FIG. 15B shows an effect of $M_g^{in}$ for a fixed $F_l^{in}$=10 L h$^{-1}$, $f_{CO_2,l}^{in}$=0.22 mol mol$^{-1}$ and $y_{CO_2,g}^{in}$=24 mol %. FIG. 15C shows an effect of $F_l^{in}$ for a fixed $M_g^{in}$=2 kg h$^{-1}$, $f_{CO_2,l}^{in}$=0.2 mol mol$^{-1}$ and $y_{CO_2,g}^{in}$=24 mol %. FIG. 15D shows an effect of $f_{CO_2,l}^{in}$ for fixed $M_g^{in}$=75 kg h$^{-1}$, $F_l^{in}$=275 L h$^{-1}$ and $y_{CO_2,g}^{in}$=5 mol %. FIG. 15E shows an effect of $y_{CO_2,g}^{in}$ for a fixed $f_{CO_2,l}^{in}$ of 0.01 mol mol$^{-1}$, $M_g^{in}$=50-75 kg h$^{-1}$, $F_l^{in}$=180-275 L h$^{-1}$. For the above terms, $f_{CO_2,l}^{in}$ refers to $CO_2$ loading of solvent at the inlet, $M_g^{in}$ refers to mass flowrate of the inlet gas, $F_l^{in}$ refers to an inlet volumetric solvent flowrate and $y_{CO_2,g}^{in}$ refers to the $CO_2$ mole fraction of the inlet gas.

Lab-Scale MBC Set-Up

As described above, comparisons between measured and predicted $CO_2$ absorption fluxes, Φ [mol m$^{-2}$ s$^{-1}$] are presented in FIGS. 15A, 15B and 15C, using the Henry's constant in Equation 14 that was regressed in both lean and semi-lean solvent. A comparison is also made with the predictions using Equation 15. The experimental data are for different $CO_2$ loadings in solvent (0.01-0.24 mol mol$^{-1}$) and different gas and amine flow rates (see Table 6). It can be seen that model predictions using Equation 14 are in close agreement with the experimental $CO_2$ fluxes. Predictions using Equation 15 are found to be in relatively good agreement with the measurements still, albeit showing larger and more systematic errors of up to 10% overestimation, particularly at higher $CO_2$ loading experiments. This systematic offsets between predictions and measurements is due to Equation 15 only accounting for lean amine, thereby overestimating the $CO_2$ solubility in the semi-lean solvent. Although Equation 14 predicted higher values of $H_{N_2O,l}$ by approximately 25% for the lean amine (see FIG. 7B), the effect on the $CO_2$ absorption flux is not as significant compared to higher $CO_2$ loading cases as shown in FIG. 15A. A possible explanation is that the diffusive mass transfer in the lean amine solution dominates over the $CO_2$ dissolution at the gas-liquid interface.

As evidenced in FIG. 15A, the MBC model 1028 correctly predicts that a larger $CO_2$ loading in the solvent feed decreases the $CO_2$ absorption flux. An increase in liquid $CO_2$ loading essentially results in a decrease in free amine available to react with $CO_2$. And, from a thermodynamics viewpoint, the solubility of $CO_2$ in the liquid decreases with an increase in the liquid $CO_2$ loading due to higher value of $H_{N_2O,l}$, thus higher $H_{CO_2,l}$ based on Equation 15 (see also FIG. 7B). The model 1028 predicts an average wetting in the range between 2 to 6% as the $CO_2$ loading varies. In particular, an increase in $CO_2$ loading increases membrane wetting due to the reduction in liquid surface tension, as per Young-Laplace equation, thereby causing a reduction of the $CO_2$ flux through the membrane.

From FIG. 15B, it is shown that the MBC model 1028 also correctly predicts the increase in $CO_2$ absorption flux with a larger inlet gas flowrate, driven by a larger amount of $CO_2$ in the gas feed. Note that, since the pressure drops in the tubes is negligible, increasing the inlet gas flowrate has minimal effect on the wetting ratio (a mere increase of 0.2% wetting here).

As shown in FIG. 15C, the MBC model 1028 correctly captures the improvement in $CO_2$ absorption flux on increasing the solvent flowrate, with a corresponding small decrease in the membrane wetting. An increase of liquid/solvent flowrate leads to a higher pressure drop, transmembrane pressure and membrane wetting. But at a higher liquid flowrate, the temperature increase in the solvent due to a higher $CO_2$ absorption is lower, which results in a relatively higher liquid surface tension, and therefore a lower membrane wetting. On balance, the MBC model 1028 correctly predicts that the effect of a higher pressure drop on membrane wetting is small in comparison with the increase in liquid surface tension. The effect of a larger concentration gradient due to an increase in velocity also contributes to increasing the overall $CO_2$ absorption.

Figure 16:
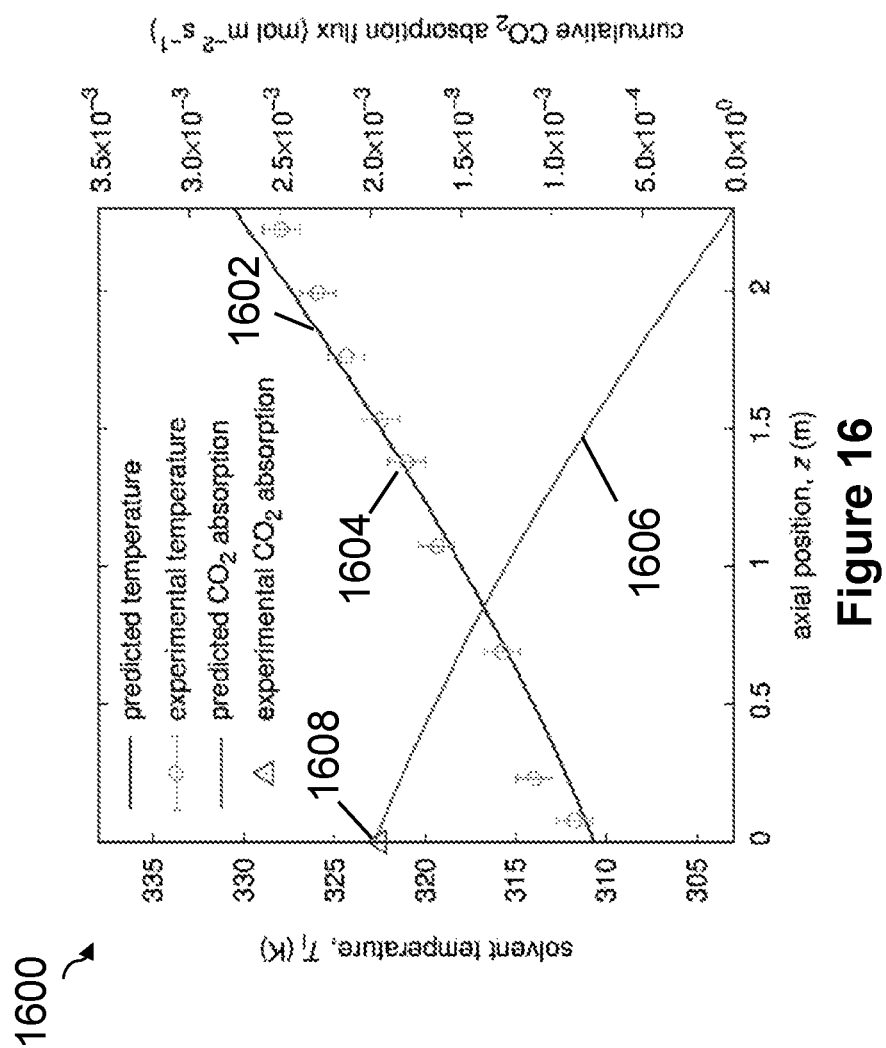
FIG. 16 shows a graph of predicted and experimental solvent temperature and $CO_2$ absorption for different axial positions along the length of the MBC in accordance with an embodiment.

FIG. 16 shows a graph 1600 of predicted and experimental solvent temperature and $CO_2$ absorption for different axial position along the length of the MBC 802, 902 along the module length for gas and solvent flowrates and $CO_2$ loading of 2 kg h$^{-1}$, 10 L h$^{-1}$ and 0.22 mol mol$^{-1}$ respectively, in accordance with an embodiment. FIG. 16 shows plots of predicted temperature 1602, empirical temperature data 1604 obtained from experiments, predicted $CO_2$ absorption flux 1606 and experimental $CO_2$ absorption flux 1608.

As shown in FIG. 16, the predicted solvent temperature profile 1602 along the fibre length is in excellent agreement with the measured solvent temperature 1604, which provides a first validation of the assumption made in the energy balance as described above in relation to Equations 5 and 6. In this experiment, it appears that there is no significant temperature bulge in the MBC module 802, 902. The model 1028 can be used to identify potential temperature bulge along the MBC length at different operating conditions. Notice also that the temperature rise (ca. 20 K) in the MBC module 802, 902 is significant where a L/G ratio (ca. 0.86 m$^3$ kmol$^{-1}$) was comparable to values of 0.6-1.1 m$^3$ kmol$^{-1}$ typically encountered in conventional packed column.

The predicted cumulative $CO_2$ absorption flux 1606 in FIG. 16 is 0 at the gas inlet (z=2.3 m) and increases along the fibre axis. The $CO_2$ absorption flux presents a slow decrease from the gas inlet to the gas outlet (concave shape), which is expected since the higher $CO_2$ concentration near the gas inlet enhances the mass transfer of $CO_2$ through the membrane. Likewise, the temperature rise is higher near the gas inlet (convex shape) due to more heat released being released from the $CO_2$ absorption in amine solvent.

Pilot-Scale MBC Module

A similar comparison between measured and predicted $CO_2$ absorption fluxes 1542, 1544, 1546, 1552, 1554, 1556 in the pilot-scale MBC module is presented in FIGS. 15D and 15E. The experimental data are for different $CO_2$ loadings in solvent (0.01-0.23 mol mol$^{-1}$) and different gas and amine flow rates (see e.g. Table 6). The model predictions using Equation 14 to predict $CO_2$ solubility are in close agreement with the $CO_2$ absorption fluxes in FIG. 15D, while the predictions using Equation 15 result in a similar 10% overestimation at higher $CO_2$ loading experiments, due to neglecting the effect of $CO_2$ loading in amine solvent.

Consistent with lab-scale results, the MBC model 1028 correctly predicts that a larger $CO_2$ liquid loading reduces the $CO_2$ absorption flux due to a decrease in free amine available to react with $CO_2$. This is for example shown in FIG. 15D. Moreover, an increase in the $CO_2$ liquid loading decreases the solubility of $CO_2$ in the liquid (see e.g. FIG. 7B) and the liquid surface tension, thereby causing extra wetting and therefore a reduction in the $CO_2$ flux through the membrane.

Experimental data corresponding to different $CO_2$ inlet concentration in NG mixture and a lean amine are considered in FIG. 15E. The MBC model 1028 correctly captures again the improvement in $CO_2$ absorption flux 1552, 1554 on the increasing $CO_2$ inlet concentration. This improvement is driven by the higher $CO_2$ concentration gradient which increases mass transfer in MBC. The MBC model 1028 also predicts a negligible membrane wetting due to the horizontal orientation and operation with a lean amine.

Estimation of Hydrocarbon Lost in High-Pressure MBC for NG Sweetening

Figure 17:
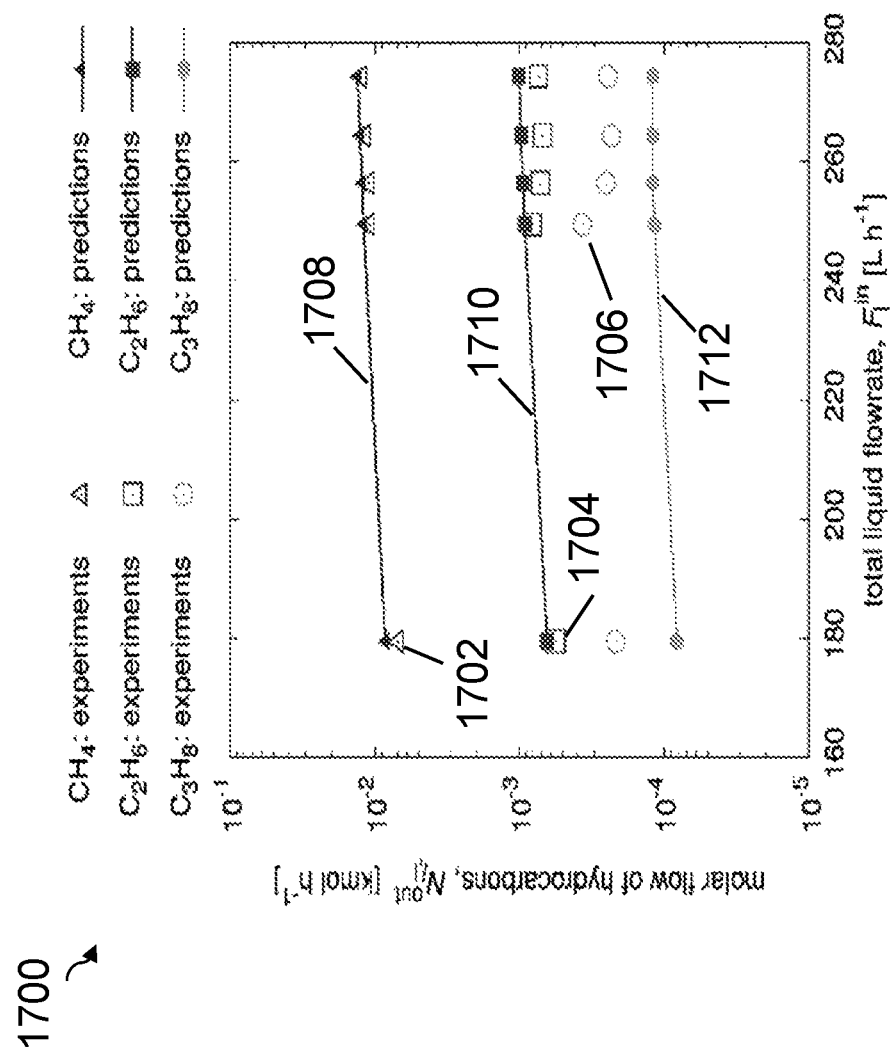
FIG. 17 shows a graph of predicted and experimental hydrocarbon molar flowrates in flashed gas for the pilot NG plant for different liquid flowrates in accordance with an embodiment.

FIG. 17 shows a graph 1700 of experimental and predicted hydrocarbon molar flowrates in the flashed gas for the pilot NG plant for different solvent flowrates in accordance with an embodiment. In particular, FIG. 17 shows plots of an experimental flowrate for $CH_4$ 1702, an experimental flowrate for $C_2H_6$ 1704, an experimental flowrate for $C_3H_8$ 1706, a predicted flowrate for $CH_4$ 1708, a predicted flowrate for $C_2H_6$ 1710, and a predicted flowrate for $C_3H_8$ 1712. The gas inlet flowrate, $CO_2$ inlet content and solvent inlet $CO_2$ loading were 75 kg h$^{-1}$, 5 mol % and 0.01 mol mol$^{-1}$ respectively.

Referring to FIG. 17, it can be seen that all of the predicted molar flows 1708, 1710 for methane and ethane are within 15% of the measurements. This validates the assumption that the solvent is about saturated with hydrocarbons at the MBC liquid outlet as described above in relation to Equation 1. On the other hand, the predicted molar flows of propane 1712 underestimates the measurements by a factor of 2 to 3, which could be due to these flowrates are relatively small, therefore are susceptible to experimental error.

Further, as shown in FIG. 17, the MBC model 1028 correctly captures the increase in HC absorption on increasing the solvent flowrate against experimental data, as described in Equation 2. The increase in HC absorption is attributed to a higher concentration gradient in the solvent, which improves mass transfer. The MBC model 1028 further predicted that the methane losses are an order of magnitude higher than ethane and higher hydrocarbon losses. This was expected as the feed gas to the pilot plant contains 85 mol % of methane, and that methane has a higher solubility of in amine than ethane and higher hydrocarbons (see FIGS. 6A, 6B and 6C). Overall, the predictions provide the correct order of magnitude for the HC loss with small loss rates of ca. 1% for the experimented solvent flowrates. Therefore, similar modelling approach will be used in a techno-economic assessment as discussed later.

Estimation of Solvent Evaporation Rate in High Pressure MBC for NG Sweetening

TABLE 7

Predicted component flowrates of the treated gas from MBC for a $CO_2$ loading, gas and solvent flowrates of 0.01 mol mol$^{-1}$, 75 kh h$^{-1}$ and 275 L h$^{-1}$, respectively.

| Variable | Value at time 0.00000 | Units |
| --- | --- | --- |
| Mass flowrate | 0.0181556 | kg/s |
| Molar flowrate | 3.65714 | kmol/h |
| Volumetric flowrate | Data not available | m$^3$/s |
| Component mass flowrate ("H$_2$O") | 1.69693E-05 | kg/s |
| Component mass flowrate ("MDEA") | 5.26213E-09 | kg/s |
| Component mass flowrate ("PZ") | 2.30352E-07 | kg/s |
| Component mass flowrate ("CO$_2$") | 4.33188E-05 | kg/s |
| Component mass flowrate ("methane") | 0.0146604 | kg/s |
| Component mass flowrate ("ethane") | 0.00209891 | kg/s |
| Component mass flowrate ("propane") | 0.00133579 | kg/s |

TABLE 7-continued

Predicted component flowrates of the treated gas from MBC for a $CO_2$ loading, gas and solvent flowrates of 0.01 mol mol$^{-1}$, 75 kh h$^{-1}$ and 275 L h$^{-1}$, respectively.

| Variable | Value at time 0.00000 | Units |
| --- | --- | --- |
| Component molar flowrate ("H$_2$O") | 0.00339104 | kmol/h |
| Component molar flowrate ("MDEA") | 1.58977E-07 | kmol/h |
| Component molar flowrate ("PZ") | 9.62743E-06 | kmol/h |
| Component molar flowrate ("CO$_2$") | 0.00354346 | kmol/h |
| Component molar flowrate ("methane") | 3.28985 | kmol/h |
| Component molar flowrate ("ethane") | 0.251291 | kmol/h |
| Component molar flowrate ("propane") | 0.109005 | kmol/h |

Figure 18:
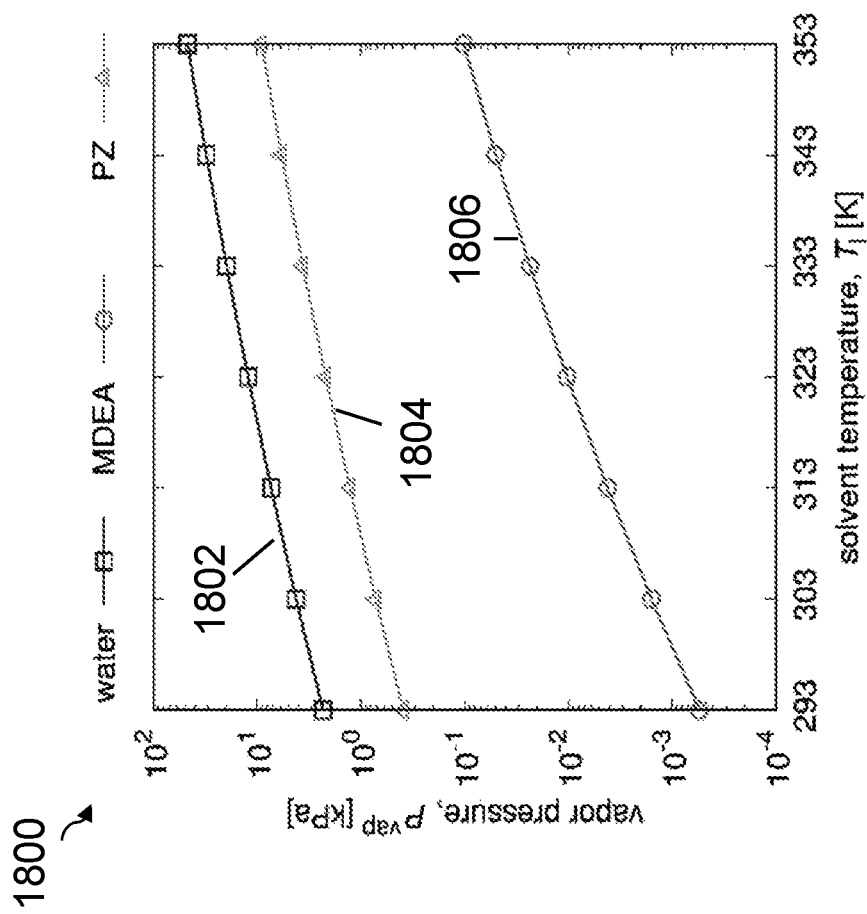
FIG. 18 shows a graph of predicted vapour pressure of water, MDEA and PZ against different solvent temperature from 293K to 353K in accordance with an embodiment.

FIG. 18 shows a graph 1800 of predicted vapour pressure of water 1802, MDEA 1804 and PZ 1806 against different solvent temperature from 293K to 353K, in accordance with an embodiment.

As shown in Table 7 above, the MBC model 1028 predicts that water is predominantly evaporated while the evaporation rates of MDEA and PZ to the treated gas are negligible. This is attributed to the vapor pressures of MDEA and PZ being much lower compared to that of water in the temperature of 293-353 K (see FIG. 18) as well as their concentrations.

The low solvent evaporation rate is due to the fact that at higher operating pressure (54 bar), the molar fraction $y_{i,g}^{out}$ of solvent in the treated gas outlet, is 50 times smaller compared to atmospheric pressure (see Equation 3). For an MBC operating at atmospheric pressure, such as in post-combustion $CO_2$ capture, one can expect much higher solvent evaporation losses, hence the need to model solvent evaporation in a more detailed manner. For a high-pressure MBC used in NG sweetening, the assumptions of using Raoult's Law (see in relation to Equation 3) by means of overall mass balance (lumped) are justified since the evaporation rate is low.

The MBC model 1028 predicts that about 0.03 wt % of the solvent flowrate fed to the MBC is lost by evaporation in the pilot plant. The corresponding energy consumed by this solvent evaporation in the MBC is less than 1% of the heat generated by the $CO_2$ absorption. This confirms that solvent evaporation has a minimal impact on the solvent temperature at high pressure and validates the approximation of accounting for solvent evaporation at the liquid inlet in the MBC energy balance (see in relation to Equations 5 and 6). Overall, the ability to predict the solvent evaporation rate and its composition will enable quantifying the amount of solvent make-up required and will feed into the process-wide assessment of MBC for NG sweetening as discussed below.

With the developed MBC model 1028 (i.e. absorption section) above, it can now be integrated with the solvent regeneration model/unit (i.e. desorption section) for the development of a full-scale MBC based NG sweetening process operation model as will be discussed below. This integration will make it possible to analyze the effects of different conceptual designs, including various absorption/desorption design configurations and operational decisions for process scale-up and process-wide economic assessment. The integration of the MBC model 1028 into a complete process model describing both $CO_2$ absorption and desorption operations enables a model-based assessment of a full-scale MBC process for NG sweetening.

Process-Wide Modeling and Assessment of Natural Gas Sweetening Using High-Pressure Membrane Contactors A conventional NG sweetening process comprises two operations—absorption and desorption (also known as solvent regeneration). In the absorption process, the lean or semi-lean solvent, most commonly alkanolamines, flows counter-currently with the natural gas in the MBC module 802, 902 and selectively reacts with the acid gasses ($CO_2$ and $H_2S$) from the gas phase. For bulk $CO_2$ removal, the $CO_2$ purity target is typically sales gas specification with a $CO_2$ content lower than 2 mol % or 6-8 mol % when the $CO_2$ content at the feed gas is higher than 20 mol %. For deep $CO_2$ removal applications in liquefied natural gas (LNG) plants and ammonia plants, the $CO_2$ specifications are <50 ppmv and <100 ppmv, respectively, to avoid freezing in low-temperature chillers (liquefaction process) and catalyst poisoning.

The terms lean and semi-lean refer to the fraction of acid gasses present in the amine solvent. In the context of $CO_2$ capture in the present embodiments, "lean" solvent refers to an inlet solvent stream containing little or no $CO_2$ (i.e., $CO_2$ loading ca. 0.01 mol $mol^{-1}$), while "semi-lean" indicates that the amine contains some $CO_2$ (i.e., $CO_2$ loading ca. 0.2 mol $mol^{-1}$). The solvent stream coming out of the MBC is termed "rich", and it needs to undergo regeneration, which consists of a combination of flash stages and a gas-liquid contacting column.

In a solvent regeneration process as previously described in relation to FIG. 9, the rich amine solvent 917 from the MBC liquid outlet is first directed to a lower pressure flash drum 918 to recover the flashed HC as fuel gas 920. The liquid outlet stream from the flash drum 918 is then fed to the solvent regenerator 924, where it is heated by the reboiler 928 to a suitable temperature to strip off $CO_2$ from the rich solvent before recycling the lean solvent to the MBC unit 902. On the other hand, the overhead condenser 927 provides a reflux liquid stream to the solvent regenerator 924 to ensure that the top-product stream (also known as acid gas stream) is as pure as possible. Finally, solvent make-up feeds into the amine tank 910 to replenish the solvent evaporated in the MBC module 902, flash drum 918, and solvent regenerator 924. The solvent regeneration process is operated at low pressure to recover the HC and to lower the solvent boiling point in order to reduce energy consumption. A lower boiling point is also advantageous to keep the solvent below its degradation temperature. Typically, the reboiler 928 of the solvent regeneration process is the largest contributor to the operating cost.

Some key performance indicators (KPIs) for the NG sweetening process are: (a) the $CO_2$ purity in the product gas; (b) the energy per ton of $CO_2$ removed; (c) the amount of HC loss or recovered as fuel gas; and (d) the amount of solvent loss per treated gas and makeup required.

Using an integrated model which comprises the aforementioned MBC model 1028, the $CO_2$ removal performance and the energy duty for each equipment under various scenarios, including lean and semi-lean process operation can be predicted. The amount and the composition of hydrocarbons (HC) recovered in the flash drum at various pressures can also be quantified. In addition, the evaporative solvent losses in the MBC module 802, 902 and solvent regeneration sections can be predicted, so that the solvent makeup required to maintain the solvent concentration in the process can be quantified with the relevant costs estimated. The predictive capability of the integrated model 1000 in terms of $CO_2$ removal performance and energy consumptions will be tested against data from a pilot-scale MBC module operated at variable $CO_2$ loading in the amine solvent, at a NG processing plant in Malaysia. In the present embodiments, all experiments were conducted with aqueous mixtures of MDEA and piperazine (PZ) as the chemical solvent.

The experimental set-ups of the pilot-scale MBC based NG sweetening process, and the corresponding model parameters are presented below, followed by a description of the development and implementation of the MBC process-wide model. Results of the experimental verification of the process-wide model are then presented and discussed. A model-based analysis is conducted to investigate the effect of (i) optimised lean and semi-lean MBC operations on energy duty, (ii) different operating pressures on HC recovery in the rich solution flash drum, and (iii) different inlet solvent temperatures on the evaporative solvent losses. A model-based design and scale-up of a commercial-scale MBC is conducted for a semi-lean MBC process operating under industrially relevant conditions for NG sweetening and its intensification potential is assessed.

Pilot-Scale MBC Setup

Experiments were conducted in pilot-scale module operated under industrially relevant operating conditions at 54 bar in a NG processing plant in Malaysia. Aqueous mixtures of methyl diethanolamine (MDEA) and piperazine (PZ) were used as the chemical solvent. This experimental setup is similar to the pilot-scale description above in relation to FIG. 9 and is therefore not repeated here. The corresponding operating conditions for the absorption and desorption system are summarized in Table 8 below. The flows and compositions of the gas at the MBC inlet and outlet, of the regenerated solvent, and of the flash gas were measured and averaged hourly for comparison with model predictions. The energy consumption of all the units which was powered by electricity was monitored. The pieces of equipment considered for the total energy consumption or known as process duty, $P_T$ [kW] are the (i) reboiler 928, (ii) overhead condenser 927, (iii) reflux pump 932, (iv) LP amine pump 934 (v) lean solution cooler 938 (vi) HP amine pump 912, and (vii) amine chiller 914. These equipment are modelled as discussed below, where each form one of the modules stored in the program storage 1062 of the solvent regeneration data processing system 1011.

Module Specification

The high-pressure MBC module 802, 902 was packed with hydrophobic, Polytetrafluoroethylene (PTFE) hollow fibre in the present embodiments, which is identical to the module used above in relation to Table 2. The solvent regenerator (for example the solvent regenerator 924 as shown in FIG. 9) was packed with Raschig Super-Ring #1 material in accordance with the present embodiments. Table 8 below summarizes the main characteristics and geometrical properties of both the MBC and solvent regeneration units.

TABLE 8

Operating conditions in the pilot plant.

| Parameters | Natural Gas |
| --- | --- |
| MBC (Absorption) | |
| $CO_2$ inlet, $y_{CO_2, g}^{in}$ [mol %] | 5 |
| $CH_4$, $C_2H_6$, $C_3H_8$ inlet, [mol %] | 85/7/3 |
| MDEA/PZ inlet, [wt %] | 39/5 |
| Inlet gas pressure, $P_g^{in}$ [kPa] | 5400 |
| Outlet liquid pressure, $P_l^{out}$ [kPa] | 5430 |
| Gas mass flowrate, $M_g^{in}$ [kg $h^{-1}$] | 75 |
| Liquid volumetric flowrate, $F_l^{in}$ [L $h^{-1}$] | 275 |
| Gas temperature, $T_g^{in}$ [K] | 301-308 |

TABLE 8-continued

Operating conditions in the pilot plant.

| Parameters | Natural Gas |
|---|---|
| Liquid temperature, $T_l^{in}$ [K] | 308-313 |
| $CO_2$ loading in solvent, $f_{CO_2, l}^{in}$ [mol mol$^{-1}$] | 0.01-0.24 |
| Solvent Regeneration (Desorption) | |
| Rich solution drum pressure, [kPa] | 911 |
| Solvent regenerator pressure, [kPa] | 258 |
| Reboiler temperature, [K] | 403 |
| Overhead condenser-Outlet [K] | 333 |
| Reflux pump pressure-Outlet [kPa] | 258 |
| Lean-rich exchanger | |
| Cold stream-Inlet/Outlet [K]/[kPa] | 352/371/368 |
| Hot stream-Inlet/Outlet [K]/[kPa] | 382/364/233 |
| LP amine pump pressure-Outlet [kPa] | 711 |
| Lean solution cooler-Outlet [K] | 318 |
| Pressure drop [kPa] | 35 |
| Amine HP pump pressure-Outlet [kPa] | 5460 |
| Amine chiller-Outlet, [K] | 308 |
| Pressure drop [kPa] | 30 |

TABLE 9

Specifications of the MBC and solvent regeneration units.

| Parameter | Value | Source |
|---|---|---|
| MBC (Absorption) | | |
| Fibre length, L [m] | 2.3 | (PRSB, 2016) |
| Fibre inner radius, $r_1$ [μm] | 225 | (PRSB, 2016) |
| Fibre outer radius, $r_2$ [μm] | 550 | (PRSB, 2016) |
| Membrane porosity, ε [—] | 0.41 | (PRSB, 2016) |
| Membrane tortuosity, τ [—] | 6.1 | Sec. 4.3.2 |
| Max. pore radius, $\delta_{max}$ [μm] | 0.18 | (PRSB, 2016) |
| Mean pore radius, $\bar{\delta}$ [μm] | 0.06 | Sec. 4.3.2 |
| Pore standard deviation, σ [—] | 0.24 | Sec. 4.3.2 |
| Contact angle, θ [°] | 92.4 | (PRSB, 2016) |
| Packing density, ∅ [—] | 0.38 | Sec. 4.3.3 |
| Module inner radius, $R_m$ [m] | 0.115 | (PRSB, 2016) |
| Membrane area, $A_m$ [m$^2$] | 68 | Sec. 4.3.3 |
| No of fibres, N [—] | 8400 | (PRSB, 2016) |
| Specific surface area [m$^{-1}$] | 1600 | (PRSB, 2016) |
| Outer radius of steel tube, $R_t$ [m] | 0.08 | Sec. 4.3.3 |
| Conventional Solvent Regenerator (Desorption) | | |
| Packing size, [m] | 0.025 | (Honeywell UOP, 2014) |
| Packing height/diameter, [m] | 6.1/0.3 | (Honeywell UOP, 2014) |
| Surface area, [m$^2$/m$^3$] | 150 | (Honeywell UOP, 2014) |
| Void fraction, [—] | 0.98 | (Honeywell UOP, 2014) |
| Loading point constant, $C_s$ [—] | 3.491 | (Billet and Schultes, 1999) |
| Flooding point constant, $C_{FL}$ [—] | 2.2 | (Billet and Schultes, 1999) |
| Hydraulic constant, $C_h$ [—] | 0.75 | (Billet and Schultes, 1999) |
| Total particles constant, $C_{P0}$ [—] | 0.5 | (Billet and Schultes, 1999) |
| Liquid constant, $C_L$ [—] | 1.29 | (Billet and Schultes, 1999) |
| Vapor constant, $C_v$ [—] | 0.44 | (Billet and Schultes, 1999) |

Note:
the reference values above are taken from (i) Honeywell UOP (2014) 'Regeneration Section for PETRONAS $CO_2$ Pilot Plant' and (ii) Billet, R. and Schultes, M. (1999) 'Prediction of mass transfer columns with dumped and arranged packings', Trans IChemE, 77. pp. 501. doi 10.1205/026367699526520.

Modelling of MBC-Based Process for NG Sweetening

The modelling of the regeneration unit operations in the MBC process, namely the flash drum 918, heat exchangers 922, pumps 932, 934, and stripping column 924 based on the MBC pilot-plant set up are now described. Their integration with the MBC unit model 1028 developed above was conducted in the gPROMS ProcessBuilder environment for the present embodiments, although the gPRMOS Process-Builder environment was used here, it is appreciated that other relevant programs or software can be used for the integration. The models of the regeneration unit operations as described, together with the MBC model 1028 form a NG plant-wide model of the natural gas sweetening process operating system 1000 for assessing a performance or characteristics of the natural gas sweetening process.

Figure 19:
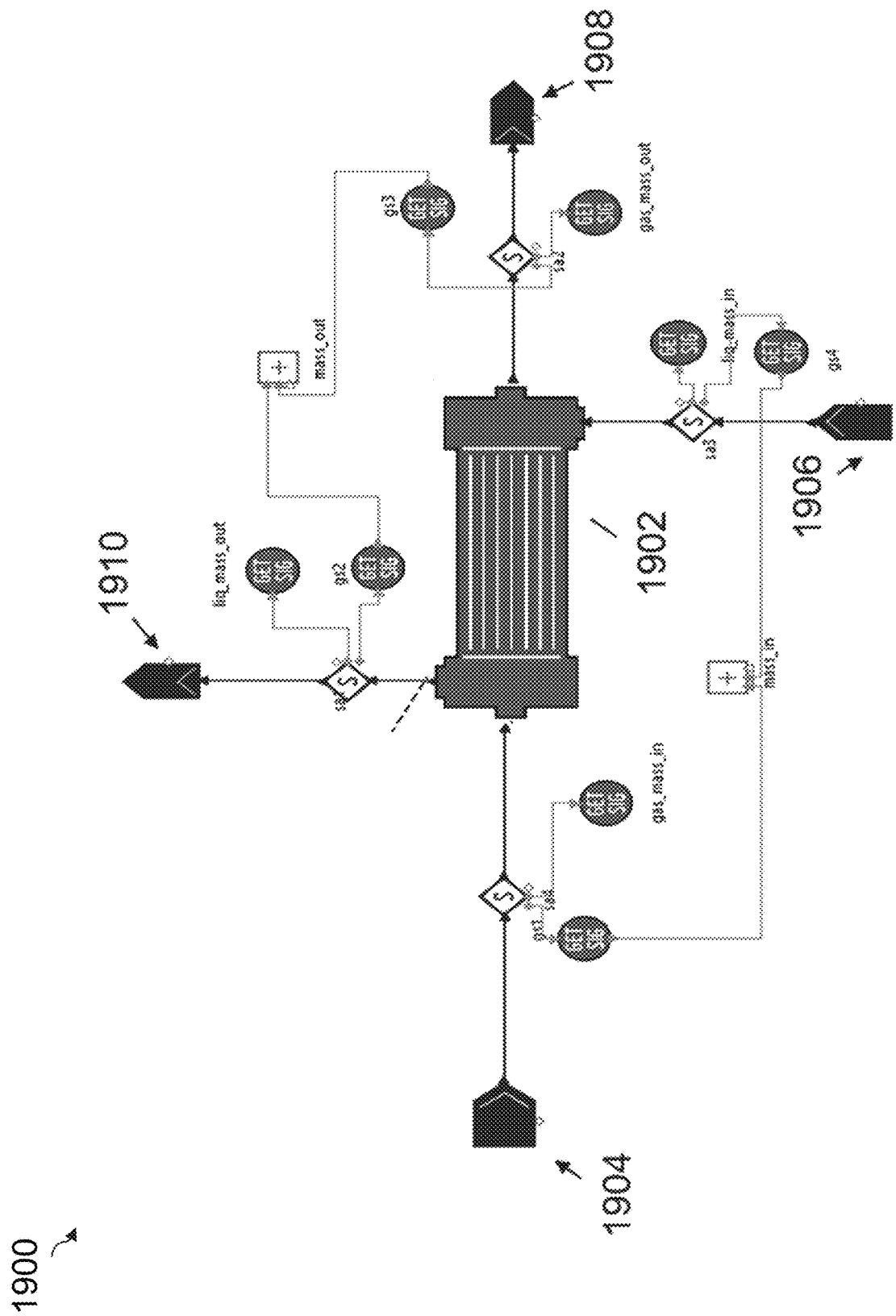
FIG. 19 shows a schematic of a gML-compliant MBC unit operation model in gPROMS ProcessBuilder for modelling the natural gas sweetening process in accordance with an embodiment.

FIG. 19 shows a schematic 1900 of a gML-compliant MBC unit operation model in gPROMS ProcessBuilder for modelling the natural gas sweetening process in accordance with an embodiment. As shown in FIG. 19, the MBC unit operation model comprises a MBC module 1902 having a gas inlet 1904 for natural gas, a liquid inlet 1906 for a solvent (for example an amine solvent), a gas outlet 1908 for treated natural gas, and a liquid outlet 1910 for rich solvent (i.e. solvent which was used for $CO_2$ absorption in the MBC module 1902). The parameters used in the gML-compliant MBC unit operation model are shown below in Table 10. The schematic 1900 shows a user interface of the MBC unit operation model which was compiled into a gML-compliant model library.

TABLE 10

Parameters used in the gML-compliant MBC unit operation model in gPROMS ProcessBuilder units.

| Parameters | Value | Units |
|---|---|---|
| Gas inlet | 2.0 | kg/hour |
| Liquid outlet | 11 | kg/hour |
| Molar fraction of $CO_2$ in | 0.239000 | — |
| Molar fraction of $CO_2$ out | 0.06128 | — |
| $CO_2$ removal % | 79.51 | % |
| $CO_2$_loading_LA_calc | 0.2252 | kmol_$CO_2$/kmol_amine |
| $CO_2$_loading_RA | 0.5475 | kmol_$CO_2$/kmol_amine |
| Liquid to $CO_2$ absorbed | 103.8 | gal/lb · mol |
| Average wetting ratio | 0.0472 | — |
| Average absorption flux_$CO_2$ | 0.00198296 | mol/m$^2$s |
| Liquid temperature at inlet | 311 | K |
| Liquid temperature at outlet | 330 | K |
| ΔT of liquid | 19.8 | K |
| Total mass in (1) | 0.003328 | kg/s |
| Total mass out (1) | 0.003328 | kg/s |
| Gas mass in ("Mass flowrate", 1) | 0.0005500 | kg/s |
| Gas mass out ("Mass flowrate", 1) | 0.0004015 | kg/s |
| Liquid mass in ("Mass flowrate", 1) | 0.002778 | kg/s |
| Liquid mass out ("Mass flowrate", 1) | 0.002926 | kg/s |

Figure 20:
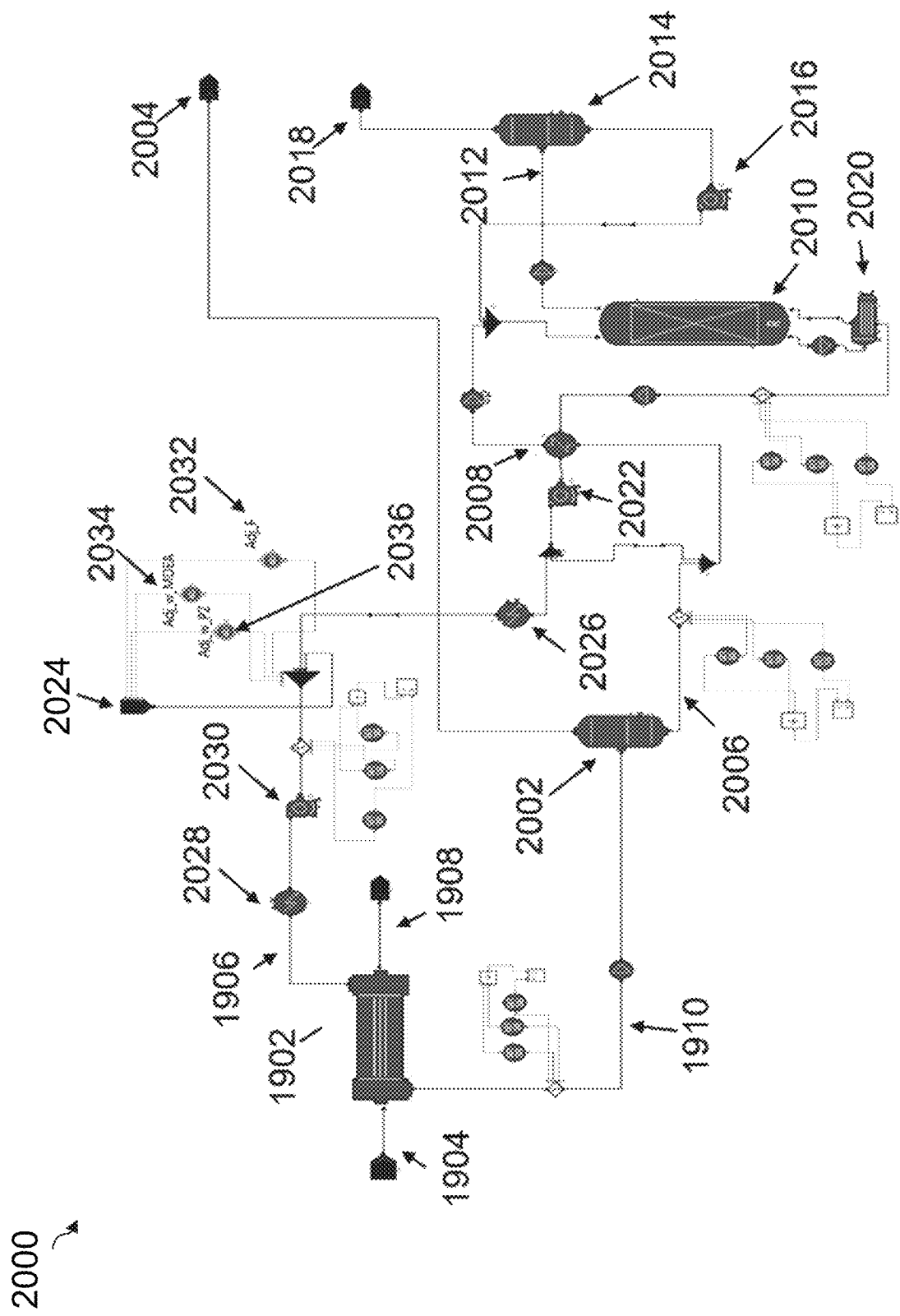
FIG. 20 shows a schematic of a MBC based natural gas sweetening process flowsheet in gPROMS ProcessBuilder in accordance with an embodiment.

FIG. 20 shows a schematic 2000 of a MBC based natural gas sweetening process flowsheet in gPROMS Process-Builder in accordance with an embodiment. The schematic 2000 shows a MBC process flowsheet which was built by integrating the above MBC unit operation model to a ProcessBuilder's standard unit operation library. As shown in the schematic/flowsheet 2000, besides the MBC unit operation model 1900 which comprises the MBC module 1902 having the gas inlet 1904, the liquid inlet 1906, the gas outlet 1908, and the liquid outlet 1910, the NG sweetening process flowsheet 2000 comprises a number of other components. As shown in FIG. 20, a rich solvent from the liquid outlet 1910 is in fluid communication with a rich solution flash drum 2002. A flash gas 2004 is discharged from the flash drum 2002 while a flash liquid outlet stream 2006 is outputted. The flash liquid outlet stream 2006 outputted is heated by a lean-rich exchanger 2008 with a hot lean solvent, and then fed to the solvent regenerator 2010 where it was stripped of acid gas 2012. The acid gas 2012 leaving the top of the regenerator was cooled and sent to a reflux drum 2014 with an overhead condenser (not shown) to separate the condensed water from the acid gas 2012. The condensed water was then returned to the top of the solvent regenerator 2010 via a reflux pump 2016, while the acid gas

2012 was sent to the flare header 2018. Finally, solvent make-up feeds from a reboiler 2020 is pumped back into the MBC module 1902 using a low pressure amine pump 2022, via a lean solution cooler 2026, a high pressure amine pump 2030 and an amine chiller 2028, to replenish the solvent evaporated in the MBC module 1902. The process flowsheet 2000 also provides a solvent makeup 2024 for adjusting a composition of the solvent flowing into the MBC module 1902.

An overview of the specifications in the regeneration unit operations (see Table 8 above) as well as some numerical solution details, in accordance with the present embodiment, are provided below. It should be appreciated that although specific models/packages were used, other suitable models/packages may be appropriate too.

Modelling of Rich Solution Flash Drum 2002

The rich amine from the MBC shell outlet passes through a pressure expander before entering the rich solution flash drum 2002. The outlet pressure of the expander is set to the rich solution flash drum pressure of 911 kPa (see Table 8). The rich solution drum itself is modelled as a two-phase (liquid-vapor) flash vessel, described by mass and energy balances, and thermodynamic equilibria using PSE, 2018 in *gPROMS ProcessBuilder Documentation* 1.3.1. Process Systems Enterprise Limited, United Kingdom (hereinafter "PSE, 2018"), which predicts the flowrates, compositions, temperatures, and pressures of the liquid and vapor outlet streams from the rich solution flash drum 2002. And the presence of multiple liquid phase is accounted for in the model.

Modelling of Heat Exchangers

Heat exchangers in the process model include the lean-rich heat exchanger 2008, the lean solution cooler 2026, the amine chiller 2028, the overhead condenser, and the reboiler 2020. The lean-rich heat exchanger 2008, which transfers heat from the regenerated amine (hot stream) to the rich amine (cold stream), is modeled as a counter current flow heat exchanger. The cold stream outlet temperature and pressures of both outlet streams are specified in Table 8. The lean solution cooler 2026 and the amine chiller 2028, which reduce the amine temperature to 318 K and 303 K, respectively (Table 8) after its regeneration, are modelled with a standard cooler. The overhead condenser and reflux drum 2014 are modeled as standard separators, with outlet temperature set to 333 K, in order for the fluid to separate into two phases. The reboiler is described by an evaporator kettle model, where the thermal specification is set at 403 K (Table 8). The heat exchanger models can be used to predict the process duty required to meet the thermal specifications.

Modeling of Pumps

Pumps in the process model include the amine HP pump 2030, amine LP pump 2022, and the reflux pump 2016. All these pumps are assumed to be mechanical with entropic efficiencies of 85%. The fluid outlet temperatures are further calculated by defining the fluid compression relative to an ideal compression process, using an ideal efficiency (PSE, 2018). The outlet pressures for the pumps are specified as per Table 8. The pump models predict the required process duty required based on the outlet pressure specifications and efficiencies.

Modeling of the Solvent Regenerator

For the solvent regenerator 2010, the rate-based model from gPROMS's Advanced Model Library (PSE, 2018) for Gas-Liquid Contactor (AML: GLC) is used in the present embodiment. The exchange of mass and heat between the bulk gas and liquid phases is described via gas and liquid films, separated by an infinitesimally thin interface where the phases are at equilibrium.

The Raschig Super Ring #1 packing characteristics (see e.g. Table 9) are used by the model. The built-in correlations in AML: GLC are used to calculate the performance of packing. Specifically, the Onda correlations for mass transfer with random packing are used to predict the mass transfer coefficients and the interfacial area, and the Billet holdup correlation is used to calculate the liquid holdup in the regenerator. It should be noted that the pressure drop in the column is neglected here in the present embodiment.

The solvent regenerator model is coupled with the reboiler 2020 and the overhead condenser as described above. The complete solvent regenerator model predicts the flow rate, composition temperature and pressure of the outlet gas and lean solvent streams.

Modeling of the Solvent Make-Up

The solvent make-up stream maintains the desired solvent flowrate and concentration in the MBC system. In gPROMS ProcessBuilder, three "Adjust" elements 2032, 2034, 2036 are used to set the solvent flowrate 2032 to MBC, MDEA mass fraction 2034 and PZ mass fraction 2036 to 275 L h$^{-1}$, 39 wt % and 5 wt %, respectively (Table 8). These three elements feed into a mixer immediately before the MBC unit.

Thermo-Physical, Transport, and Reaction Kinetic Data

Temperature-dependent expressions for the macroscopic reaction rates of $CO_2$ with MDEA and PZ, and the diffusivity coefficients of the various species in the gas and liquid mixtures used in the MBC model 1028 are described above, while Henry's constants for $CO_2$ in the amine solution was taken as described in relation to Equation 14. In order to reduce the computational burden, simple polynomial surrogates are derived in the temperature range of 300-400 K for the diffusivity coefficient $D_{CO_2,l}$, $D_{MDEA,l}$ and $D_{PZ,l}$ which are described below for completeness. These polynomial surrogates used advantageously speed up a simulation time while reducing computing resources used.

The diffusivity of $CO_2$ in liquid can be estimated based on the analogy of $N_2O$ diffusivity in solution as shown in Equation 20 below:

$$D_{CO_2,l} = D_{N_2O,l} \frac{D_{CO_2,H_2O}}{D_{N_2O,H_2O}} \quad (20)$$

The diffusivities of $CO_2$ and $N_2O$ in water are given by $$D_{CO_2,H_2O} = 2.35 \times 10^{-6} \exp\left(-\frac{2119}{T_l}\right) \quad (21)$$

$$D_{N_2O,H_2O} = 5.07 \times 10^{-6} \exp\left(-\frac{2371}{T_l}\right) \quad (22)$$

where $T_l$ is the temperature of the liquid.

The diffusion coefficient of $N_2O$ in liquid amine solution is estimated using the modified Stokes-Einstein relation as shown in Equation 23 below:

$$D_{N_2O,l} = D_{N_2O,H_2O} \left(\frac{\mu_{H_2O}}{\mu_l}\right)^{0.6} \quad (23)$$

where the viscosities $\mu_{H_2O}$ and $\mu_l$ of the water and amines, respectively, are obtained from the package 'UNIQUAC- RK' in the present embodiment. Likewise, the temperature-corrected diffusivities of MDEA and PZ amines in the liquid phase are correlated using the modified Stokes-Einstein relation.

$$D_{MDEA,I} = D_{MDEA,H_2O} \frac{T_I}{273} \left(\frac{\mu_{H_2O}}{\mu_I}\right)^{0.6} \quad (24)$$

$$D_{PZ,I} = D_{PZ,H_2O} \frac{T_I}{273} \left(\frac{\mu_{H_2O}}{\mu_I}\right)^{0.6} \quad (25)$$

where the diffusivities of MDEA and PZ in water, and the liquid and water dynamic viscosities are obtained from the package 'UNIQUAC-RK' in the present embodiment.

Other thermo-physical and transport parameters were obtained by interfacing gPROMS with the property packages Advanced Peng Robinson, UNIQUAC-RK and RSKA for the gas and liquid phases in the absorption and regeneration unit from Multiflash v6.1, respectively.

Numerical Simulation

A second-order centered finite difference scheme was used to discretize the partial differential equations of the MBC model 1028, after a rescaling of the radial dimension for the membrane dry and wet spatial subdomains to be rectangular as described in relation to FIG. 2. A coarser uniform mesh grid consisting of 35 elements was chosen to perform the simulations herein, which provides solutions within <1% of finer discretizations, while reducing the computational burden. For the solvent regenerator, a first-order finite difference method for the bulk liquid and vapor consisting of 20 elements was used.

Experimental Model Verification

Figure 21B:
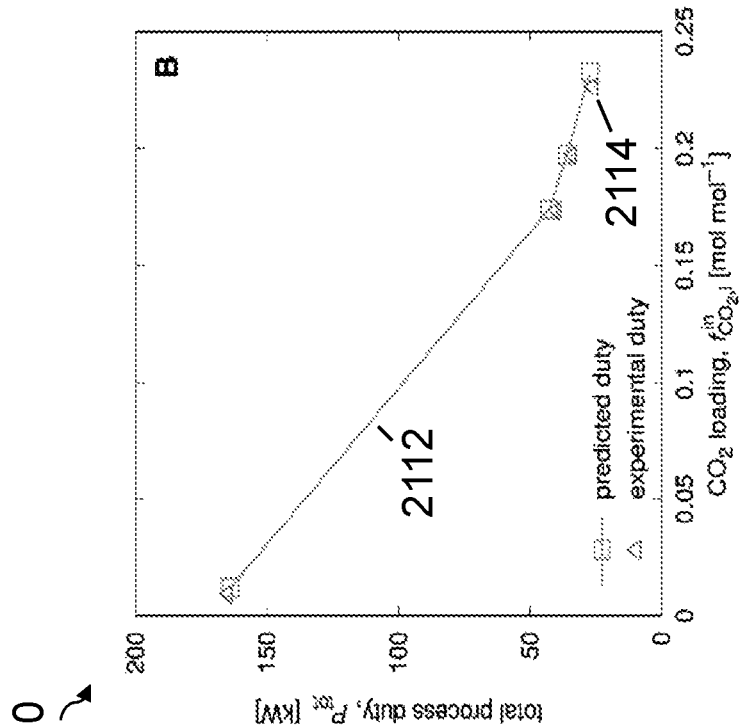
FIGS. 21A and 21B show graphs of predicted and experimental $CO_2$ purity at a MBC outlet, $CO_2$ removal efficiency and total process duty for different $CO_2$ loadings in an amine solvent in accordance with an embodiment, where
Figure 21A:
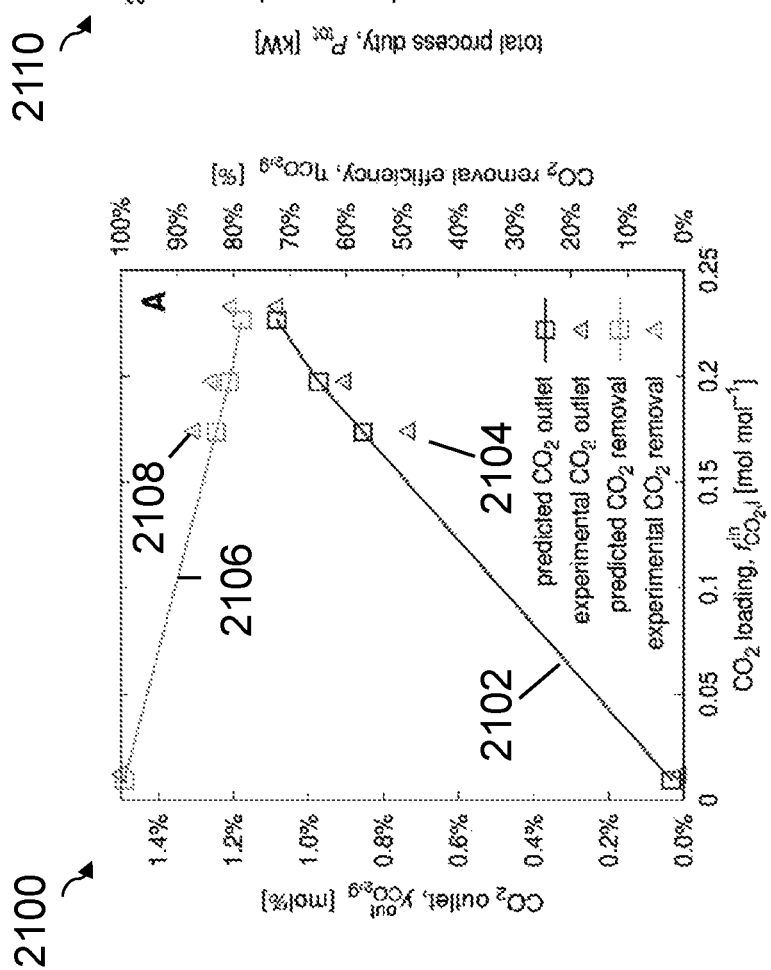

A comparison of the predicted $CO_2$ removal performance of the MBC, $CO_2$ loadings in amine and total process duty against measurements from the pilot plant are presented in FIGS. 21A and 21B in accordance with an embodiment. FIG. 21A shows a graph 2100 of predicted and experimental $CO_2$ purity and $CO_2$ removal efficiency for different $CO_2$ loadings in the amine solvent, while FIG. 21B shows a graph 2110 of predicted and experimental total process duty for different $CO_2$ loadings in the amine solvent. The experimental data are for different $CO_2$ loadings in the solvent, at constant gas and liquid flowrates of 75 kg h$^{-1}$ and 275 L h$^{-1}$, respectively.

As shown in FIG. 21A, predicted $CO_2$ outlet purity 2102, experimental data for $CO_2$ outlet purity 2104, predicted $CO_2$ removal efficiency 2106 and experimental data for $CO_2$ removal efficiency 2108 for different $CO_2$ loadings in the amine solvent are plotted. The predictions overall are found to be in good agreement with the measurements, showing errors lower than 5% for the $CO_2$ absorption fluxes and $CO_2$ removal efficiencies. Notice that an error of about 15% can be seen in the second experimental data point for $CO_2$ outlet purity in FIG. 21A when compared against the predicted $CO_2$ outlet purity. This may be because the low level of $CO_2$ outlet purity (0.73 mol %) is susceptible to large error which inevitably presents itself for even a small variation in the predicted $CO_2$ outlet purity (0.85 mol %). Nevertheless, when compared in terms of $CO_2$ absorption flux and removal efficiency, the predictions and measurement is found to be within 5%. Further, as shown in FIG. 21A, the MBC model 1028 correctly predicts that a larger $CO_2$ liquid loading reduces the $CO_2$ removal efficiencies, which in turn decreases the $CO_2$ outlet purity. As described above, an increase in the liquid $CO_2$ loading leads to a decrease in the $CO_2$ solubility and absorption capacity of solvent due to a reduction in free amine.

As shown in FIG. 21B, predicted total process duty 2112 and experimental total process duty 2114 are plotted. The process-wide model, comprised in the natural gas sweetening process operating system 1000 and as exemplified by the process flowsheet 2000, correctly predicts the reduction in heating and cooling duties with a higher $CO_2$ loading in the solvent. Similar to the results as shown in FIG. 21A, the overall predictions as shown in FIG. 21B are found to be in good agreement with the measurements, indicating errors lower than 5% for the $CO_2$ loadings and total process duty.

Figure 22B:
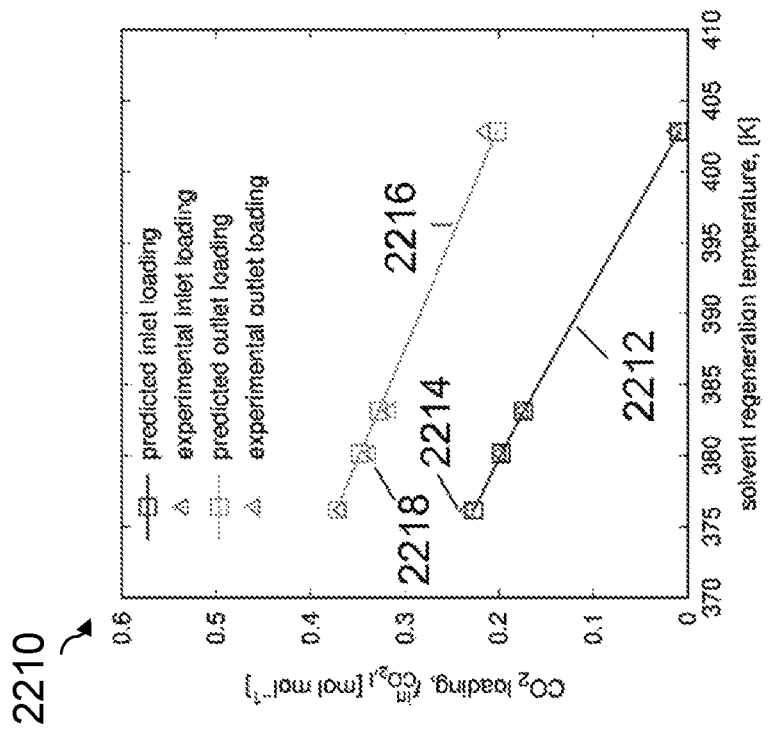
FIGS. 22A and 22B show graphs of predicted and experimental $CO_2$ absorption fluxes and $CO_2$ loadings for different solvent regeneration temperatures in accordance with an embodiment, where
Figure 22A:
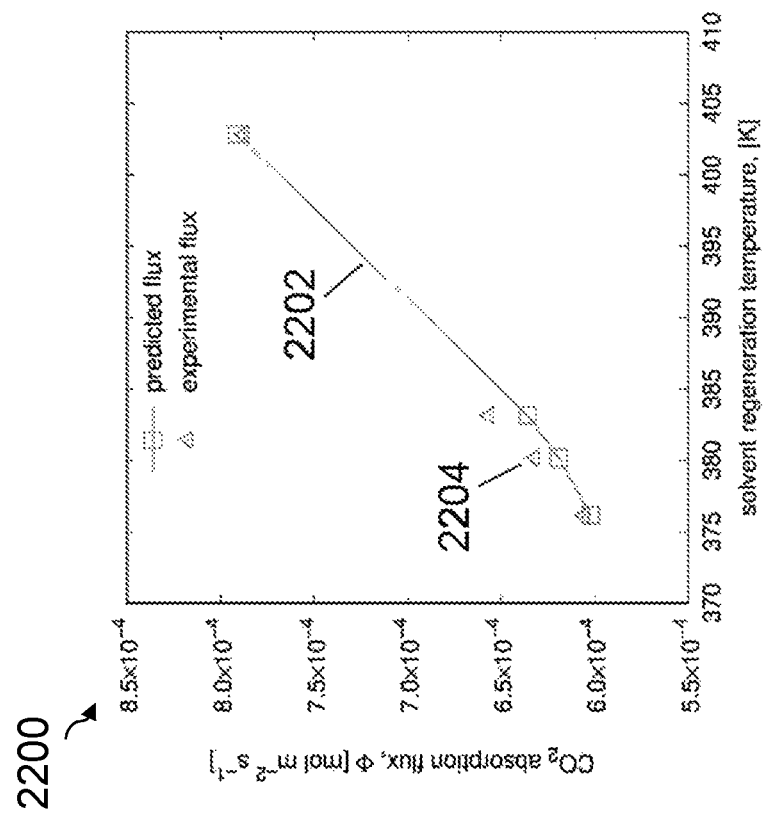

FIGS. 22A and 22B show graphs 2200, 2210 of predicted and experimental $CO_2$ absorption fluxes and $CO_2$ loadings for different solvent regeneration temperatures in accordance with an embodiment. Referring to FIG. 22A, predicted $CO_2$ absorption flux 2202 and experimental $CO_2$ absorption flux 2204 for different solvent regeneration temperatures are shown. FIG. 22B shows data points for predicted inlet $CO_2$ loadings 2212, experimental inlet $CO_2$ loadings 2214, predicted outlet $CO_2$ loadings 2216 and experimental outlet $CO_2$ loadings 2218 for different solvent regeneration temperatures.

The reboiler 2020 for the solvent regenerator 2010 can be operated at a lower temperature under semi-lean operation (see e.g. FIG. 22B), which reduces the energy needed for solvent regeneration. For example, it was previously shown that the reboiler duty can be significantly reduced by increasing the solvent $CO_2$ loading up to 0.23 and 0.27 mol mol$^{-1}$, respectively. Notice that the increase in regeneration temperature decreases the $CO_2$ inlet loading (see e.g. FIG. 22B) to the MBC 1902, which in turn improves the $CO_2$ absorption flux (see e.g. FIG. 22A). Also, notice that the difference between the inlet and outlet $CO_2$ loading is larger for a lean amine operation ($f_{CO_2,I}^{in}$=0.01) compared to a semi-lean operation ($f_{CO_2,I}^{in}$=0.23) as shown in FIG. 22B. This is because the $CO_2$ removal efficiency (ca. 99.9%) for the lean amine operation is higher compared to the semi-lean operation (ca. 80%) as depicted in FIG. 21A.

In order to achieve deep $CO_2$ removal, for example to meet the LNG specification of less than 50 ppmv of $CO_2$, the process-wide model indicates that a lean solvent is necessary (e.g. with a $CO_2$ loading≈0.01 mol mol$^{-1}$). On the other hand, a semi-lean solvent (e.g. with a $CO_2$ loading ca. 0.23 mol mol$^{-1}$) operation appears to be sufficient to meet the typical sales gas specification of <1.5 mol % $CO_2$. In this particular experiment, the semi-lean operation consumes ca. 80% less energy compared to lean operation. Further model-based analysis and design of NG sweetening using an MBC process are described below.

Model-Based Analysis of Pilot-Scale MBC

The process-wide model as described above was developed for the MBC pilot plant to facilitate analysis of: (i) the process duty for an optimised MBC lean and semi-lean amine process; (ii) the optimum pressure at the rich solution flash drum for maximum fuel gas recovery; and (iii) the amount and concentration of solvent make-up.

Optimal Solvent Flowrate for Lean and Semi-Lean Operations

As described above in relation to FIGS. 21A, 21B, 22A and 22B, the experimental verification of the process-wide model has shown that both lean and semi-lean operations are capable of $CO_2$ purities down to the sales gas specification of <1.5 mol %, with the semi-lean operation consuming 80% less energy compared to lean operation. However, these experiments were all conducted with same flowrate of the solvent to the MBC 1902 and may therefore correspond to a suboptimal operation. Herein, the minimum liquid flowrate required is determined to achieve a $CO_2$ purity of 1.5 mol % for processing 75 kg h$^{-1}$ of sour natural gas. The lean amine operation conducted is similar to the flowsheet as shown in FIG. 20 but without the excess amine recycle back to the solvent regenerator 2010. The dimension of the solvent regenerator 2010 is designed to remain the same in the pilot plant in order to provide a conservative reboiler process duty when compared with the semi-lean process.

Figure 23:
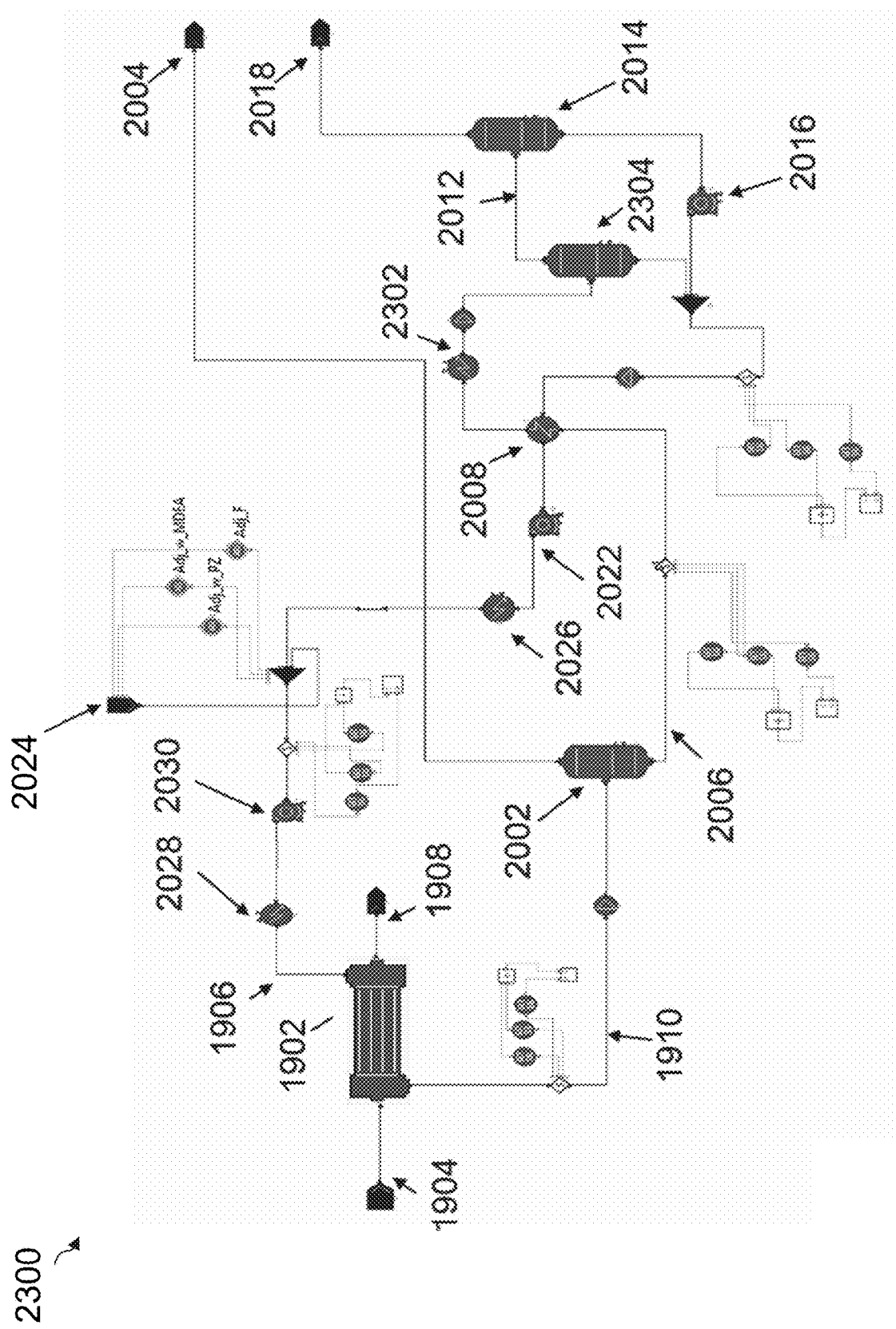
FIG. 23 shows a schematic of a MBC pilot scale semi-lean operation process flowsheet in gPROMS ProcessBuilder in accordance with an embodiment.

FIG. 23 shows a schematic 2300 of a MBC pilot scale semi-lean operation process flowsheet in gPROMS Process-Builder in accordance with an embodiment. The semi-lean operation process flowsheet as shown in FIG. 23 is similar to that of FIG. 20, except that the reboiler 2020 and solvent regenerator 2010 are replaced with a heater 2302 and a low-pressure flash drum 2304. All of the pressure and temperature specifications for the flowsheets of both the lean operation and the semi-lean operation remain the same as described above in relation to Tables 8 to 10, except for the reboiler/heater temperature which is adjusted to obtain the desired $CO_2$ loading in the solvent. The results of this comparison are reported in Table 11 below.

As shown in Table 11, the optimised lean operation requires a 34% lower solvent flowrate to the MBC compared to the optimised semi-lean operation to meet the required $CO_2$ purity. This is due to a higher $CO_2$ absorption capacity of the lean solvent, which enhances the $CO_2$ removal rate in the MBC 1902. With a lower solvent flowrate, the process-wide model predicts a decrease in the process duties of all the pumps in comparison to the semi-lean operation. This corresponds to a L/G ratio of ca. 0.75 m$^3$ kmol$^{-1}$, which is at the lower end values of 0.6-1.1 m$^3$ kmol$^{-1}$ typically encountered in a conventional packed column.

TABLE 11

Optimised operating conditions and process duty of the lean and semi-lean MBC

| Parameters | Lean Operation | Semi Lean Operation |
|---|---|---|
| MBC (Absorption) | | |
| $CO_2$ inlet, $y_{CO_2, g}^{in}$ [mol %] | 5 | 5 |
| MDEA/PZ inlet, [wt %] | 39/5 | 39/5 |
| Inlet gas pressure, $P_g^{in}$ [kPa] | 5400 | 5400 |
| Outlet liquid pressure, $P_l^{out}$ [kPa] | 5430 | 5430 |
| Gas mass flowrate, $M_g^{in}$ [kg h$^{-1}$] | 75 | 75 |
| Liquid volumetric flowrate, $F_l^{in}$ [L h$^{-1}$] | 109 | 146 |
| Gas temperature, $T_g^{in}$ [K] | 297 | 297 |
| Liquid temperature, $T_l^{in}$ [K] | 303 | 303 |
| $CO_2$ loading in the solvent, $f_{CO_2, l}^{in}$ [mol mol$^{-1}$] | 0.01 | 0.24 |
| Solvent Regeneration (Desorption) | | |
| Reboiler/Heater temperature, [K] | 403 | 376 |
| Reboiler duty, [kW] | 6.92 | 4.41 |
| Overhead condenser duty, [kW] | 0.51 | 1.41 |
| Reflux Pump duty, [kW] | 5.10E−5 | 1.45E−4 |
| Lean solution pump duty, [kW] | 0.0173 | 0.022 |
| HP amine pump duty, [kW] | 0.181 | 0.24 |
| Lean solution cooler duty, [kW] | 4.8 | 2.87 |
| Amine chiller duty, [kW] | 1.35 | 1.8 |
| Total process duty, [kW] | 13.7 | 10.7 |

However, the total process duty remains 28% higher under lean operation compared to semi-lean operation, due to the higher reboiler temperature that is required to regenerate the solvent under lean operation. This leads to a higher temperature of the regenerated solvent which also requires a higher cooling duty in the lean solution cooler before returning the solvent to the MBC, despite the heat integration between the inlet and outlet streams to the regenerator.

FIGS. 24A and 24B show pie charts 2400, 2420 of a breakdown of the equipment process duty in accordance with an embodiment, where FIG. 24A shows a pie chart 2400 of a breakdown of the equipment process duty for lean amine operation in the MBC and FIG. 24B shows a pie chart 2420 of a breakdown of the equipment process duty for semi-lean amine operation in the MBC 1902. The breakdown of total process duty in terms of the different pieces of equipment are shown for each of FIGS. 24A and 24B.

As shown in FIG. 24A, under lean operation, the reboiler contributes 50.2% (denoted by 2402) of the equipment process duty, the overhead condenser contributes 3.7% (denoted by 2404) of the equipment process duty, the pumps contributes 1.4% (denoted by 2406) of the equipment process duty, the lean solution cooler contributes 34.8% (denoted by 2408) of the equipment process duty and the amine chiller contributes 9.8% (denoted by 2410) of the equipment process duty. On the other hand, as shown in FIG. 24B, under semi-lean operation, the reboiler contributes 41.0% (denoted by 2422) of the equipment process duty, the overhead condenser contributes 13.1% (denoted by 2424) of the equipment process duty, the pumps contributes 2.4% (denoted by 2426) of the equipment process duty, the lean solution cooler contributes 26.7% (denoted by 2428) of the equipment process duty and the amine chiller contributes 16.7% (denoted by 2430) of the equipment process duty.

As shown in both FIGS. 24A and 24B, the reboiler duty is the largest energy consumer with approximately 40-50% of the overall process duty for both operations, which is consistent with the findings of previous works. The lean solution cooler and amine chiller come in second and third, respectively, with 26-35% and 9-17% of the total process duty. Based on this analysis, one area of improvement could be to operate the liquid above 318 K at the MBC absorption section. This operation would eliminate the requirement of an amine chiller, therefore potentially reducing the footprint and process duty by a further 9-17% in both operations.

Overall, the semi-lean operation presents a higher intensification potential with the reduction in energy consumption and footprint (i.e., flash tank and heater), and this should translate into a reduction in capital and operating expenditure compared to the lean operation.

Optimal Flash Pressure for Fuel Gas Recovery

Any hydrocarbons (HC) absorbed in the solvent that is not recovered will end up in the acid gas stream. This could represent a large product loss and may cause problems elsewhere in the process. To maximize flash gas recovery for minimising a product loss, an optimum pressure at which to operate the rich solution flash drum 2002 is investigated. A key constraint in practice is that the recovered flash gas should have a high enough lower heating value (LHV) in order to meet a conventional fuel gas specification for example of 47.1 MJ kg$^{-1}$. From a thermodynamic standpoint, operating the rich solution flash drum 2002 at a lower pressure will increase the amount of flash gas, hence increasing fuel gas recovery. However, those species with a lower vapor pressure, such as $CO_2$, will also flash off, and thus reduce the fuel gas LHV. This, therefore, defines an optimal trade-off in terms of the flash drum pressure.

The total HC recovery from solvent at the rich solution flash drum 2002, denoted by $f_{HC,g}^{out}$ [mol mol$^{-1}$], and the LHV of the recovered flash HC gas, LHV$_g$ [MJ kg$^{-1}$] is computed as $$f_{HC,g}^{out} = \frac{\sum N_{i,g}^{fd}}{\sum N_{i,I}^{out}} \quad (26)$$

$$LHV_g = \sum y_{i,g}^{fd} LHV_i \quad (27)$$

where $N_{i,g}^{fd}$ [kmol h$^{-1}$] and $y_{i,g}^{fd}$ [−] are the molar flowrates and the mass fraction i∈{CH$_4$, C$_2$H$_6$, C$_3$H$_8$} in the flash gas from the rich solution drum; and the individual LHV values, LHV$_i$ [MJ kg$^{-1}$] are based on ISO 6976 (see e.g. ISO, 2016—*Natural gas—Calculation of calorific values, density, relative density and Wobbe index from composition*).

Figures 25A, 25B:
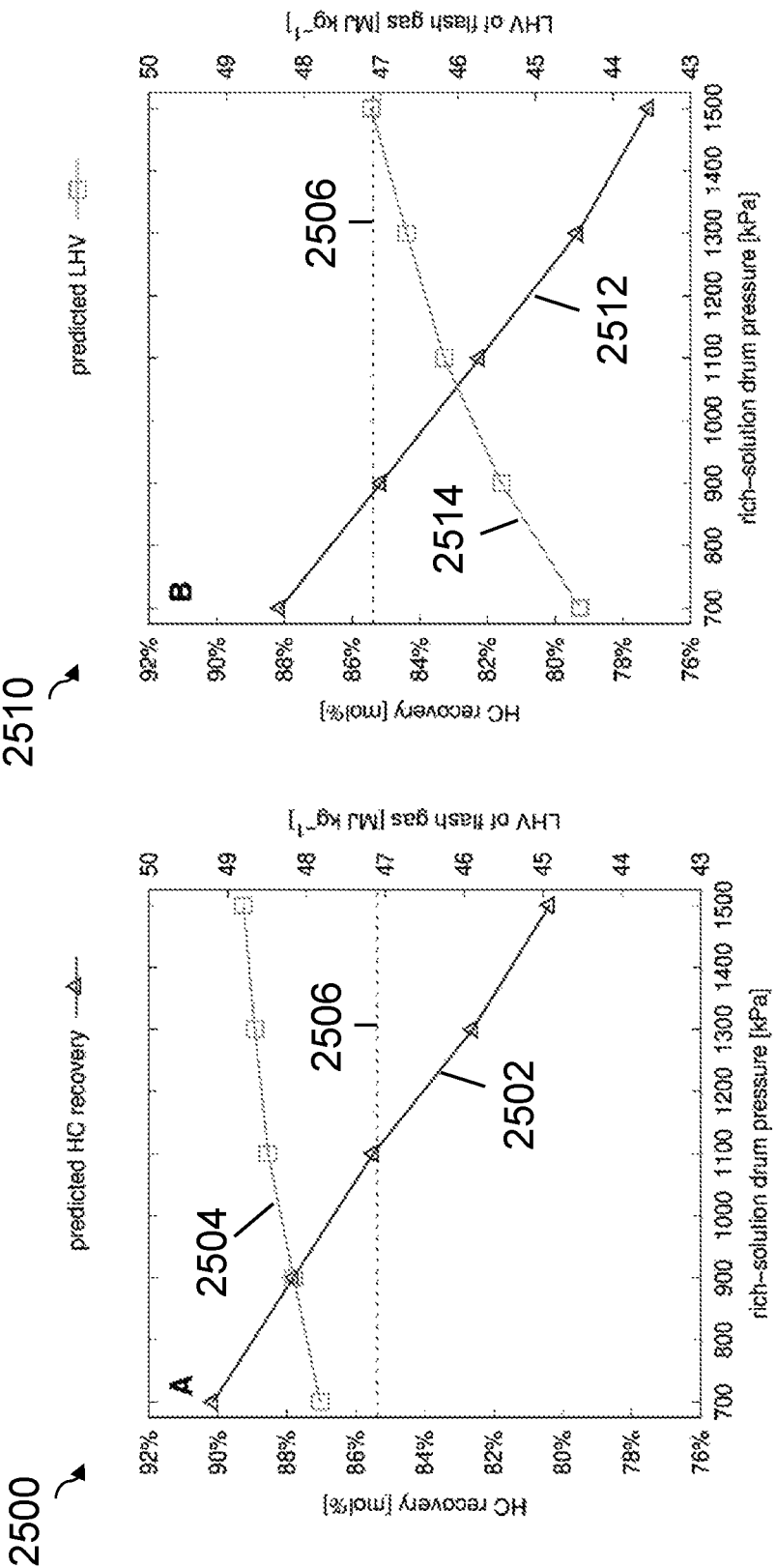
FIGS. 25A and 25B show graphs of predicted hydrocarbon recovery and Lower Heating Value (LHV) of the natural gas against rich-solution drum pressure in accordance with an embodiment, where

FIGS. 25A and 25B show graphs 2500, 2510 of predicted hydrocarbon recovery and Lower Heating Value (LHV) of the natural gas against rich-solution drum pressure in accordance with an embodiment. FIG. 25A shows a graph 2500 of predicted hydrocarbon recovery 2502 and Lower Heating Value (LHV) of the natural gas 2504 against rich-solution drum pressure under lean amine operation (where $f_{CO_2,I}^{in}$=0.01). The dotted line 2506 as shown in FIGS. 25A and 25B defines the conventional fuel gas specification of 47.1 MJ kg$^{-1}$ described above. FIG. 25B shows a graph 2510 of predicted hydrocarbon recovery 2512 and Lower Heating Value (LHV) of the natural gas 2514 against rich-solution drum pressure under semi-lean amine operation (where $f_{CO_2,I}^{in}$=0.23). The NG gas and solvent flowrates used are 75 kg h$^{-1}$ and 275 L h$^{-1}$ respectively for both graphs 2500, 2510.

As shown in FIGS. 25A and 25B, the process-wide model predicts an improvement in HC recovery, from about 81% to 90% and 77% to 88%, by decreasing the rich solution flash drum pressure from 1500 kPa to 700 kPa for the lean and semi-lean operation, respectively. Note that for the lean amine operation as shown in FIG. 25A, the flash gas meets the fuel gas LHV at all operating pressures and a maximum of 90% HC recovery can be obtained at 700 kPa. On the other hand, the predicted LHV for all the operating pressures of interest under semi-lean operation as shown in FIG. 25B fail to meet the fuel gas specification except at 1500 kPa, with a lower HC recovery of 77%. The high CO$_2$ content in the flash gas is attributed to the higher CO$_2$ loading in the rich amine ($f_{CO_2,I}^{out}$=0.37 mol mol$^{-1}$) from the MBC module 1902 under the semi-lean operation as compared to the CO$_2$ loading of $f_{CO_2,I}^{out}$=0.20 mol mol$^{-1}$ in the lean amine operation (e.g. with reference to FIG. 22B). In order to recover more flash gas, further sweetening of the flash gas containing CO$_2$ would be required in order to use it as a fuel gas. Otherwise, this flash gas could be compressed and returned to the MBC gas inlet or the treated gas, subject to meeting the required CO$_2$ purity.

MBC Process-Wide Assessment of Solvent Losses

The amine solvent is not consumed during the acid gas removal process, but some amine loss is inevitable due to evaporation or entrainment. Unlike conventional packed columns, solvent entrainment is prevented in the MBC 1902 by the microporous membrane which allows the liquid and gas phases to be in contact with each other, yet without the dispersion of one phase in the other. On the other hand, solvent evaporative losses in the form of either water, MDEA or PZ can occur with the treated gas, flash gas and acid gas streams. They are dependent on the type and concentration of amine, as well as on the temperature and pressure of the MBC 1902, the flash drum 2002 and the solvent regenerator 2010. The solvent makeup stream (denoted for example by 2024 in the flowsheet 2000 of FIG. 20) aims to compensate for these losses and to maintain the desired solvent concentration in the process.

It is conventionally known that existing gas processing plants using monoethanolamine (MEA), diethanolamine (DEA), and MDEA report an average amine loss rate of 2×10$^{-4}$ kg Nm$^{-3}$ in treated gas. There is a potential for reducing these losses to below 7×10$^{-5}$ kg Nm$^{-3}$ of treated gas in most gas processing systems.

Figure 26A:
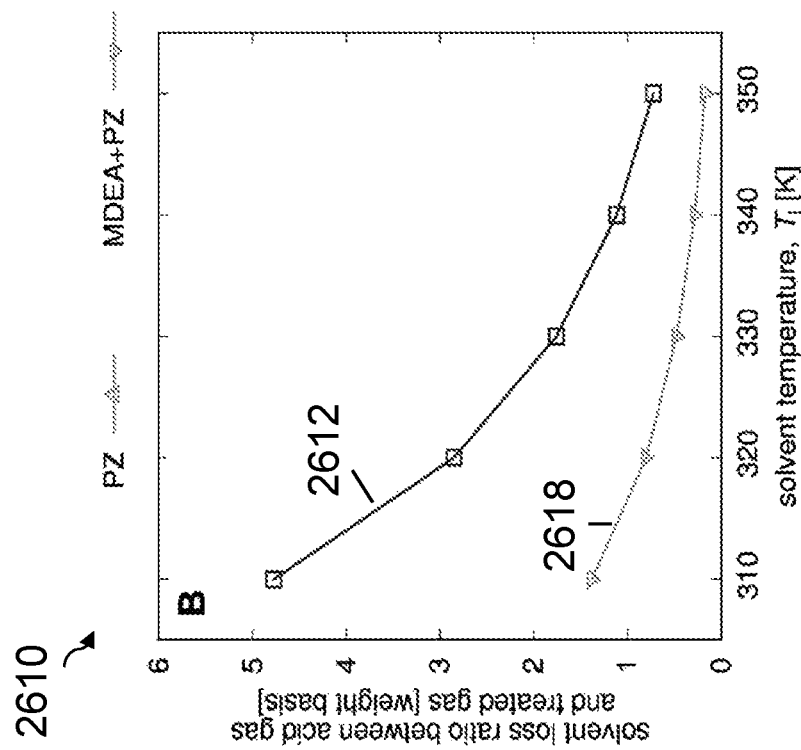
FIGS. 26A and 26B show graphs illustrating an effect of solvent temperature at the MBC inlet on evaporative losses of different components (i.e. water, MDEA and PZ) of the solvent in a natural gas sweetening process in accordance with an embodiment, where
Figure 26B:
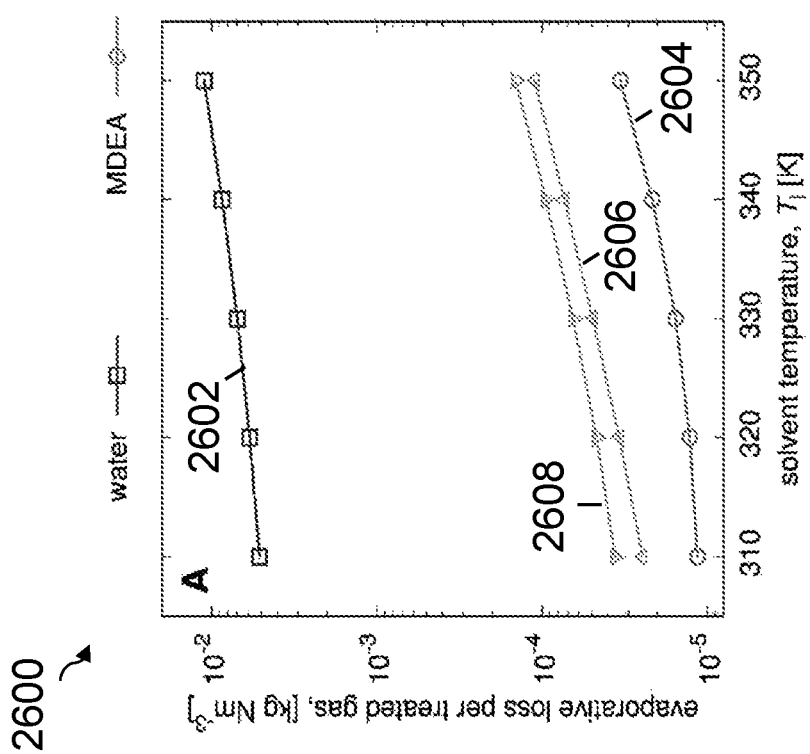

FIGS. 26A and 26B show graphs 2600, 2610 illustrating an effect of solvent temperature at the MBC inlet on evaporative losses of different components (i.e. water, MDEA and PZ) of the solvent in the process in accordance with the present embodiment. FIG. 26A shows a graph 2600 of evaporative loss of water 2602, MDEA 2604, PZ 2606 and MDEA+PZ 2608 at different solvent temperatures. FIG. 26B shows a graph 2610 of the ratio of evaporative loss in acid gas to loss in treated gas for water 2602 and MDEA+PZ 2608 at different solvent temperatures. The NG gas and solvent flowrates of 75 kg h$^{-1}$ and 275 L h$^{-1}$ respectively are used in simulating the graphs 2600, 2610.

As shown in FIGS. 26A, as the liquid temperature rises, the rates of water 2602, MDEA 2604 and PZ 2606 evaporation increase due to the corresponding rise of their vapor pressures. FIG. 26A also shows that the water evaporative loss rate 2602 is the highest followed by PZ 2606 and MDEA 2604, which is consistent with the components respective vapor pressures (see e.g. FIG. 18). In addition, the amine loss rate is between 0.3-1.1×10$^{-4}$ kg Nm$^{-3}$. Overall, the amine loss is approximately 0.15% of the solvent's circulation rate (0.4 L h$^{-1}$ of 275 L h$^{-1}$), and water makes over 99 wt % of these losses. This suggests that pure water make-up should be sufficient during normal operations to maintain the solvent concentration. When the amine concentration degrades or the solvent inventory in the process drops, a small portion of the amine solvent can be replaced by the fresh amine into the process.

FIG. 26B presents the effect of solvent temperature into MBC on the ratio of evaporative loss in acid gas to loss in treated gas (mass basis) for water 2612 and MDEA+PZ 2618. These results show that significant evaporative losses occur with the solvent regenerator overhead as well, which are of the same order of magnitude as the evaporative losses with the MBC treated gas. Although small, the amine losses that occur within the MBC and regeneration section should not be neglected. This is shown as described in the following section.

Model-Based Scale-Up of a Commercial MBC for Natural Gas Sweetening

The objective of this section is to design a commercial MBC module (membrane area, solvent flowrate) for a semi-lean MBC operation in an industrially relevant NG sweetening application by using the knowledge acquired from the lab-scale and pilot scale studies as described above. The inlet NG has a CO$_2$ content of 24 mol % which is to be reduced to <6.5 mol % (as shown in Table 12 below) and with a flowrate of 11,630 kmol h$^{-1}$. Note that in this simulation study, the amine chiller 2028 was removed, and the overhead condenser operates at 318 K in order to minimise amine loss to the acid gas. A model-based scale-up and analysis is conducted to assess this MBC in terms of (i) reboiler energy required per ton CO$_2$ removed; (ii) potential savings from the HC recovery in the rich solution flash drum; and (iii) the amount of MDEA and PZ make-up required to maintain solvent concentration.

TABLE 12

Operating conditions in an industrially relevant NG sweetening application

| Parameters | Natural Gas |
|---|---|
| MBC (Absorption) | |
| $CO_2$ inlet/target outlet, $y_{CO_2, g}^{in}/y_{CO_2, g}^{out}$ [mol %] | 24/<6.5 |
| $CH_4$, $C_2H_6$, $C_3H_8$ [mol %] | 73/2/1 |
| MDEA/PZ inlet [wt %] | 39/5 |
| Inlet gas pressure, $P_g^{in}$ [kPa] | 5400 |
| Outlet liquid pressure, $P_l^{out}$ [kPa] | 5430 |
| Gas flowrate, $N_g^{in}$ [kmol h$^{-1}$] | 11,630 |
| Liquid volumetric flowrate, $F_l^{in}$ [m$^3$ h$^{-1}$] | 1750 |
| Gas temperature, $T_g^{in}$ [K] | 312 |
| Liquid temperature, $T_l^{in}$ [K] | 318 |
| $CO_2$ loading in solvent, $f_{CO_2, l}^{in}$ [mol mol$^{-1}$] | 0.22 |
| Solvent Regeneration (Desorption) | |
| Rich solution drum pressure [kPa] | 911 |
| Low pressure flash drum [kPa] | 258 |
| Heater temperature [K] | 377 |
| Overhead condenser-Outlet [K] | 318 |
| Reflux pump pressure-Outlet, [kPa] | 258 |
| Lean-rich exchanger | |
| Cold stream-Inlet/Outlet [K]/[kPa] | 343/364/368 |
| Hot stream-Inlet/Outlet [K]/[kPa] | 374/344/233 |
| LP amine pump pressure-Outlet [kPa] | 711 |
| Lean solution cooler-Outlet [K] | 318 |
| Pressure drop [kPa] | 35 |
| Amine HP pump pressure-Outlet [kPa] | 5460 |

The characteristics of the membrane are identical to the one used in Table 2, with the module cartridge inner radius, $R_m$ at 0.115 m, following the pilot-scale module. Table 13 below reports the geometrical properties of the MBC used for the scale-up of an industrially relevant NG sweetening application.

TABLE 13

Specifications of the commercial-scale MBC

| Parameters | Commercial MBC module | Source |
|---|---|---|
| Module cartridge inner radius, $R_m$ [m] | 0.115 | (PRSB, 2017) |
| Number of fibres per module cartridge, N [—] | 17,024 | (PRSB, 2017) |
| MBC module inner radius, $R_c$ [m] | 0.8 | (PRSB, 2017) |
| Number of cartridges per MBC module, $N_o$ [—] | 31 | (PRSB, 2017) |
| Membrane area, $A_m$ [m$^2$] | 288,687 | Equation 30 |
| Total number of module cartridges, $N_c$ [—] | 2115 | Equation 31 |
| Number of MBC modules, $N_{MBC}$ [—] | 69 | Equation 32 |

Note:
PRSB (2017)-'Conceptual Design of Commercial MBC Module', PETRONAS Research Sdn Bhd.

Approximations of the solvent flowrate, $F_l^{in}$ and membrane area, $A_m$ are first derived from the L/G ratio and $CO_2$ absorption flux $$\Phi = \frac{\eta_{CO_2,g}}{A_m}$$

obtained from the lab-scale experiment in relation to FIG. 16, which was operated under similar operating condition outlined in Table 13 above. Here, $\eta_{CO_2,g}$ refers to a molar gas flowrate of the $CO_2$ absorbed. The experimental L/G ratio, defined as the solvent flowrate per mol of $CO_2$ removed, and the $CO_2$ absorption flux were L/G=0.86 m$^3$ kmol$^{-1}$ and $\Phi$=7.02×10$^{-3}$ kmol m$^{-2}$ hr$^{-1}$, respectively. Herein, the required solvent flowrate can thus be estimated as:

$$\eta_{CO_2,g} = (y_{CO_2,g}^{in} - y_{CO_2,g}^{out})N_g^{in} \quad (28)$$

$$F_l^{in} = \eta_{CO_2,g} \times L/G \quad (29)$$

The membrane area, $A_m$ and number of module cartridges, $N_c$ are determined as follows:

$$A_m = \frac{\eta_{CO_2,g}}{\Phi}, \quad (30)$$

$$N_c = \frac{A_m}{2\pi r_2 LN}, \quad (31)$$

where $N_c$ is rounded to the next integer.

The total number of module cartridges, $N_c$ is expected to be large and therefore a commercial scale module with a radius of 0.8 m, containing 31 MBC cartridges of radius 0.115 m each is considered. This is shown in FIG. 27 where a schematic 2700 of a cross-section of a commercial MBC module 2702 is illustrated in accordance with an embodiment. As shown in FIG. 27, the MBC module 2702 includes 31 MBC cartridges 2704. This design is preferred as it reduces the number of high-pressure vessels, therefore limiting reducing the physical footprint and weight of the module.

Then, the number of MBC modules, $N_{MBC}$ is determined as follow:

$$N_{MBC} = \frac{N_c}{N_o} \quad (32)$$

where $N_o$ is the number of cartridges per MBC module; and $N_{MBC}$ is rounded to the next integer.

A model-based scale-up of the MBC plant is then conducted based on the operating conditions and MBC characteristics in Tables 12 and 13 respectively. Predicted values of the process KPIs are tabulated in Table 14.

TABLE 14

Model predictions of the process KPIs.

| Parameters | Predicted values |
|---|---|
| $CO_2$ purity of treated gas, $y_{CO_2, g}^{out}$ [mol %] | 6.1 |
| $CO_2$ absorption flux, $\Phi$ [kmol m$^{-2}$ hr$^{-1}$] | 7.71 × 10$^{-3}$ |
| L/G ratio [m$^3$ kmol$^{-1}$] | 0.78 |
| Reboiler energy per ton of $CO_2$ removed [GJ ton$^{-1}$] | 2.2 |
| Amount of flash gas recovered, $M_g^{fd}$ [kg h$^{-1}$] | 1692-1908 |
| HC recovery in the flash gas, $f_{HC, g}^{out}$ [%] | 82 |
| Annual savings from HC recovery [US$ million yr$^{-1}$] | 0.96-1.10 |
| Predicted flash gas lower heating value, $LHV_g$ [MJ kg$^{-1}$] | 30.2 |
| Amine loss rate per treated gas [kg Nm$^{-3}$] | 1.24 × 10$^{-4}$ |
| Amine loss rate per ton of $CO_2$ removed [kg ton$^{-1}$] | 0.28 |
| MDEA make-up required [ton yr$^{-1}$] | 73 |
| PZ make-up required, $F_l^{in}$ [ton yr$^{-1}$] | 144 |

The process-wide model predicted that the $CO_2$ purity at the treated gas meets the targeted specification of <6.5 mol % with approximately 10% improvement in the $CO_2$ absorption flux and UG ratio compared to the lab-scale experiment in FIG. 16. This is attributed to operating the solvent inlet temperature at a higher temperature of 318 K, in order to eliminate the requirement of the amine chiller 2028 as previously described. It is also found that an increase in the solvent temperature improves the $CO_2$ absorption flux, despite a slight increase in the average membrane wetting, whereby the increase in mass transfer due to higher reaction rates and diffusivities of $CO_2$ and amines dominates over the decreased in $CO_2$ solubility in the amine solvent.

The predicted reboiler energy per ton of $CO_2$ removed is 2.2 GJ ton$^{-1}$, which is lower compared to the range of 2.4-4.2 GJ ton$^{-1}$, typically reported for amine-based absorption process. This can be attributed to the semi-lean operation of the MBC system, which was shown to reduce the energy consumption as discussed in relation to FIGS. 24A and 24B. In addition, the process-wide model predicted the amine loss rate per treated gas is $1.35 \times 10^{-4}$ kg Nm$^{-3}$, which is below the average amine loss rates of $2 \times 10^{-4}$ kg Nm$^{-3}$ in a recent survey. Similarly, the predicted amine loss per ton of $CO_2$ removed of 0.28 kg ton$^{-1}$, is at the lower end of the range 0.35-2.0 kg ton$^{-1}$ that is typically reported for amine-based processes. The resulting solvent make-up, are 73 and 144 ton yr$^{-1}$ for MDEA and PZ, respectively.

Finally, a sensitivity analysis of ±5% on the Henry's constants of HC in the solvent was simulated to determine how uncertainty in the Henry's constant propagates into the estimation of the amount of flash gas recovered at the rich solution flash drum and its heating value, which are used to quantify the annual savings from HC recovery. The predicted amount of flash gas recovered is 1692-1908 kg hr$^{-1}$, corresponding to a range of +5% and −5% of the Henry's constant of HC in the solvent, respectively. On the other hand, the predicted heating value of the flash gas $LHV_g$ and HC recovery is 30 MJ kg$^{-1}$ and 82%, respectively. Similar to the findings for semi-lean operation as discussed in relation to FIG. 25B, the predicted $LHV_g$ is lower than the fuel gas specification of 47.1 MJ kg$^{-1}$, which is due to the higher $CO_2$ content of the flash gas. A sensitivity analysis of the operating pressure of the flash drum up to 1500 kPa only shows improvement of the $LHV_g$ to 37 MJ kg$^{-1}$, yet with a lower HC recovery of 68%. The high $CO_2$ content in the flash gas is attributed to the higher $CO_2$ loading in the rich amine ($f_{CO_2,l}^{out}=0.56$ mol mol$^{-1}$) from the MBC compared to the $CO_2$ loading of $f_{CO_2,l}^{out}=0.38$ mol mol$^{-1}$ in the pilot-scale experiment as previously described. Therefore, the flash gas containing $CO_2$ will require sweetening at the top section of the flash drum in order to be used as fuel gas. Otherwise, this flash gas could be compressed and returned to the MBC gas inlet. Using the MBC model, the annual cost savings from the flash gas recovery can be quantified, which is closed to a million US dollars.

Overall, the intensification potential of the scaled-up MBC commercial module showed promising prospects, whereby (i) the predicted reboiler energy per ton of $CO_2$ removed is lower than the conventional amine absorption column by 12-50%; (ii) the predicted amine loss rate per treated gas and per ton of $CO_2$ removed are lower compared to the typical loss rates reported in a conventional amine-based processes; and (iii) a potential savings of about US$1 million yr$^{-1}$ from the HC recovery can be realized, subject to further sweetening of the flash gas. Nevertheless, a total number of MBC modules required in accordance with the present embodiment is 69 and this will require a footprint area of ca. 250 m$^2$. This implies that use of a MBC may require a larger footprint as compared to a conventional absorption column. In embodiments, further improvement on the membrane characteristics such as to increase the specific surface area and the hydrophobicity of the membrane are required to improve the intensification potential in terms of footprint. In some embodiments, commercial MBC modules may also be designed to be stacked for minimising the footprint.

As described above, the experimental data and model analysis has confirmed the advantages of semi-lean operation in terms of energy reduction and physical footprint. The results suggest that semi-lean operation is sufficient for bulk $CO_2$ removal to meet sales gas specification, while lean amine operation is required for deep $CO_2$ removal in order to meet LNG specification. The optimum operating pressure for the rich solution flash drum could also be determined, in order to maximise HC recovery from the solvent, while meeting the fuel gas LHV specification. In addition, the evaporation rate of the solvent has been predicted to be predominantly water, and therefore, pure water make-up should be sufficient to maintain the amine concentration in the solvent during normal operation. Further, the predicted amine loss rate has been found to be within the typically reported loss rates for conventional $CO_2$ absorption process.

The scale-up of a commercial MBC has been conducted for a semi-lean MBC operating in an industrially relevant NG sweetening application in order to meet a $CO_2$ purity of <6.5 mol %. The method to predict the required solvent flowrate and membrane area for the commercial-scale MBC has used knowledge of the experimental L/G ratio and $CO_2$ absorption flux from existing lab-scale experiments as a first approximation. The predicted reboiler energy per ton of $CO_2$ removed is lower than the range typically reported for amine-based processes, mainly due to the semi-lean operation. However, the flash gas from the flash drum may need to undergo further sweetening in order to be used as fuel gas due to high $CO_2$ loading in rich amine. The predicted amine loss rate per treated gas and per ton of $CO_2$ removed is below the typical loss rates reported in conventional amine-based processes. These full-scale MBC results could provide the base case in a systematic model-based optimisation to improve the design and operation of commercial MBC modules as part of future work.

Although only certain embodiments of the present invention have been described in detail, many variations are possible in accordance with the appended claims. For example, features described in relation to one embodiment may be incorporated into one or more other embodiments and vice versa.

Further, it should be appreciated that although specific programmes or software are used in the embodiments as described, they are not to be considered limiting. Other suitable programmes or software can be used incorporating the aforementioned models, equations and/or boundary conditions to achieve the technical effects as discussed.

The invention claimed is:

1. A computer-implemented method for designing and assessing the performance of a hollow fibre membrane contactor (MBC) in a natural gas sweetening process using a MBC model, wherein the MBC model comprises model parameters, model equations and boundary conditions for calculating data associated with the natural gas sweetening process and the natural gas sweetening process comprises removal of acid gas from natural gas using a solvent comprising at least one component, the method comprising:
    forming a regression model using empirical data; determining a Henry's constant of $CO_2$ in the solvent using the regression model;
    inputting the determined Henry's constant of $CO_2$ in the MBC model as one of the model parameters; and determining $CO_2$ absorption in the solvent using the MBC model for designing and assessing the performance of the MBC.

2. The computer-implemented method of claim 1, further comprising: forming a regression model for a Henry's constant of nitrous oxide ($N_2O$) using empirical data of $N_2O$ solubility in the solvent; determining the Henry's constant of $N_2O$ using the regression model for the Henry's constant of $N_2O$; and determining the Henry's constant of $CO_2$ in the solvent using the Henry's constant of $N_2O$ to account for $CO_2$ loading in the solvent.

3. The computer-implemented method of claim 2, wherein the solvent comprises 50% methyldiethanolamine (MDEA) by weight, the regression model for the Henry's constant of nitrous oxide ($N_2O$) is modelled as:

$$H_{N_2O,l} = -3.30 \times 10^4 - 3.79 \times 10^4 f_{CO_2,l}^{in} + 1.70 \times 10^2 T_l - 4.37 \times 10^3 (f_{CO_2,l}^{in})^2 - 1.34 \times 10^{-1} T_l^2 + 1.45 \times 10^2 f_{CO_2,l}^{in} T_l$$

where $f_{CO_2,l}^{in}$ is associated with an inlet $CO_2$ loading in the solvent and $T_l$ is a liquid temperature of the solvent.

4. The computer-implemented method of claim 1, further comprising:
forming a regression model for a Henry's constant of a hydrocarbon in the solvent using empirical data of the hydrocarbon solubility in the solvent to account for hydrocarbon loss from the natural gas to the solvent; and
determining the Henry's constant of the hydrocarbon in the solvent using the regression model for the Henry's constant of the hydrocarbon.

5. The computer-implemented method of claim 4, further comprising:
determining a loss rate of the hydrocarbon in the solvent using the Henry's constant of the hydrocarbon in a hydrocarbon rate loss equation, wherein the loss rate of the hydrocarbon is a function of a concentration of the hydrocarbon, and wherein the concentration of the hydrocarbon is inversely proportional to the Henry's constant of the hydrocarbon in the solvent.

6. The computer-implemented method of claim 5, wherein the solvent is taken to be saturated with hydrocarbons at a liquid outlet of the MBC.

7. The computer-implemented method of claim 4, wherein the regression model for the Henry's constant of hydrocarbon is modelled as:

$$H_{i,l} = \alpha_0 + \alpha_1 C + \alpha_2 T_l + \alpha_3 P_l + \alpha_4 CT_l + \alpha_5 CP_l + \alpha_6 T_l P_l$$

where $T_l$ is a liquid temperature of the solvent, $P_l$ is a liquid pressure of the solvent, C is a mass fraction of the at least one component in the solvent, and coefficients $\alpha_1$ to $\alpha_6$ are parameters of the regression model for the Henry's constant of hydrocarbon.

8. The computer-implemented method of claim 1, further comprising:
determining a molar fraction of the at least one component of the solvent in the gas outlet using Raoult's Law; and
determining a solvent loss rate using the molar fraction in a solvent rate loss equation, wherein the solvent loss rate is proportional to the determined molar fraction.

9. The computer-implemented method of claim 8, wherein treated gas at a gas outlet of the MBC is taken to be saturated with the solvent, and the natural gas and the solvent is taken to be at equilibrium at the gas outlet.

10. The computer-implemented method of claim 8, further comprising determining an energy consumed for solvent evaporation and a liquid temperature of the solvent at a liquid inlet of the MBC using the solvent loss rate.

11. The computer-implemented method of claim 10, wherein solvent evaporation is taken to occur at the liquid inlet before the solvent reacts with the $CO_2$ in the natural gas along a length of the MBC.

12. The computer-implemented method of claim 11, further comprising:
determining a change in the liquid temperature by balancing the energy consumed for solvent evaporation with an exothermic $CO_2$ absorption reaction under adiabatic conditions along the length of the MBC.

13. The computer-implemented method of claim 12, wherein thermal diffusion along a radial axis is neglected and the liquid temperature is taken to be homogenous in the radial direction.

14. A computer-implemented method for assessing a performance of the natural gas sweetening process, the natural gas sweetening process comprising absorption operations and desorption operations, wherein the absorption operations are associated with acid gas absorption using the hollow fibre membrane contactor (MBC) and the desorption operations are associated with solvent regeneration using a solvent regenerator, and wherein the absorption operations are modelled based on the MBC model using the computer-implemented method of claim 1.

15. The computer-implemented method of claim 14, further comprising:
calculating an optimised flowrate associated with each of a lean operation and a semi-lean operation for achieving a predetermined $CO_2$ purity in the natural gas, the lean operation being an operation associated with using a lean solvent having less than 0.02 mol mol$^{-1}$ of $CO_2$ loading and the semi-lean operation being an operation associated with using a semi-lean solvent having more than 0.2 mol mol$^{-1}$ of $CO_2$ loading; and
determining a total process duty for the natural gas sweetening process associated with the absorption operations and the desorption operations under the lean operation and semi-lean operation.

16. The computer-implemented method of claim 15, further comprising: calculating a pressure for operating a rich solution flash drum associated with each of the lean operation and the semi-lean operation for achieving a predetermined lower heating value of a fuel gas, the fuel gas being a gas recovered from hydrocarbons loss in the solvent during the natural gas sweetening process.

17. A computer readable medium storing processor executable instructions which when executed on a processor cause the processor to carry out a method according to claim 1.

18. A computer-implemented method for designing and assessing the performance of a hollow fibre membrane contactor (MBC) in a natural gas sweetening process using a MBC model, wherein the MBC model comprises model parameters, model equations and boundary conditions for calculating data associated with the natural gas sweetening process and the natural gas sweetening process comprises removal of acid gas from natural gas using a solvent comprising at least one component, the method comprising:
forming a regression model for a Henry's constant of hydrocarbon in the solvent using empirical data of the hydrocarbon solubility in the solvent to account for hydrocarbon loss from the natural gas to the solvent, wherein the regression model is a function of a temperature of the solvent, a pressure of the solvent and a mass fraction of the at least one component in the solvent;

determining the Henry's constant of the hydrocarbon in the solvent;

determining a loss rate of the hydrocarbon in the solvent using the Henry's constant of the hydrocarbon in a hydrocarbon rate loss equation to account for hydrocarbon loss from the natural gas to the solvent, wherein the loss rate of the hydrocarbon is a function of the concentration of the hydrocarbon, and wherein the concentration of the hydrocarbon is inversely proportional to the Henry's constant of the hydrocarbon; and determining $CO_2$ absorption in the solvent using the MBC model for designing and assessing the performance of the hollow fibre membrane contactor, wherein the hydrocarbon rate loss equation is included as one of the model equations of the MBC model.

19. A hollow fibre membrane contactor (MBC) data processing system for designing and assessing a performance of a hollow fibre membrane contactor (MBC) in a natural gas sweetening process using a MBC model, wherein the MBC model comprises model parameters, model equations and boundary conditions for calculating data associated with the natural gas sweetening process and the natural gas sweetening process comprises removal of acid gas from natural gas using a solvent comprising at least one component, the MBC data processing system comprising a processor and a data storage device storing computer program instructions operable to cause the processor to:

form a regression model using empirical data;

determine a Henry's constant of $CO_2$ in the solvent using the regression model;

input the determined Henry's constant of $CO_2$ in the MBC model as one of the model parameters; and determine $CO_2$ absorption in the solvent using the MBC model for designing and assessing the performance of the MBC.

20. A natural gas sweetening process operating system comprising the MBC data processing system of claim 19 and a solvent regeneration data processing system, the MBC data processing system is associated with absorption operations for acid gas absorption using the hollow fibre membrane contactor (MBC) and the solvent regeneration data processing system is associated with desorption operations for solvent regeneration using a solvent regenerator.

* * * * *

UNITED STATES PATENT AND TRADEMARK OFFICE
CERTIFICATE OF CORRECTION

| | |
|---|---|
| PATENT NO. | : 12,370,492 B2 |
| APPLICATION NO. | : 17/915321 |
| DATED | : July 29, 2025 |
| INVENTOR(S) | : Quek et al. |

Page 1 of 1

It is certified that error appears in the above-identified patent and that said Letters Patent is hereby corrected as shown below:

On the Title Page

Item (72) Inventors:, delete "Benoit" and replace with --Benoît--

Signed and Sealed this
Twenty-sixth Day of August, 2025

Coke Morgan Stewart
*Acting Director of the United States Patent and Trademark Office*